US011306101B2

(12) United States Patent
Baculi et al.

(10) Patent No.: US 11,306,101 B2
(45) Date of Patent: Apr. 19, 2022

(54) SUBSTITUTED 1-OXO-ISOINDOLINE-5-CARBOXAMIDE COMPOUNDS, COMPOSITIONS THEREOF, AND METHODS OF TREATMENT THEREWITH

(71) Applicant: Celgene Corporation, Summit, NJ (US)

(72) Inventors: Frans Baculi, San Diego, CA (US); Katherine Northcote, San Diego, CA (US); Matthew D. Correa, San Diego, CA (US); Joshua Hansen, La Jolla, CA (US); Laurie A. Lebrun, San Diego, CA (US); Chin-Chun Lu, San Diego, CA (US); Gang Lu, San Diego, CA (US); Mark A. Nagy, San Diego, CA (US); Sophie Peng, San Diego, CA (US); Sophie Perrin-Ninkovic, La Jolla, CA (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 16/887,766

(22) Filed: May 29, 2020

(65) Prior Publication Data
US 2020/0377512 A1    Dec. 3, 2020

Related U.S. Application Data

(60) Provisional application No. 62/855,619, filed on May 31, 2019.

(51) Int. Cl.
| | | |
|---|---|---|
| C07D 401/04 | (2006.01) | |
| C07D 401/14 | (2006.01) | |
| C07D 405/14 | (2006.01) | |
| C07D 413/14 | (2006.01) | |
| C07D 491/107 | (2006.01) | |
| A61P 35/02 | (2006.01) | |

(52) U.S. Cl.
CPC .......... C07D 491/107 (2013.01); A61P 35/02 (2018.01); C07D 401/04 (2013.01); C07D 401/14 (2013.01); C07D 405/14 (2013.01); C07D 413/14 (2013.01)

(58) Field of Classification Search
CPC .. C07D 401/04; C07D 401/14; C07D 405/14; C07D 413/14
See application file for complete search history.

(56) References Cited

U.S. PATENT DOCUMENTS

| | | |
|---|---|---|
| 2003/0096841 A1 | 5/2003 | Robarge et al. |
| 2011/0144158 A1 | 6/2011 | Muller et al. |
| 2015/0005303 A1 | 1/2015 | Muller et al. |
| 2018/0134684 A1 | 5/2018 | Bradner et al. |

FOREIGN PATENT DOCUMENTS

WO    WO 2020/243379 A1    12/2020

OTHER PUBLICATIONS

Evans in "Principles of Radiopharmacology", Colombett, L.G. editor, CRC Press, pp. 11-13 and 24 (1979).*
CA Registry No. 2369870-18-6, entered into the Registry File on Aug. 29, 19, supplied by InterMed Chemical Library.*
InterMed Product guide, 2 pages retrieved from the Internet at http://intermedchemicals.com>products on Jul. 17, 21.*
Elyada et al., "CKIα ablation highlights a critical role for p53 in invasiveness control." Nature 470.7334 (2011): 409-413.
International Search Report and Written Opinion issued for PCT/US2020/035043 dated Sep. 16, 2020 (11 pages).
Jaras et al., "Csnk1a1 inhibition has p53-dependent therapeutic efficacy in acute myeloid leukemia." Journal of Experimental Medicine 211.4 (2014): 605-612.
Leone et al, "DNA methylation and demethylating drugs in myelodysplastic syndromes and secondary leukemias." haematologica 87.12 (2002): 1324-1341.
Liu et al., "Control of β-catenin phosphorylation/degradation by a dual-kinase mechanism." Cell 108.6 (2002): 837-847.
Lowenberg et al, "Acute myeloid leukemia." New England Journal of Medicine 341.14 (1999): 1051-1062.
Luis et al., "Canonical wnt signaling regulates hematopoiesis in a dosage-dependent fashion." Cell stem cell 9.4 (2011): 345-356.
Michaelis, Laura C. "Cytotoxic therapy in acute myeloid leukemia: not quite dead yet." Hematology 2014, the American Society of Hematology Education Program Book 2018.1 (2018): 51-62.
Milligan et al, "Guidelines on the management of acute myeloid leukaemia in adults." British journal of haematology 135.4 (2006): 450-474.
National Center for Biotechnology Information. "PubChem Compound Summary for CID 124190295, CID 124190295" PubChem, https://pubchem.ncbi.nlm.nih.gov/compound/124190295. Accessed Jul. 12, 2021.

(Continued)

Primary Examiner — Emily A Bernhardt
(74) Attorney, Agent, or Firm — Jones Day

(57) ABSTRACT

Provided herein are 1-oxo-isoindoline-5-carboxamide compounds having the following structure:

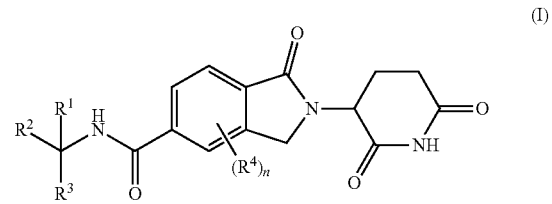

wherein $R^1$, $R^2$, $R^3$, $R^4$ and n are as defined herein, compositions comprising an effective amount of a 1-oxo-isoindoline-5-carboxamide compound, and methods for treating or preventing disorders.

35 Claims, No Drawings

(56) References Cited

OTHER PUBLICATIONS

National Center for Biotechnology Information. "PubChem Compound Summary for CID 146149788, CID 146149788" PubChem, https://pubchem.ncbi.nlm.nih.gov/compound/146149788. Retrieved from internet Jul. 12, 2021.
National Center for Biotechnology Information. "PubChem Compound Summary for CID 69048987" PubChem, https://pubchem.ncbi.nlm.nih.gov/compound/69048987. Accessed Jul. 12, 2021.
Pollyea, Daniel A. "New drugs for acute myeloid leukemia inspired by genomics and when to use them." Hematology 2014, the American Society of Hematology Education Program Book 2018.1 (2018): 45-50.
Silverman et al., Cancer Medicine. 5th ed. Hamilton, Canada: BC Decker; 2000. p. 1931-1946).
Tallman, Hematology Am Soc Hematol Educ Program 2005:143-150.
Wang et al., "The Wnt/β-catenin pathway is required for the development of leukemia stem cells in AML." Science 327.5973 (2010): 1650-1653.
Wilen, et al., "Strategies in optical resolutions." Tetrahedron 33.21 (1977): 2725-2736.
Zhao et al., "P53 loss promotes acute myeloid leukemia by enabling aberrant self-renewal." Genes & development 24.13 (2010): 1389-1402.

\* cited by examiner

SUBSTITUTED 1-OXO-ISOINDOLINE-5-CARBOXAMIDE COMPOUNDS, COMPOSITIONS THEREOF, AND METHODS OF TREATMENT THEREWITH

RELATED APPLICATIONS

This application claims the benefit of U.S. Provisional Application No. 62/855,619, filed May 31, 2019, the disclosure of which is incorporated herein by reference in its entirety.

FIELD

Provided herein are certain 1-oxo-isoindoline-5-carboxamide compounds, compositions comprising an effective amount of such compounds, and methods for treating or preventing acute myeloid leukemia (AML), comprising administering an effective amount of such 1-oxo-isoindoline-5-carboxamide compounds to a subject in need thereof. Further provided herein are such 1-oxo-isoindoline-5-carboxamide compounds and compositions comprising an effective amount of such compounds for use in said methods.

BACKGROUND

Acute myeloid leukemia is the most commonly reported type of acute leukemia in adults in the United States (US). Based on the American Cancer Society's estimates, approximately 20,830 people will be diagnosed with AML in 2015 in the US and 10,460 patients will die from the disease (American Cancer Society. Cancer Facts & Figures 2015. Atlanta, Ga.: American Cancer Society; 2015). The median age at diagnosis is approximately 67 years.

Acute myeloid leukemia can arise de novo, be secondary to previous cytotoxic chemotherapy, or arise through transformation of existing myelodysplasia. Therapy-related AML arising from exposure to environmental toxins, cytotoxic drugs, or radiation currently accounts for about 5% to 10% of all cases of AML (Leone et al, *Haematologica* 1999; 84(10):937-945). It is estimated that 35% to 40% of patients with myelodysplastic syndromes will go on to develop AML, with the disease often refractory to current therapy (Silverman et al, *Cancer Medicine*. 5th ed. Hamilton, Canada: BC Decker; 2000. p. 1931-1946). Preexisting myelodysplastic or myeloproliferative disorders are common in older patients with AML, occurring in 24% to 40% of cases (Gajewski et al, *J Clin Oncol* 1989; 7:1637-1645). Patients with secondary AML due to prior hematologic disease have a lesser response to therapy than those with de novo disease.

The usual treatment of AML is divided into two phases: induction of remission and consolidation therapy. For more than 30 years, the combination of cytarabine and an anthracycline has been the mainstay of treatments to induce remission (Lowenberg et al, *N Engl J Med* 1999; 341:1051-1062; Tallman, *Hematology* Am Soc Hematol Educ Program 2005:143-150). The remission induction therapy in leukemia is designed to produce the rapid restoration of normal bone marrow function. A common induction regimen consists of cytarabine, 7 days combined with daunorubicin for 3 days, often referred to as the "7+3 protocol." With the combination of cytarabine and daunorubicin or their analogues, a CR, conventionally defined morphologically by the presence of <5% blasts in the bone marrow together with the recovery of peripheral-blood absolute neutrophil and platelet counts, can be achieved in up to 70% to 80% of adults with de novo AML who are <60 years of age (Lowenberg et al, *N Engl J Med* 1999; 341:1051-1062; Tallman, *Hematology* Am Soc Hematol Educ Program 2005:143-150). If CR is achieved, there are 3 basic treatment choices for post-remission therapy: additional chemotherapy, stem cell transplantation from a donor (allogeneic stem cell transplantation), or stem cell transplantation using the patient's own stem cells (autologous stem cell transplantation). For post-remission chemotherapy, the same chemotherapy regimen used for remission induction or a higher dose regimen of cytarabine is often repeated for one or more cycles, referred to as consolidation chemotherapy. When several courses of consolidation are given, survival rates at 2-3 years are 35% to 50% for young to middle-age adults who have achieved CR (Milligan et al, *B J Hem* 2006; 135:450-474). However, consolidation or post-remission chemotherapy for elderly patients with AML has not been proven beneficial.

Given the poor overall outcome and high treatment-related mortality in older AML patients, some physicians do not pursue aggressive induction therapy, opting for less aggressive therapies. Treatment options are few for patients who choose not to receive intensive chemotherapy or are considered ineligible (unfit) to receive intensive chemotherapy by their physician. Treatment options for these patients include low-intensity therapies such as low-dose cytarabine or supportive care only.

Due to the extensive work involving the sequencing of AML patient samples, mutational profiles associated with AML have been uncovered, which has led to routine comprehensive sequencing in clinical care and the development of targeted therapies (Pollyea, *Hematology* 2018; 45-50, 2018; Michaelis, *Hematology* 2018; 51-62). Recently, several new treatments for AML have received FDA approval. In 2017, the FDA approved enasidenib (Idhifa®) for the treatment of relapsed/refractory AML with an IDH2 mutation. In 2018, the FDA approved ivosidenib (Tibsovo®), for the treatment of relapsed/refractory AML with an IDH1 mutation. In 2018, the FDA approved gilteritinib (Xospata®) for treating patients whose AML tests positive for a FLT3 gene mutation, as well as glasdegib (Daurismo™) and venetoclax (Venclexta®) for treating patients with newly diagnosed AML who are age 75 or older, or who have chronic health conditions or diseases that prevent them being treated with the standard intensive chemotherapy. All are targeted therapies and, except for gilteritinib, are indicated to be used in combination treatments (glasdegib with low dose cytarabine, and venetoclax with azacitidine or decitabine or low-dose cytarabine). Despite these recent advances, the majority of patients treated with these agents will relapse or be refractory.

Casein kinase-1α (CK1α), also named Csnk1a1, is a serine-threonine kinase, and is a central regulator of multiple pathways that are critical for normal and malignant stem cell biology, including the β catenin and p53 pathways (Liu et al., *Cell* 2002; 108:837-847; Wang et al., *Science* 2010; 327:1650-1653; Zhao et al., *Genes Dev.* 2010; 24:1389-1402; Elyada et al., *Nature* 2011; 470:409-413; Luis et al., *Cell Stem Cell* 2011; 9:345-356). Additionally, CK1α has been shown to play a critical role in the biology of AML (Järås M et al, *J Exp Med.* 2014; 211(4):605-612). CK1α inhibitors have been reported, however, none have been approved for the treatment of AML.

There remains a significant need for safe and effective methods of treating, preventing and managing AML, particularly for AML that is refractory to standard treatments, such as surgery, radiation therapy, chemotherapy and biological therapy, while reducing or avoiding the toxicities and/or side effects associated with conventional therapies.

Citation or identification of any reference in this section of this application is not to be construed as an admission that the reference is prior art to the present application.

SUMMARY

Provided herein are compounds having the following formula (I):

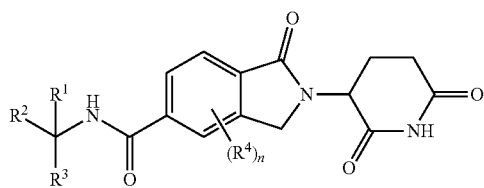

or a pharmaceutically acceptable salt, tautomer, isotopolog, or stereoisomer thereof, wherein $R^1$, $R^2$, $R^3$ $R^4$, and n are as defined herein.

A compound of formula (I) or a pharmaceutically acceptable salt, tautomer, isotopolog, or stereoisomer thereof (each being referred to herein as an "Isoindolinone Carboxamide Compound") is useful for reducing CK1α protein levels and for treating or preventing AML.

In one aspect, provided herein are Isoindolinone Carboxamide Compounds as described in the instant disclosure, such as, for example, in Table 1 or a pharmaceutically acceptable salt, tautomer, isotopolog, and stereoisomer thereof. In one aspect, provided herein are Isoindolinone Carboxamide Compounds as described in Table 1 or a pharmaceutically acceptable salt thereof. In one aspect, provided herein are Isoindolinone Carboxamide Compounds as described in Table 1.

In one aspect, provided herein are pharmaceutical compositions comprising an effective amount of an Isoindolinone Carboxamide Compound as described herein, and a pharmaceutically acceptable carrier, excipient or vehicle. In some embodiments the pharmaceutical composition is suitable for oral, parenteral, mucosal, transdermal or topical administration.

In one aspect, provided herein are methods for treating or preventing AML, comprising administering to a subject in need thereof an effective amount of an Isoindolinone Carboxamide Compound as described herein; and a pharmaceutically acceptable carrier, excipient or vehicle. In one aspect, provided herein are methods for reducing CK1α protein levels, comprising administering to a subject in need thereof an effective amount of an Isoindolinone Carboxamide Compound as described herein; and a pharmaceutically acceptable carrier, excipient or vehicle. In another aspect, provided herein are Isoindolinone Carboxamide Compounds for use in the treatment of AML. In another aspect, provided herein are Isoindolinone Carboxamide Compounds for use in reducing CK1α protein levels.

In another aspect provided herein are methods for preparing Isoindolinone Carboxamide Compounds as described herein.

The present embodiments can be understood more fully by reference to the detailed description and examples, which are intended to exemplify non-limiting embodiments.

DETAILED DESCRIPTION

Definitions

As used herein, the term "or" is to be interpreted as an inclusive "or" meaning any one or any combination. Therefore, "A, B or C" means any of the following. "A; B; C; A and B; A and C; B and C; A, B and C". An exception to this definition will occur only when a combination of elements, functions, steps or acts are in some way inherently mutually exclusive.

As used herein and unless otherwise specified, an "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, -neopentyl, tert-pentyl, -2-methylpentyl, -3-methylpentyl, -4-methylpentyl, -2,3-dimethylbutyl and the like. An "alkenyl" group is an alkyl group that contains one or more carbon-carbon double bonds. An "alkynyl" group is an alkyl group that contains one or more carbon-carbon triple bonds. Examples of unsaturated alkyl groups include, but are not limited to, vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, —C≡CH, —C≡C(CH$_3$), —C≡C(CH$_2$CH$_3$), —CH$_2$C≡CH, —CH$_2$C≡C(CH$_3$) and —CH$_2$C≡C(CH$_2$CH$_3$), among others. An alkyl group can be substituted or unsubstituted. When the alkyl groups described herein are said to be "substituted," they may be substituted with any substituent or substituents as those found in the exemplary compounds and embodiments disclosed herein, as well as halogen; hydroxy; alkoxy; cycloalkyloxy, aryloxy, heterocyclyloxy, heteroaryloxy, heterocycloalkyloxy, cycloalkylalkyloxy, aralkyloxy, heterocyclylalkyloxy, heteroarylalkyloxy, heterocycloalkylalkyloxy; oxo (=O); amino, alkylamino, cycloalkylamino, arylamino, heterocyclylamino, heteroarylamino, heterocycloalkylamino, cycloalkylalkylamino, aralkylamino, heterocyclylalkylamino, heteroaralkylamino, heterocycloalkylalkylamino; imino; imido; amidino; guanidino; enamino; acylamino; sulfonylamino; urea, nitrourea; oxime; hydroxylamino; alkoxyamino; aralkoxyamino; hydrazino; hydrazido; hydrazono; azido; nitro; thio (—SH), alkylthio; =S; sulfinyl; sulfonyl; aminosulfonyl; phosphonate; phosphinyl; acyl; formyl; carboxy; ester; carbamate; amido; cyano; isocyanato; isothiocyanato; cyanato; thiocyanato; or —B(OH)$_2$.

As used herein and unless otherwise specified, a "cycloalkyl" group is a saturated, or partially saturated cyclic alkyl group of from 3 to 10 carbon atoms having a single cyclic ring or multiple condensed or bridged rings which can be optionally substituted. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as 1-bicyclo[1.1.1]pentyl, bicyclo[2.1.1]hexyl, bicyclo[2.2.1]heptyl, bicyclo[2.2.2]octyl, adamantyl and the like. Examples of unsaturared cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanol and the like.

As used herein and unless otherwise specified, an "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryl groups include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

As used herein and unless otherwise specified, a "heteroaryl" group is an aromatic ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, benzisoxazolyl (e.g., benzo[d]isoxazolyl), thiazolyl, pyrolyl, pyridazinyl, pyrimidyl, pyrazinyl, thiophenyl, benzothiophenyl, furanyl, benzofuranyl, indolyl (e.g., indol-2-onyl), isoindolin-1-onyl, azaindolyl, pyrrolopyridyl (e.g., 1H-pyrrolo[2,3-b]pyridyl), indazolyl, benzimidazolyl (e.g., 1H-benzo[d]imidazolyl), azabenzimidazolyl, imidazopyridyl (e.g., 1H-imidazo[4,5-b]pyridyl), pyrazolopyridyl, triazolopyridyl, benzotriazolyl (e.g., 1H-benzo[d][1,2,3]triazolyl), benzoxazolyl (e.g., benzo[d]oxazolyl), benzothiazolyl, benzothiadiazolyl, isoxazolopyridyl, thianaphthalenyl, purinyl, xanthinyl, adeninyl, guaninyl, quinolinyl, isoquinolinyl, 3,4-dihydroisoquinolin-1(2H)-onyl, tetrahydroquinolinyl, quinoxalinyl, and quinazolinyl groups. A heteroaryl group can be substituted or unsubstituted.

As used herein and unless otherwise specified, a "heterocyclyl" is an aromatic ring system (also referred to as heteroaryl) or non-aromatic cycloalkyl (also referred to as heterocycloalkyl) in which one to four of the ring carbon atoms are independently replaced with a heteroatom. Suitable heteroatoms include oxygen, sulfur and nitrogen. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocyclyl group can be substituted or unsubstituted. Heterocyclyl groups encompass unsaturated, partially saturated and saturated ring systems, such as, for example, imidazolyl, imidazolinyl and imidazolidinyl (e.g., imidazolidin-4-onyl or imidazolidin-2,4-dionyl) groups. The phrase heterocyclyl includes fused ring species, including those comprising fused aromatic and non-aromatic groups, such as, for example, 1- and 2-aminotetraline, benzotriazolyl (e.g., 1H-benzo[d][1,2,3]triazolyl), benzimidazolyl (e.g., 1H-benzo[d]imidazolyl), 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, azepanyl, oxetanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, benzisoxazolyl (e.g., benzo[d]isoxazolyl), thiazolyl, thiazolinyl, isothiazolyl, thiadiazolyl, oxadiazolyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dioxyl, dithianyl, pyranyl, pyridyl, pyrimidyl, pyridazinyl, pyrazinyl, triazinyl, dihydropyridyl, dihydrodithiinyl, dihydrodithionyl, 1,4-dioxaspiro[4.5]decanyl, homopiperazinyl, quinuclidyl, indolyl (e.g., indol-2-onyl), isoindolin-1-onyl, indolinyl, isoindolyl, isoindolinyl, azaindolyl, pyrrolopyridyl (e.g, 1H-pyrrolo[2,3-b]pyridyl), indazolyl, indolizinyl, benzotriazolyl (e.g. 1H-benzo[d][1,2,3]triazolyl), benzimidazolyl (e.g., 1H-benzo[d]imidazolyl or 1H-benzo[d]imidazol-2(3H)-onyl), benzofuranyl, benzothiophenyl, benzothiazolyl, benzoxadiazolyl, benzoxazinyl, benzodithiinyl, benzoxathiinyl, benzothiazinyl, benzoxazolyl (e.g., benzo[d]oxazolyl), benzothiazolyl, benzothiadiazolyl, benzo[1,3]dioxolyl, pyrazolopyridyl (e.g., 1H-pyrazolo[3,4-b]pyridyl, 1H-pyrazolo[4,3-b]pyridyl), azabenzimidazolyl, imidazopyridyl (e.g., 1H-imidazo[4,5-b]pyridyl), triazolopyridyl, isoxazolopyridyl, purinyl, xanthinyl, adeninyl, guaninyl, quinolinyl, isoquinolinyl, 3,4-dihydroisoquinolin-1(2H)-onyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, tetrahydropyrimidin-2(1H)-one and tetrahydroquinolinyl groups. Representative non-aromatic heterocyclyl groups do not include fused ring species that comprise a fused aromatic group. Examples of non-aromatic heterocyclyl groups include aziridinyl, azetidinyl, azepanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dithianyl, 1,4-dioxaspiro[4.5]decanyl, homopiperazinyl, quinuclidyl, or tetrahydropyrimidin-2(1H)-one. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

As used herein and unless otherwise specified, a "cycloalkylalkyl" group is a radical of the formula: -alkyl-cycloalkyl, wherein alkyl and cycloalkyl are defined above. Substituted cycloalkylalkyl groups may be substituted at the alkyl, the cycloalkyl, or both the alkyl and the cycloalkyl portions of the group. Representative cycloalkylalkyl groups include but are not limited to cyclopropylmethyl, cyclobutylmethyl, cyclopentylmethyl, cyclohexylmethyl, cyclopropylethyl, cyclobutylethyl, cyclopentylethyl, cyclohexylethyl, cyclopentylpropyl, cyclohexylpropyl and the like.

As used herein and unless otherwise specified, an "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and aralkyl groups wherein the aryl group is fused to a cycloalkyl group such as indan-4-yl ethyl.

As used herein and unless otherwise specified, a "heterocyclylalkyl" group is a radical of the formula: -alkyl-heterocyclyl, wherein alkyl and heterocyclyl are defined above. A "heteroarylalkyl" group is a radical of the formula: -alkyl-heteroaryl, wherein alkyl and heteroaryl are defined above. A "heterocycloalkylalkyl" group is a radical of the formula: -alkyl-heterocycloalkyl, wherein alkyl and heterocycloalkyl are defined above. Substituted heterocyclylalkyl groups may be substituted at the alkyl, the heterocyclyl, or both the alkyl and the heterocyclyl portions of the group. Representative heterocylylalkyl groups include but are not limited to morpholin-4-yl ethyl, morpholin-4-yl propyl, furan-2-yl methyl, furan-3-yl methyl, pyridin-3-yl methyl, tetrahydrofuran-2-yl ethyl, and indol-2-yl propyl.

As used herein and unless otherwise specified, a "halogen" is fluorine, chlorine, bromine or iodine.

As used herein and unless otherwise specified, a "hydroxyalkyl" group is an alkyl group as described above substituted with one or more hydroxy groups.

As used herein and unless otherwise specified, an "alkoxy" group is —O-(alkyl), wherein alkyl is defined above. An "alkylthio" group is —S-(alkyl), wherein alkyl is defined above.

As used herein and unless otherwise specified, an "alkoxyalkyl" group is -(alkyl)-O-(alkyl), wherein alkyl is defined above.

As used herein and unless otherwise specified, a "cycloalkyloxy" group is —O-(cycloalkyl), wherein cycloalkyl is defined above.

As used herein and unless otherwise specified, an "aryloxy" group is —O-(aryl), wherein aryl is defined above.

As used herein and unless otherwise specified, a "heterocyclyloxy" group is —O-(heterocyclyl), wherein heterocyclyl is defined above. A "heteroaryloxy" group is —O-(heteroaryl), wherein heteroaryl is defined above. A "heterocycloalkyloxy" group is —O-(heterocycloalkyl), wherein heterocycloalkyl is defined above.

As used herein and unless otherwise specified, an "amino" group is a radical of the formula: —$NH_2$, —NH($R^\#$), or —N($R^\#$)$_2$, wherein each $R^\#$ is independently an alkyl, cycloalkyl, cycloalkylalkyl, aryl, aralkyl, heterocyclyl (e.g., heteroaryl or heterocycloalkyl), or heterocyclylalkyl (e.g., heteroarylalkyl or heterocycloalkylalkyl) group defined above, each of which is independently substituted or unsubstituted.

In one embodiment, an "amino" group is an "alkylamino" group, which is a radical of the formula: —NH-alkyl or —N(alkyl)$_2$, wherein each alkyl is independently defined above. The term "cycloalkylamino", "arylamino", "heterocyclylamino", "heteroarylamino", "heterocycloalkylamino", or the like, mirrors the above description for "alkylamino" where the term "alkyl" is replaced with "cycloalkyl", "aryl", "heterocyclyl", "heteroaryl", "heterocycloalkyl", or the like, respectively.

As used herein and unless otherwise specified, a "carboxy" group is a radical of the formula: —C(O)OH.

As used herein and unless otherwise specified, an "acyl" group is a radical of the formula: —C(O)($R^\#$) or —C(O)H, wherein $R^\#$ is defined above. A "formyl" group is a radical of the formula: —C(O)H.

As used herein and unless otherwise specified, an "amido" group is a radical of the formula: —C(O)—$NH_2$, —C(O)—NH($R^\#$), —C(O)—N($R^\#$)$_2$, —NH—C(O)H, —NH—C(O)—($R^\#$), —N($R^\#$)—C(O)H, or —N($R^\#$)—C(O)—($R^\#$), wherein each $R^\#$ is independently defined above.

In one embodiment, an "amido" group is an "aminocarbonyl" group, which is a radical of the formula: —C(O)—$NH_2$, —C(O)—NH($R^\#$), —C(O)—N($R^\#$)$_2$, wherein each $R^\#$ is independently defined above.

In one embodiment, an "amido" group is an "acylamino" group, which is a radical of the formula: —NH—C(O)H, —NH—C(O)—($R^\#$), —N($R^\#$)—C(O)H, or —N($R^\#$)—C(O)—($R^\#$), wherein each $R^\#$ is independently defined above.

As used herein and unless otherwise specified, a "sulfonylamino" group is a radical of the formula: —NHSO$_2$($R^\#$) or —N($R^\#$)SO$_2$($R^\#$), wherein each $R^\#$ is defined above.

As used herein and unless otherwise specified, an "ester" group is a radical of the formula: —C(O)—O—($R^\#$) or —O—C(O)—($R^\#$), wherein $R^\#$ is defined above.

In one embodiment, an "ester" group is an "alkoxycarbonyl" group, which is a radical of the formula: —C(O)—O-(alkyl), wherein alkyl is defined above. The term "cycloalkyloxycarbonyl", "aryloxycarbonyl", "heterocyclyloxycarbonyl", "heteroaryloxycarbonyl", "heterocycloalkyloxycarbonyl", or the like, mirrors the above description for "alkoxycarbonyl" where the term "alkoxy" is replaced with "cycloalkyloxy", "aryloxy", "heterocyclyloxy", "heteroaryloxy", "heterocycloalkyloxy", or the like, respectively.

As used herein and unless otherwise specified, a "carbamate" group is a radical of the formula: —O—C(O)—$NH_2$, —O—C(O)—NH($R^\#$), —O—C(O)—N($R^\#$)$_2$, —NH—C(O)—O—($R^\#$), or —N($R^\#$)—C(O)—O—($R^\#$), wherein each $R^\#$ is independently defined above.

As used herein and unless otherwise specified, a "urea" group is a radical of the formula: —NH(CO)$NH_2$, —NHC(O)NH($R^\#$), —NHC(O)N($R^\#$)$_2$, —N($R^\#$)C(O)$NH_2$, —N($R^\#$)C(O)NH($R^\#$), or —N($R^\#$)C(O)N($R^\#$)$_2$, wherein each $R^\#$ is independently defined above.

As used herein and unless otherwise specified, a "sulfinyl" group is a radical of the formula: —S(O)$R^\#$, wherein $R^\#$ is defined above.

As used herein and unless otherwise specified, a "sulfonyl" group is a radical of the formula: —S(O)$_2R^\#$, wherein $R^\#$ is defined above.

As used herein and unless otherwise specified, an "aminosulfonyl" group is a radical of the formula: —SO$_2NH_2$, —SO$_2$NH($R^\#$), or —SO$_2$N($R^\#$)$_2$, wherein each $R^\#$ is independently defined above.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen; alkyl, alkenyl, alkynyl, cycloalkyl, aryl, heterocyclyl, heteroaryl, heterocycloalkyl, cycloalkylalkyl, aralkyl, heterocyclylalkyl, heteroarylalkyl, heterocycloalkylalkyl, optionally further substituted; hydroxy; alkoxy; cycloalkyloxy, aryloxy, heterocyclyloxy, heteroaryloxy, heterocycloalkyloxy, cycloalkylalkyloxy, aralkyloxy, heterocyclylalkyloxy, heteroarylalkyloxy, heterocycloalkylalkyloxy; oxo (=O); oxide (e.g., a nitrogen atom substituted with an oxide is called N-oxide); amino, alkylamino, cycloalkylamino, arylamino, heterocyclylamino, heteroarylamino, heterocycloalkylamino, cycloalkylalkylamino, aralkylamino, heterocyclylalkylamino, heteroaralkylamino, heterocycloalkylalkylamino; imino; imido; amidino; guanidino; enamino; acylamino; sulfonylamino; urea, nitrourea; oxime; hydroxylamino; alkoxyamino; aralkoxyamino; hydrazino; hydrazido; hydrazono; azido; nitro; thio (—SH), alkylthio; =S; sulfinyl; sulfonyl; aminosulfonyl; phosphonate; phosphinyl; acyl; formyl; carboxy; ester; carbamate; amido; cyano; isocyanato; isothiocyanato; cyanato; thiocyanato; or —B(OH)$_2$.

As used herein, the term "Isoindolinone Carboxamide Compound" refers to compounds of formula (I), such as formulas (II)-(XI), as well as to further embodiments provided herein. In one embodiment, an "Isoindolinone Carboxamide Compound" is a compound set forth in Table 1. The term "Isoindolinone Carboxamide Compound" includes pharmaceutically acceptable salts, tautomers, isotopologs, and stereoisomers of the compounds provided herein.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds of formula (I) include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride and mesylate salts. Others are well-known in the art, see for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995).

As used herein and unless otherwise indicated, the term "stereoisomer" or "stereomerically pure" means one stereoisomer of an Isoindolinone Carboxamide Compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Isoindolinone Carboxamide Compounds can have chiral centers and can occur as racemates, individual enantiomers or diastereomers, and mixtures thereof. All such isomeric forms are included within the embodiments disclosed herein, including mixtures thereof.

The use of stereomerically pure forms of such Isoindolinone Carboxamide Compounds, as well as the use of mixtures of those forms, are encompassed by the embodiments disclosed herein. For example, mixtures comprising equal or unequal amounts of the enantiomers of a particular Isoindolinone Carboxamide Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, New York, 1962); Wilen, S. H., *Tables of Resolving Agents and Optical Resolutions* p. 268 (E. L. Eliel, Ed., Univ. of Notre Dame Press, Notre Dame, Ind., 1972); Todd, M., *Separation Of Enantiomers: Synthetic Methods* (Wiley-VCH Verlag GmbH & Co. KGaA, Weinheim, Germany, 2014); Toda, F., *Enantiomer Separation: Fundamentals and Practical Methods* (Springer Science & Business Media, 2007); Subramanian, G. *Chiral Separation Techniques: A Practical Approach* (John Wiley & Sons, 2008); Ahuj a, S., *Chiral Separation Methods for Pharmaceutical and Biotechnological Products* (John Wiley & Sons, 2011).

It should also be noted the Isoindolinone Carboxamide Compounds can include E and Z isomers, or a mixture thereof, and cis and trans isomers or a mixture thereof. In certain embodiments, the Isoindolinone Carboxamide Compounds are isolated as either the E or Z isomer. In other embodiments, the Isoindolinone Carboxamide Compounds are a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

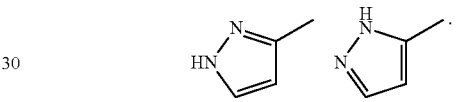

As readily understood by one skilled in the art, a wide variety of functional groups and other structures may exhibit tautomerism and all tautomers of compounds of formula (I) are within the scope of the present invention.

It should also be noted the Isoindolinone Carboxamide Compounds can contain unnatural proportions of atomic isotopes at one or more of the atoms. For example, the compounds may be radiolabeled with radioactive isotopes, such as for example tritium ($^{3}$H), iodine-125 ($^{125}$I), sulfur-35 ($^{35}$S), or carbon-14 ($^{14}$C), or may be isotopically enriched, such as with deuterium ($^{2}$H), carbon-13 ($^{13}$C), or nitrogen-15 ($^{15}$N). As used herein, an "isotopolog" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically encriched compounds are useful as therapeutic agents, e.g., cancer therapeutic agents, research reagents, e.g., binding assay reagents, and diagnostic agents, e.g., in vivo imaging agents. All isotopic variations of the Isoindolinone Carboxamide Compounds as described herein, whether radioactive or not, are intended to be encompassed within the scope of the embodiments provided herein. In some embodiments, there are provided isotopologs of the Isoindolinone Carboxamide Compounds, for example, the isotopologs are deuterium, carbon-13, and/or nitrogen-15 enriched Isoindolinone Carboxamide Compounds. As used herein, "deuterated", means a compound wherein at least one hydrogen (H) has been replaced by deuterium (indicated by D or $^{2}$H), that is, the compound is enriched in deuterium in at least one position.

It is understood that, independently of stereomerical or isotopic composition, each Isoindolinone Carboxamide Compound referred to herein can be provided in the form of any of the pharmaceutically acceptable salts discussed herein. Equally, it is understood that the isotopic composition may vary independently from the stereomerical composition of each Isoindolinone Carboxamide Compound referred to herein. Further, the isotopic composition, while being restricted to those elements present in the respective Isoindolinone Carboxamide Compound or salt thereof, may otherwise vary independently from the selection of the pharmaceutically acceptable salt of the respective Isoindolinone Carboxamide Compound.

It should be noted that if there is a discrepancy between a depicted structure and a name for that structure, the depicted structure is to be accorded more weight.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is AML as described herein or a symptoms thereof.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder is AML, as described herein, or symptoms thereof.

The term "effective amount" in connection with an Isoindolinone Carboxamide Compound means an amount capable of treating or preventing a disorder, disease or condition, or symptoms thereof, disclosed herein.

The term "CK1α" as used herein refers to Casein Kinase 1α, a kinase in humans that is encoded by the CSNK1A1 gene. CK1α has been shown to play a critical role in the biology of AML (Järås M et al, *J Exp Med.* 2014; 211(4): 605-612).

The term "degrade" or "degradation" as used herein means the degradation of a protein mediated by an E3 ligase, for example, CRBN, resulting in a reduction of the protein levels. In one embodiment, the protein is CK1α.

The term "subject" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having AML, or a symptom thereof.

Isoindolinone Carboxamide Compounds

Provided herein are compounds having the following formula (I):

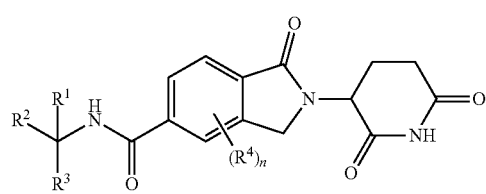

(I)

or a pharmaceutically acceptable salt, tautomer, isotopolog, or stereoisomer thereof, wherein:
R$^1$ is C$_{1-3}$ alkyl, or C$_{1-3}$ fluoroalkyl;
R$^2$ is substituted or unsubstituted C$_{1-6}$ alkyl, substituted or unsubstituted C$_{3-10}$ cycloalkyl, substituted or unsubstituted 3-6-membered heterocyclyl, substituted or unsubstituted C$_{6-10}$ aryl, or substituted or unsubstituted 5-10-membered heteroaryl;
R$^3$ is H;
R$^4$ is halogen; and
n is 0-3.

In some embodiments of compounds of formula (I), the compound is a compound of Formula (II)

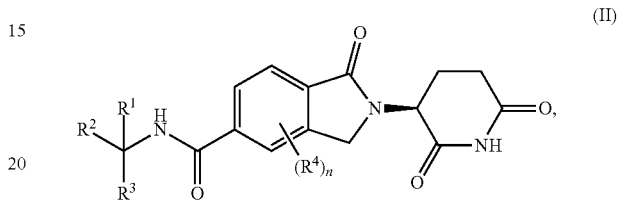

(II)

or a pharmaceutically acceptable salt, tautomer, isotopolog, or stereoisomer thereof.

In other embodiments of compounds of formula (I), the compound is a compound of Formula (III)

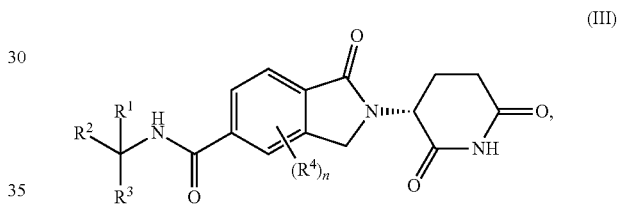

(III)

or a pharmaceutically acceptable salt, tautomer, isotopolog, or stereoisomer thereof.

In still other embodiments of compounds of formula (I), the compound is a compound of Formula (IV)

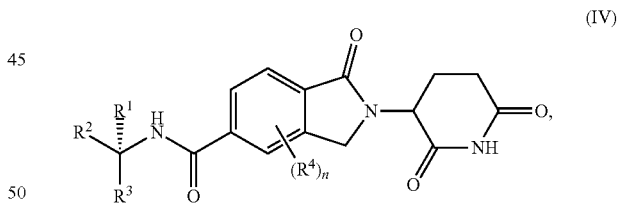

(IV)

or a pharmaceutically acceptable salt, tautomer, isotopolog, or stereoisomer thereof.

In yet other embodiments of compounds of formula (I), the compound is a compound of Formula (V)

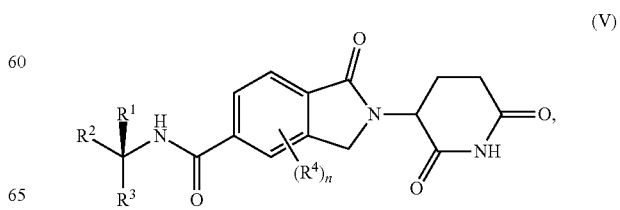

(V)

In some embodiments of compounds of formula (I), the compound is a compound of formula (VI)

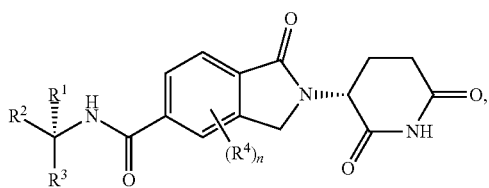
(VI)

or a pharmaceutically acceptable salt, tautomer, isotopolog, or stereoisomer thereof.

In other embodiments of compounds of formula (I), the compound is a compound of formula (VII)

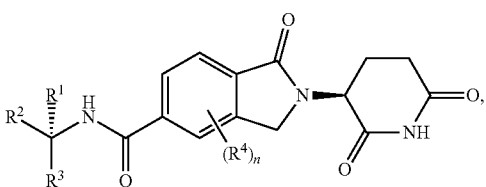
(VII)

or a pharmaceutically acceptable salt, tautomer, isotopolog, or stereoisomer thereof.

In still other embodiments of compounds of formula (I), the compound is a compound of formula (VIII)

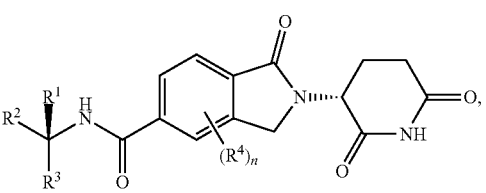
(VIII)

or a pharmaceutically acceptable salt, tautomer, isotopolog, or stereoisomer thereof.

In yet other embodiments of compounds of formula (I), the compound is a compound of formula (IX)

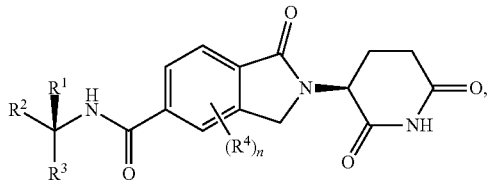
(IX)

or a pharmaceutically acceptable salt, tautomer, isotopolog, or stereoisomer thereof.

In other embodiments of compounds of formula (I), the compound is a compound of formula (X)

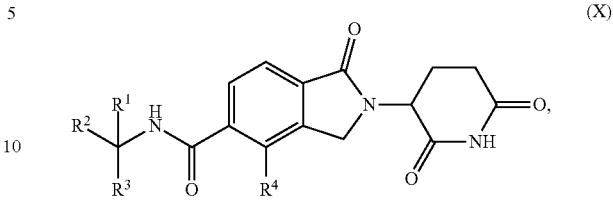
(X)

or a pharmaceutically acceptable salt, tautomer, isotopolog, or stereoisomer thereof.

In yet other embodiments of compounds of formula (I), the compound is a compound of formula (XI)

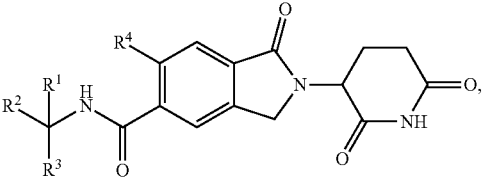
(XI)

or a pharmaceutically acceptable salt, tautomer, isotopolog, or stereoisomer thereof.

In some embodiments of compounds of formula (I)—(XI), $R^1$ is methyl, ethyl, n-propyl, isopropyl, $CH_2F$, $CHF_2$, $CF_3$, $CH_2CH_2F$, $CH_2CF_2$, $CH_2CF_3$, $CHFCH_3$, $CF_2CH_3$, or $CF_2CF_3$. In other embodiments, $R^1$ is methyl, ethyl, isopropyl, $CHF_2$, $CF_3$, $CH_2CF_3$, or $CF_2CH_3$.

In some embodiments of compounds of formula (I)—(XI), $R^2$ is substituted with one or more substituents selected from halogen, CN, OR', substituted or unsubstituted $C_{1-3}$ alkyl, and substituted or unsubstituted —($C_{0-3}$ alkyl)(3-6 membered heterocyclyl); wherein each R' is independently selected from H, substituted or unsubstituted $C_{1-3}$ alkyl, substituted or unsubstituted $C_{3-6}$ cycloalkyl, and phenyl. In such some embodiments, $R^2$ is substituted with one or more substituents selected from F, Cl, Br, CN, OH, $OCH_3$, $OCF_3$, $OCH_2CH_3$, O-n-propyl, O-isopropyl, O-n-butyl, O-sec-butyl, O-tert-butyl, O-cyclopropyl, O-cyclobutyl, O-phenyl, $CH_3$, $CH_2CH_3$, $CF_3$, $CH_2CF_3$, $CH_2NHCH_3$, $CH_2N(CH_3)_2$, and a —($C_{0-3}$ alkyl)(3-6 membered heterocyclyl) selected from piperidyl, piperazinyl, morpholino, $CH_2$-aziridyl, $CH_2$-pyrrolidyl, $CH_2$-piperazinyl, $CH_2$-piperidyl, $CH_2$-morpholinyl, $CH_2$(2-oxa-6-azaspiro[3.3]heptyl), wherein the —($C_{0-3}$ alkyl)(3-6 membered heterocyclyl) is optionally substituted with one or more F, Cl or $CH_3$. For example, in some embodiments of compounds of formula (I)—(XI), $R^2$ is substituted with one or more substituents selected from F, Cl, CN, OH, $OCH_3$, $OCF_3$, O-isopropyl, O-cyclopropyl, O-phenyl, $CH_3$, $CF_3$, $CH_2CF_3$, $CH_2N(CH_3)_2$, and a —($C_{0-3}$ alkyl)(3-6 membered heterocyclyl) selected from morpholino, piperazinyl, $CH_2$-aziridyl, $CH_2$-pyrrolidyl, $CH_2$-piperazinyl, $CH_2$-morpholinyl, and $CH_2$(2-oxa-6-azaspiro [3.3]heptyl), wherein the —($C_{0-3}$ alkyl)(3-6 membered heterocyclyl) is optionally substituted with one or more F or $CH_3$.

In some embodiments of compounds of formula (I)—(XI), $R^2$ is $C_{1-6}$ alkyl, unsubstituted or substituted with one or more substituents independently selected from halogen, CN, and OR'; $C_{3-10}$ cycloalkyl, unsubstituted, or substituted with one or more substitutents independently selected from halogen, OR', and substituted or unsubstituted $C_{1-3}$ alkyl;

3-6-membered heterocyclyl, unsubstituted, or substituted with one or more substituted or unsubstituted $C_{1-3}$ alkyl; $C_{6-10}$ aryl, unsubstituted or substituted with one or more substituents independently selected from halogen, CN, OR', substituted or unsubstituted $C_{1-3}$ alkyl, and substituted or unsubstituted —($C_{0-3}$ alkyl)(3-6 membered heterocyclyl); or 5-10-membered heteroaryl unsubstituted or substituted with one or more substituents independently selected from halogen, OR', and substituted or unsubstituted $C_{1-3}$ alkyl; wherein each R' is independently selected from H, substituted or unsubstituted $C_{1-3}$ alkyl, substituted or unsubstituted $C_{3-6}$ cycloalkyl, and phenyl. In some embodiments of compounds of formula (I)—(XI), $R^2$ is $C_{1-6}$ alkyl, unsubstituted or substituted with one or more substituents independently selected from F, CN, and OH. In some such embodiments, $R^2$ is $CH_3$, isopropyl, ter-butyl, $C(CH_3)_2CH_2OH$, $C(CH_3)_2CN$, or $C(CH_3)_2CF_3$. In some other embodiments of compounds of formula (I)—(XI), $R^2$ is $C_{3-10}$ cycloalkyl, unsubstituted, or substituted with one or more substitutents independently selected from F, OH, $CH_3$, $C(CH_3)_2OH$, and $CF_3$. In some such embodiments, $R^2$ is cyclopropyl, cyclobutyl, cyclopentyl, cyclohexyl, spiro[3.5]nonyl, bicyclo[1.1.1]pentyl, or spiro[2.5]octyl. In yet other embodiments of compounds of formula (I)—(XI), $R^2$ is 3-6-membered heterocyclyl, unsubstituted, or substituted with one or more $CH_3$, and $CH_2CF_3$. In some such embodiments, $R^2$ is oxetanyl, tetrahydropyranyl or piperidyl. In still other embodiments of compounds of formula (I)—(XI), $R^2$ is $C_{6-10}$ aryl, unsubstituted or substituted with one or more substituents independently selected from F, Cl, CN, OH, $OCH_3$, $OCF_3$, O-isopropyl, O-cyclopropyl, O-phenyl, $CH_3$, $CF_3$, and $CH_2N(CH_3)_2$; and —($C_{0-3}$ alkyl)(3-6 membered heterocyclyl) selected from piperazinyl, morpholino, $CH_2$-aziridyl, $CH_2$-pyrrolidyl, $CH_2$-piperazinyl, $CH_2$-morpholinyl, $CH_2$(2-oxa-6-azaspiro[3.3]heptyl), wherein the —($C_{0-3}$ alkyl)(3-6 membered heterocyclyl) is optionally substituted with one or more F, or $CH_3$. In some such embodiments, $R^2$ is phenyl. In still other embodiments of compounds of formula (I)—(XI), $R^2$ is 5-10-membered heteroaryl, unsubstituted or substituted with one or more substituents independently selected from F, Cl, $OCH_3$, $CH_3$, $CF_3$, and $CH_2N(CH_3)_2$. In some such embodiments, $R^2$ is pyrazolyl, pyridyl, pyrazinyl, or pyrimidyl.

In some embodiments of compounds of formula (I)—(XI), $R^4$ is F or Cl.

In some embodiments of compounds of formula (I)—(XI), n is 0, 1 or 2.

In some embodiments of compounds of formula (I)—(XI), $R^1$ is methyl, ethyl, n-propyl, isopropyl, $CH_2F$, $CHF_2$, $CF_3$, $CH_2CH_2F$, $CH_2CF_2$, $CH_2CF_3$, $CHFCH_3$, $CF_2CH_3$, or $CF_2CF_3$, and $R^2$ is $C_{1-6}$ alkyl, unsubstituted or substituted with one or more substituents independently selected from halogen, CN, and OR'; $C_{3-10}$ cycloalkyl, unsubstituted, or substituted with one or more substitutents independently selected from halogen, OR', and substituted or unsubstituted $C_{1-3}$ alkyl; 3-6-membered heterocyclyl, unsubstituted, or substituted with one or more substituted or unsubstituted $C_{1-3}$ alkyl; $C_{6-10}$ aryl, unsubstituted or substituted with one or more substituents independently selected from halogen, CN, OR', substituted or unsubstituted $C_{1-3}$ alkyl, and substituted or unsubstituted —($C_{0-3}$ alkyl)(3-6 membered heterocyclyl); or 5-10-membered heteroaryl unsubstituted or substituted with one or more substituents independently selected from halogen, OR', and substituted or unsubstituted $C_{1-3}$ alkyl; wherein each R' is independently selected from H, substituted or unsubstituted $C_{1-3}$ alkyl, substituted or unsubstituted $C_{3-6}$ cycloalkyl, and phenyl. In other embodiments of compounds of formula (I)—(XI), $R^1$ is methyl, ethyl, isopropyl, $CHF_2$, $CF_3$, $CH_2CF_3$, or $CF_2CH_3$, and $R^2$ is $C_{1-6}$ alkyl, unsubstituted or substituted with one or more substituents independently selected from F, CN, and OH. In some such embodiments, $R^2$ is $CH_3$, isopropyl, ter-butyl, $C(CH_3)_2CH_2OH$, $C(CH_3)_2CN$, or $C(CH_3)_2CF_3$. In some other embodiments of compounds of formula (I)—(XI), $R^1$ is methyl, ethyl, isopropyl, $CHF_2$, $CF_3$, $CH_2CF_3$, or $CF_2CH_3$, and $R^2$ is $C_{3-10}$ cycloalkyl, unsubstituted, or substituted with one or more substituents independently selected from F, OH, $CH_3$, $C(CH_3)_2OH$, and $CF_3$. In some such embodiments, $R^2$ is cyclopropyl, cyclobutyl, cyclopentyl, cyclohexyl, spiro[3.5]nonyl, bicyclo[1.1.1]pentyl, or spiro[2.5]octyl. In other embodiments of compounds of formula (I)—(XI), $R^1$ is methyl, ethyl, isopropyl, $CHF_2$, $CF_3$, $CH_2CF_3$, or $CF_2CH_3$, and $R^2$ is 3-6-membered heterocyclyl, unsubstituted, or substituted with one or more $CH_3$, and $CH_2CF_3$. In some such embodiments, $R^2$ is oxetanyl, tetrahydropyranyl or piperidyl. In still other embodiments of compounds of formula (I)—(XI), $R^1$ is methyl, ethyl, isopropyl, $CHF_2$, $CF_3$, $CH_2CF_3$, or $CF_2CH_3$, and $R^2$ is $C_{6-10}$ aryl, unsubstituted or substituted with one or more substituents independently selected from F, Cl, CN, OH, $OCH_3$, $OCF_3$, O-isopropyl, O-cyclopropyl, O-phenyl, $CH_3$, $CF_3$, and $CH_2N(CH_3)_2$; and —($C_{0-3}$ alkyl)(3-6 membered heterocyclyl) selected from piperazinyl, morpholino, $CH_2$-aziridyl, $CH_2$-pyrrolidyl, $CH_2$-piperazinyl, $CH_2$-morpholinyl, $CH_2$(2-oxa-6-azaspiro[3.3]heptyl), wherein the —($C_{0-3}$ alkyl)(3-6 membered heterocyclyl) is optionally substituted with one or more F, or $CH_3$. In some such embodiments, $R^2$ is phenyl. In yet other embodiments of compounds of formula (I)—(XI), $R^1$ is methyl, ethyl, isopropyl, $CHF_2$, $CF_3$, $CH_2CF_3$, or $CF_2CH_3$, and $R^2$ is 5-10-membered heteroaryl, unsubstituted or substituted with one or more substituents independently selected from F, Cl, $OCH_3$, $CH_3$, $CF_3$, and $CH_2N(CH_3)_2$. In some such embodiments, $R^2$ is pyrazolyl, pyridyl, pyrazinyl, or pyrimidyl.

Further embodiments provided herein include combinations of one or more of the particular embodiments set forth above.

Representative compounds of formulas (I), (II), (III), (IV), (V), (VI), (VII), (VIII), (IX), (X) and (XI) are set forth in Table 1.

Isoindolinone Carboxamide Compounds set forth in Table 1 were tested in the assays described herein and were found to have activity therein. In one embodiment, the Isoindolinone Carboxamide Compound is a compound as described herein, wherein the compound at a concentration of 1 µM degrades CK1α protein, by at least about 50% or more.

Methods for Making Isoindolinone Carboxamide Compounds

The Isoindolinone Carboxamide Compounds can be made using conventional organic syntheses and commercially available starting materials. By way of example and not limitation, Isoindolinone Carboxamide Compounds of formula (I) can be prepared as outlined in Schemes 1 and 2 shown below as well as in the examples set forth herein. It should be noted that one skilled in the art would know how to modify the procedures set forth in the illustrative schemes and examples to arrive at the desired products.

Scheme 1

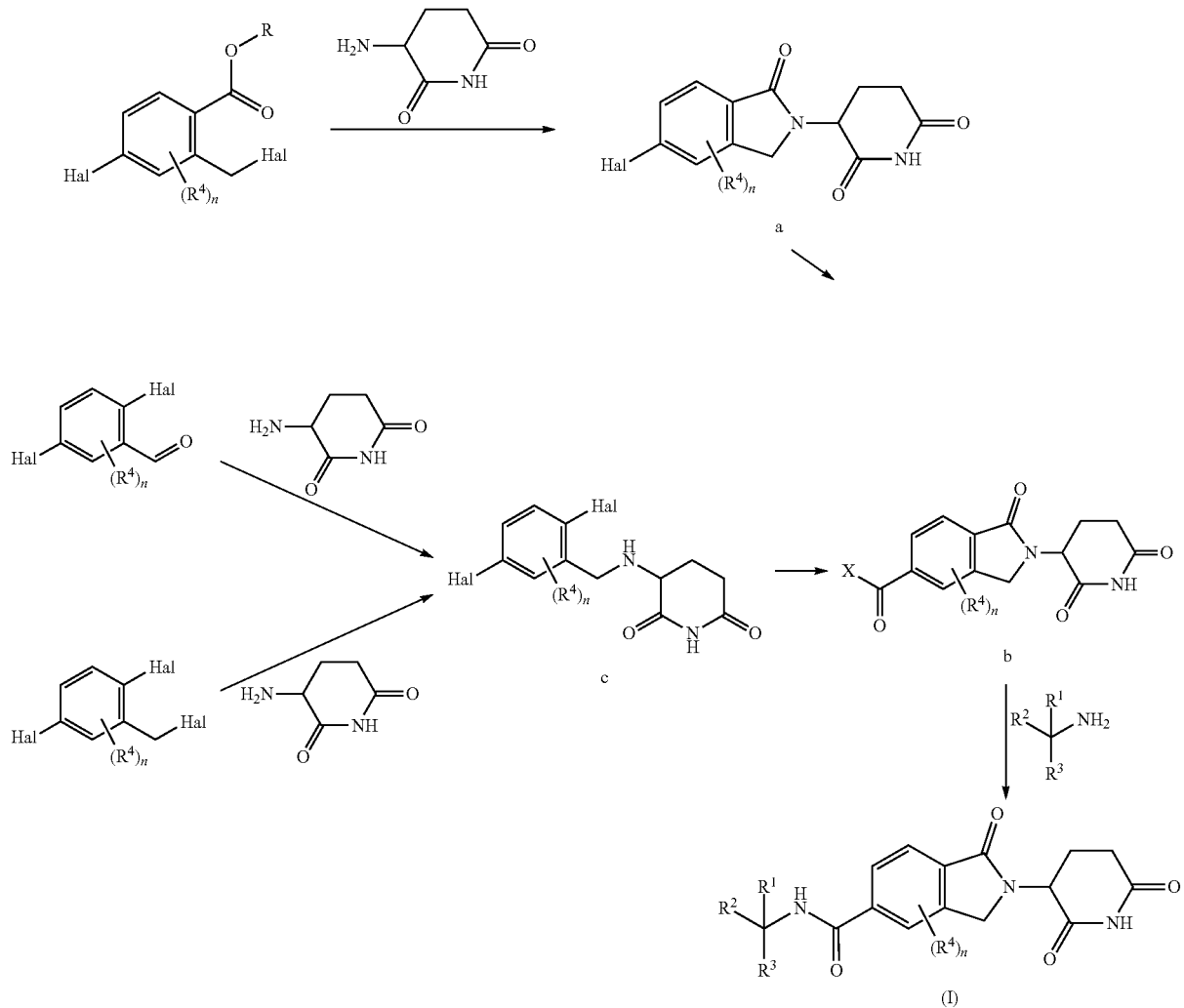

As shown in Scheme 1, the Isoindolinone Carboxamide Compounds of formula (I), wherein $R^1$, $R^2$, $R^3$, $R^4$ and n are as defined herein, can be obtained by reacting an appropriately derivatized alkyl benzoate, wherein Hal is Br or I, and R is $C_{1-3}$ alkyl, with 3-aminopiperidine-2,6-dione in a solvent, such as ACN, THF, DCM, DMF, DMA, or NMP, in the presence of a base, such as DIPEA, TEA or NMM, at a temperature between room temperature and about 80° C., to obtain the halogenated 3-(1-oxoisoindolin-2-yl)piperidine-2,6-dione intermediate a. Carbonylation of intermediate a by treatment with carbon monoxide and water, in the presence of 1,3-bis(diphenylphosphino)propane and a palladium catalyst, such as palladium acetate, in a solvent, such as DMF, DMA or NMP, in the presence of a base, such as DIPEA, TEA or NMM, at a temperature between room temperature and about 80° C., provides the derivatized 2-(2,6-dioxopiperidin-3-yl)-1-oxoisoindoline-5-carboxylic acid b, wherein X is OH. Intermediates b can also be obtained by reductive amination of appropriately derivatized benzyl aldehydes (wherein Hal is Br or I) with 3-aminopiperidine-2,6-dione, in the presence of a reducing agent, such as 2-MePyBH$_3$, NaBH$_4$, NaBH$_3$CN, (CH$_3$COO)$_3$BHNa, or decaborane, in a solvent, such as ACN, MeOH, or EtOH, in the presence of an acid, such as acetic acid or sodium acetate, to provide intermediate c. Intermediate c is then treated with carbon monoxide and water, in the presence of 1,3-bis(diphenylphosphino)propane and a palladium catalyst, such as palladium acetate, in a solvent, such as DMF, DMA or NMP, in the presence of a base, such as DIPEA, TEA or NMM, at a temperature between room temperature and about 80° C., to provide intermediate b. In an alternative approach, intermediate c can also be obtained by treatment of an appropriately derivatized benzyl halide (wherein Hal is Br or I) with 3-aminopiperidine-2,6-dione, in a solvent, such as ACN, THF, DCM, DMF, DMA, or NMP, in the presence of a base, such as DIPEA, TEA or NMM, at a temperature between room temperature and about 80° C.

Coupling of the carboxylic acid b with an amine $NH_2$ ($CR^1R^2R^3$), in a solvent, such as DMF, DMA, DCM, THF, or NMP, in the presence of a coupling agent, such as HOBT, EDCI, HATU, or T3P, and a base, such as DIPEA, TEA, or NMM, at a temperature between room temperature and about 50° C., provides compounds of formula (I), wherein $R^1$, $R^2$, $R^3$, $R^4$ and n are as defined herein.

Scheme 2

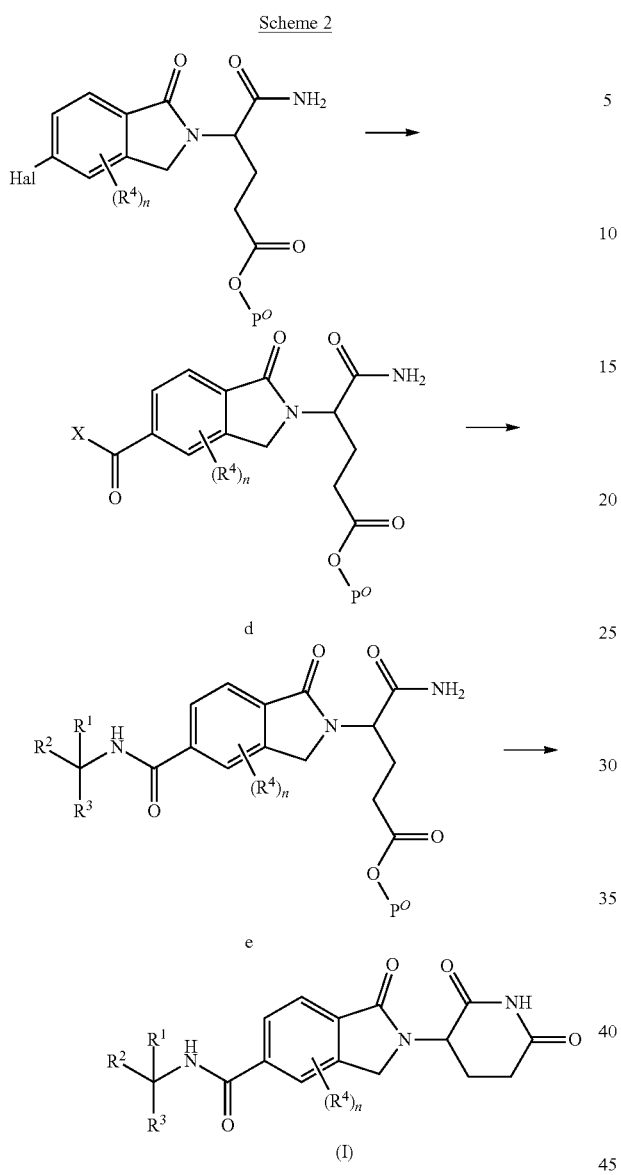

An alternative synthesis to compounds of formula (I), wherein $R^1$, $R^2$, $R^3$, $R^4$ and n are as defined herein, is shown in Scheme 2. Appropriately derivatized, carboxyl protected 5-amino-5-oxo-4-(1-oxoisoindolin-2-yl)pentanoic acid (wherein Hal is Br or I and $P^O$ is a carboxyl protecting group, such as tert-butyl) is carbonylated by treatment with carbon monoxide and water, in the presence of dicyclohexyl (3-dicyclohexylphosphaniumylpropyl) phosphonium ditetrafluoroborate and a palladium catalyst, for example, palladium acetate, in a solvent, such as DMF, DMA, or NMP, in the presence of a base, such as DIPEA, TEA, NMM, $K_2CO_3$, or $Na_2CO_3$, at a temperature between room temperature and about 80° C., to provide intermediate d, wherein X is OH. Coupling of intermediate d with an amine $NH_2(CR^1R^2R^3)$, in a solvent, such as DMF, DMA, DCM, THF, or NMP, in the presence of a coupling agent, such as HOBT, EDCI, HATU, or T3P, and a base, such as DIPEA, TEA, or NMM, at a temperature between room temperature and about 50° C., provides the carboxyl protected intermediate e. Deprotection and cyclization is achieved by treatment of intermediate e with an acid, such as benzenesulfonic acid, methanesulfonic acid, or p-toluenesulfonic acid, in a solvent, such as ACN, THF, DMF, DMA, or NMP, at a temperature between room temperature and about 80° C., to provide compounds of formula (I), wherein $R^1$, $R^2$, $R^3$, $R^4$ and n are as defined herein.

In some embodiments, chiral separation (by standard methods and as described herein) of mixtures of diastereomers of compounds of formula (I), prepared as described above, can be used to provide compounds of formulas (II)-(IX). Alternatively, the methods described in Scheme 2 can be used starting from the appropriately derivatized chiral starting materials (R)-2-(1-amino-4-carboxy-1-oxobutan-2-yl)-1-oxoisoindoline-5-carboxylic acid or (S)-2-(1-amino-4-carboxy-1-oxobutan-2-yl)-1-oxoisoindoline-5-carboxylic acid, to provide compounds of formulas (II), (III) and (VI)-(IX).

The term "protected" with respect to functional groups, refers to forms of these functionalities which are protected from undesirable reaction with a protecting group known to those skilled in the art, such as those set forth in Protective Groups in Organic Synthesis, Greene, T. W.; Wuts, P. G. M., John Wiley & Sons, New York, N.Y., ($5^{th}$ Edition, 2014), which can be added or removed using the procedures set forth therein. Examples of protecting groups for carboxyl groups as used herein include a tert-butyl protecting group.

In one aspect, provided herein are methods for preparing a compound of formula (I):

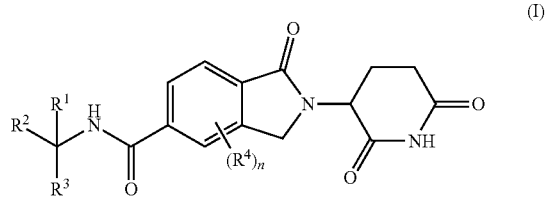

(I)

the methods comprising contacting a compound of formula b

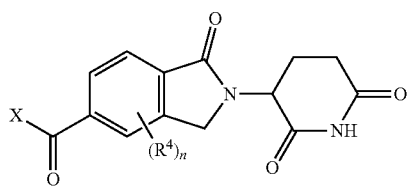

b wherein X is OH, with $NH_2(CR^1R^2R^3)$, in a solvent, in the presence of a coupling agent, and a base, under conditions suitable to provide a compound of formula (I), wherein $R^1$ is $C_{1-3}$ alkyl, or $C_{1-3}$ fluoroalkyl;
$R^2$ is substituted or unsubstituted $C_{1-6}$ alkyl, substituted or unsubstituted $C_{3-10}$ cycloalkyl, substituted or unsubstituted 3-6-membered heterocyclyl, substituted or unsubstituted $C_{6-10}$ aryl, or substituted or unsubstituted 5-10-membered heteroaryl;
$R^3$ is H;
$R^4$ is halogen; and
n is 0-3.

In one embodiment, the solvent is DMF, DMA, DCM, THF, or NMP. In another embodiment, the coupling agent is HOBT, EDCI, HATU, or T3P. In another embodiment, the base is DIPEA, TEA, or NMM. In some embodiments, the contacting is performed a temperature between room temperature and about 50° C.

In some embodiments, the methods further comprise preparing a compound of formula b

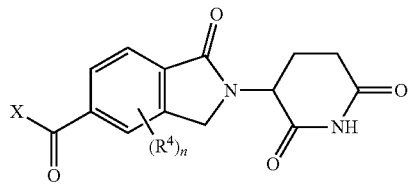

b the methods comprising contacting a compound of formula c

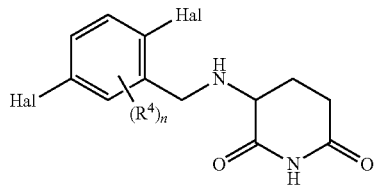

c wherein Hal is Br or I, with carbon monoxide and water, in the presence of 1,3-bis(diphenylphosphino)propane and a palladium catalyst, in a solvent, in the presence of a base, under conditions suitable to provide a compound of formula b.

In one embodiment, the palladium catalyst is palladium acetate. In one embodiment, the solvent is DMF, DMA or NMP. In another embodiment, the base is DIPEA, TEA or NMM. In some embodiments, the contacting is performed at a temperature between room temperature and about 80° C.

In some embodiments, the methods further comprise preparing a compound for formula c

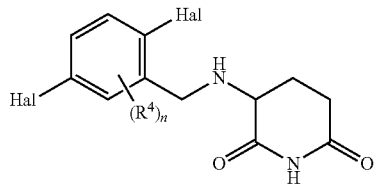

c the methods comprising contacting a benzyl halide of formula

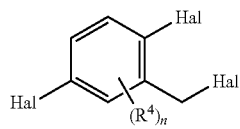

wherein Hal is Br or I, with 3-aminopiperidine-2,6-dione, in a solvent, in the presence of a base, under conditions suitable to provide a compound of formula c.

In one embodiment, the solvent is ACN, THF, DCM, DMF, DMA, or NMP. In another embodiment, the base is DIPEA, TEA or NMM. In some embodiments, the contacting is performed at a temperature between room temperature and about 80° C.

In some other embodiments, the methods further comprise preparing a compound for formula c

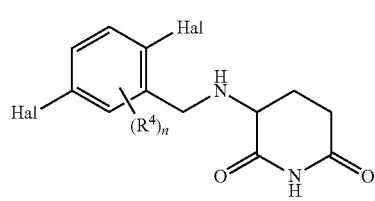

c the methods comprising contacting a benzyl aldehyde of formula

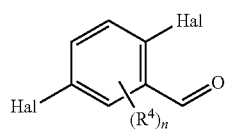

wherein Hal is Br or I, with 3-aminopiperidine-2,6-dione, in the presence of a reducing agent, in a solvent, in the presence of an acid, under conditions suitable to provide a compound of formula c.

In one embodiment, the reducing agent is 2-MePyBH$_3$, NaBH$_4$, NaBH$_3$CN, (CH$_3$COO)$_3$BHNa, or decaborane. In one embodiment, the solvent is ACN, MeOH, or EtOH. In one embodiment, the acid is acetic acid or sodium acetate.

In some embodiments, the methods further comprise preparing a compound of formula b

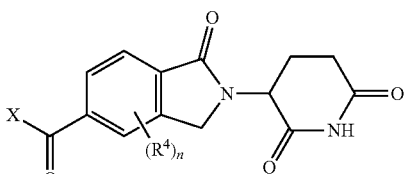

b the methods comprising contacting a compound of formula a

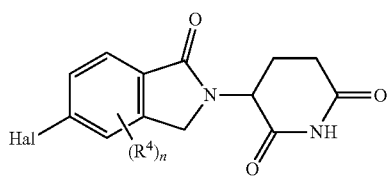

a wherein Hal is Br or I, with carbon monoxide and water, in the presence of 1,3-bis(diphenylphosphino)propane and a palladium catalyst, in a solvent, in the presence of a base, under conditions suitable to provide a compound of formula b.

In one embodiment, the palladium catalyst is palladium acetate. In one embodiment, the solvent is DMF, DMA or NMP. In another embodiment, the base is DIPEA, TEA or NMM. In some embodiments, the contacting is performed at a temperature between room temperature and about 80° C.

In some embodiments, the methods further comprise preparing a compound of formula a

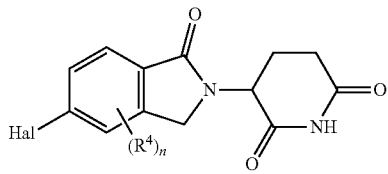

the methods comprising contacting an alkyl benzoate of formula

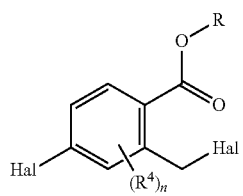

wherein Hal is Br or I and R is $C_{1-3}$ alkyl, with 3-aminopiperidine-2,6-dione in a solvent, in the presence of a base, under conditions suitable to provide a compound of formula a.

In one embodiment, the solvent is ACN, THF, DCM, DMF, DMA, or NMP. In another embodiment, the base is DIPEA, TEA or NMM. In some embodiments, the contacting is performed at a temperature between room temperature and about 80° C.

In another aspect, provided herein are methods for preparing a compound of formula (I):

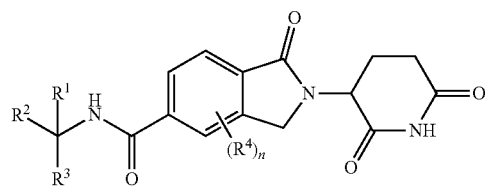

the methods comprising contacting a compound of formula e

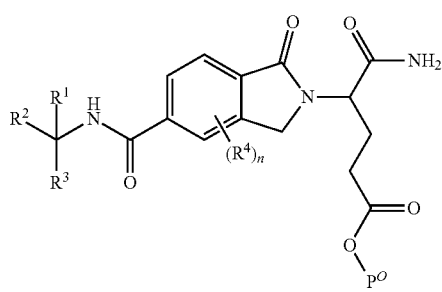

wherein $P^O$ is a carboxyl protecting group, with an acid, in a solvent, under conditions suitable to provide a compound of formula (I), wherein $R^1$ is $C_{1-3}$ alkyl, or $C_{1-3}$ fluoroalkyl;

$R^2$ is substituted or unsubstituted $C_{1-6}$ alkyl, substituted or unsubstituted $C_{3-10}$ cycloalkyl, substituted or unsubstituted 3-6-membered heterocyclyl, substituted or unsubstituted $C_{6-10}$ aryl, or substituted or unsubstituted 5-10-membered heteroaryl;

$R^3$ is H;

$R^4$ is halogen; and n is 0-3.

In one embodiment, $P^O$ is t-butyl. In one embodiment, the acid is benzenesulfonic acid, methanesulfonic acid, or p-toluenesulfonic acid. In one embodiment, the solvent is ACN, THF, DMF, DMA, or NMP. In some embodiments, the contacting is performed a temperature between room temperature and about 80° C.

In some embodiments, the methods further comprise preparing a compound of formula e

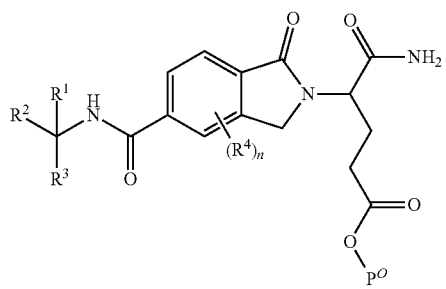

the methods comprising contacting a compound of formula d

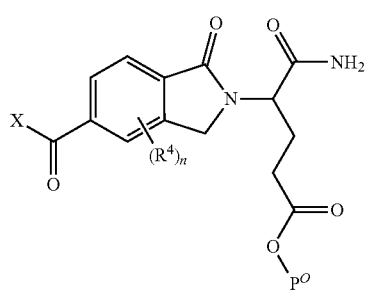

wherein X is OH, with $NH_2(CR^1R^2R^3)$, in a solvent, in the presence of a coupling agent, and a base, under conditions suitable to provide a compound of formula e.

In one embodiment, the solvent is DMF, DMA, DCM, THFW, or NMP. In another embodiment, the coupling agent is HOBT, EDCI, HATU, or T3P. In another embodiment, the base is DIPEA, TEA, or NMM. In some embodiments, the contacting is performed a temperature between room temperature and about 50° C.

In some embodiments, the methods further comprise preparing a compound of formula d

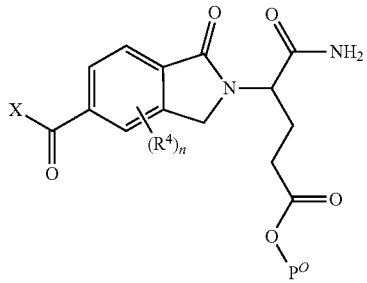

the methods comprising contacting a compound of formula

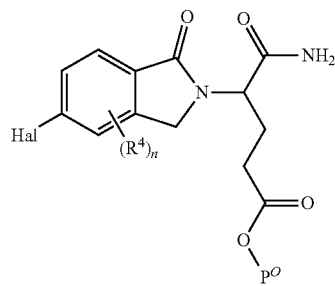

wherein Hal is Br or I, with carbon monoxide and water, in the presence of dicyclohexyl (3-dicyclohexylphosphaniumylpropyl) phosphonium ditetrafluoroborate and a palladium catalyst, in a solvent, in the presence of a base, under conditions suitable to provide a compound of formula d.

In one embodiment, the palladium catalyst is palladium acetate. In one embodiment, the solvent is DMF, DMA or NMP. In another embodiment, the base is DIPEA, TEA, NMM, $K_2CO_3$, or $Na_2CO_3$. In some embodiments, the contacting is performed at a temperature between room temperature and about 80° C.

Methods of Use and Compounds or Pharmaceutical Compositions for Use in Such Methods The Isoindolinone Carboxamide Compounds have utility as pharmaceuticals to treat, prevent or improve conditions in animals or humans. Accordingly, provided herein are the Isoindolinone Carboxamide Compounds or pharmaceutical compositions comprising the Isoindolinone Carboxamide Compounds for use as a medicament, including the treatment or prevention of those diseases set forth below. The methods provided herein comprise the administration of an effective amount of one or more Isoindolinone Carboxamide Compound(s) to a subject in need thereof.

In one aspect provided herein are methods for treating or preventing AML, comprising administering to a subject in need thereof an effective amount of an Isoindolinone Carboxamide Compound. For example, the Isoindolinone Carboxamide Compound is a compound from Table 1. Provided herein are methods for treating or preventing AML, comprising administering to a subject in need thereof an effective amount of a pharmaceutical composition as provided herein comprising the Isoindolinone Carboxamide Compound.

In another aspect provided herein are compounds for use in the treatment or prevention of AML, comprising administering to a subject in need thereof an effective amount of an Isoindolinone Carboxamide Compound. In some embodiments, provided herein are compounds for use in the treatment of AML, comprising administering to a subject in need thereof an effective amount of an Isoindolinone Carboxamide Compound as described herein. Provided herein are pharmaceutical compositions for use in methods for treating or preventing AML, comprising administering to a subject in need thereof an effective amount of a pharmaceutical composition as provided herein comprising the Isoindolinone Carboxamide Compound. Provided herein are pharmaceutical compositions for use in methods for treating AML, comprising administering to a subject in need thereof an effective amount of a pharmaceutical composition as provided herein comprising the Isoindolinone Carboxamide Compound.

In some embodiments, the AML is newly diagnosed AML. In some embodiments, the AML is primary AML. In others, the AML is relapsed AML. In still others, the AML is refractory AML. In some embodiments the AML is relapsed/refractory AML. In one embodiment, the AML is refractory to one or more of cytarabine, daunorubicin, idarubicin, midostaurin, cladribine, gemtuzumab ozogamicin, fludarabine, mitoxantrone, gilteritinib, glasdegib, and venetoclax.

In certain embodiments, the methods provided herein encompass the treatment of subjects who have not been previously treated for AML. In some embodiments, the subject has not undergone allogeneic bone marrow transplantation. In some embodiments, the subject has not undergone a stem cell transplantation. In some embodiments, the subject has not received hydroxyurea treatment. In some embodiments, the subject has not been treated with systemic glucocorticoids.

In other embodiments, the methods encompass treating subjects who have been previously treated or are currently being treated for AML. For example, the subject may have been previously treated or is currently being treated with a standard treatment regimen for AML. The subject may have been treated with any standard AML treatment regimen known to the practitioner of skill in the art. In certain embodiments, the subject has been previously treated with at least one induction/reinduction or consolidation AML regimen. In some embodiments, the subject has undergone autologous bone marrow transplantation or stem cell transplantation as part of a consolidation regimen. In some embodiments, the subject has undergone hydroxyurea treatment. In some embodiments, the subject has undergone prior induction or consolidation therapy with cytarabine (Ara-C). In some embodiments, the subject has undergone treatment with systemic glucocorticosteroids. In other embodiments, the methods encompass treating subjects who have been previously treated for AML, but are non-responsive to standard therapies.

Also encompassed are methods for treating subjects having relapsed or refractory AML. In some embodiments, the subject has been diagnosed with a relapsed or refractory AML subtype, as defined by the World Health Organization (WHO). Relapsed or refractory disease may be de novo AML or secondary AML, e.g., therapy-related AML (t-AML).

The methods for treating, preventing or managing AML in a subject comprise the step of administering to the subject an amount of an Isoindolinone Carboxamide Compound provided herein, effective to treat, prevent or manage AML alone or in combination with standard of care. In some such embodiments, the standard of care is treatment with one or more of cytarabine, daunorubicin, idarubicin, midostaurin, cladribine, gemtuzumab ozogamicin, fludarabine, mitoxantrone, gilteritinib, glasdegib, and venetoclax Provided herein are methods for reducing CK1α protein levels, the methods comprising administering to a subject an effective amount of an Isoindolinone Carboxamide Compound. Also provided herein are Isoindolinone Carboxamide Compounds for use in methods of reducing CK1α protein levels in a cell in vivo, ex vivo or in vitro, comprising contacting the cell with an effective amount of a Isoindolinone Carboxamide Compound. In one embodiment, the cell is in a patient. Provided herein are Isoindolinone Carboxamide Compounds for use in methods of reducing CK1α protein levels in a cell ex vivo or in vitro, comprising contacting the cell with an effective amount of a Isoindolinone Carboxamide Compound. In one embodiment, the cell is not in a patient. In some embodiments, the CK1α protein levels are reduced compared to the CK1α protein levels prior to the Isoindolinone Carboxamide Compound administration. In some embodiments, the CK1α protein levels are reduced by 20%, 30%, 40%, 50%, 60%, 70%, 80%, 90%, 95%, or 99% compared to the CK1α protein levels prior to the Isoindolinone Carboxamide Compound administration.

In certain embodiments of the methods provided herein, the subject is an animal, preferably a mammal, more preferably a non-human primate. In particular embodiments, the subject is a human. The subject can be a male or female subject.

Pharmaceutical Compositions and Routes of Administration

The Isoindolinone Carboxamide Compounds can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the Isoindolinone Carboxamide Compounds in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of an Isoindolinone Carboxamide Compound to be administered to a subject is rather widely variable and can be subject to the judgment of a health-care practitioner. In general, the Isoindolinone Carboxamide Compounds can be administered one to four times a day in a dose of about 0.001 mg/kg of a subject's body weight to about 10 mg/kg of a subject's body weight, but the above dosage may be properly varied depending on the age, body weight and medical condition of the subject and the type of administration. In one embodiment, the dose is about 0.001 mg/kg of a subject's body weight to about 5 mg/kg of a subject's body weight, about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, the dose is about 0.001 mg/kg of a subject's body weight to about 5 mg/kg of a subject's body weight. In one embodiment, the dose is about 0.01 mg/kg of a subject's body weight to about 5 mg/kg of a subject's body weight. In one embodiment, the dose is about 0.05 mg/kg of a subject's body weight to about 1 mg/kg of a subject's body weight. In one embodiment, the dose is about 0.1 mg/kg of a subject's body weight to about 0.75 mg/kg of a subject's body weight. In one embodiment, the dose is about 0.25 mg/kg of a subject's body weight to about 0.5 mg/kg of a subject's body weight. In one embodiment, one dose is given per day. In any given case, the amount of the Isoindolinone Carboxamide Compound administered will depend on such factors as the solubility of the active component, the formulation used and the route of administration.

In another embodiment, provided herein are methods for the treatment or prevention of a disease or disorder comprising the administration of about 0.01 mg/day to about 750 mg/day, about 0.1 mg/day to about 375 mg/day, about 0.1 mg/day to about 150 mg/day, about 0.1 mg/day to about 75 mg/day, about 0.1 mg/day to about 50 mg/day, about 0.1 mg/day to about 25 mg/day, or about 0.1 mg/day to about 10 mg/day of an Isoindolinone Carboxamide Compound to a subject in need thereof. In one embodiment, the methods for the treatment or prevention of a disease or disorder comprise the administration of about 0.01 mg/day to about 750 mg/day of an Isoindolinone Carboxamide Compound to a subject in need thereof. In one embodiment, the methods for the treatment or prevention of a disease or disorder comprise the administration of about 0.1 mg/day to about 375 mg/day of an Isoindolinone Carboxamide Compound to a subject in need thereof. In one embodiment, the methods for the treatment or prevention of a disease or disorder comprise the administration of about 0.1 mg/day to about 150 mg/day of an Isoindolinone Carboxamide Compound to a subject in need thereof. In one embodiment, the methods for the treatment or prevention of a disease or disorder comprise the administration of about 0.1 mg/day to about 75 mg/day of an Isoindolinone Carboxamide Compound to a subject in need thereof. In one embodiment, the methods for the treatment or prevention of a disease or disorder comprise the administration of about 0.1 mg/day to about 50 mg/day of an Isoindolinone Carboxamide Compound to a subject in need thereof. In one embodiment, the methods for the treatment or prevention of a disease or disorder comprise the administration of about 0.1 mg/day to about 25 mg/day of an Isoindolinone Carboxamide Compound to a subject in need thereof. In one embodiment, the methods for the treatment or prevention of a disease or disorder comprise the administration of about 0.1 mg/day to about 10 mg/day of an Isoindolinone Carboxamide Compound to a subject in need thereof.

In another embodiment, provided herein are unit dosage formulations that comprise between about 0.1 mg and 500 mg, about 1 mg and 250 mg, about 1 mg and about 100 mg, about 1 mg and about 50 mg, about 1 mg and about 25 mg, or between about 1 mg and about 10 mg of an Isoindolinone Carboxamide Compound. In one embodiment, the unit dosage formulations comprise between about 0.1 mg and 500 mg of an Isoindolinone Carboxamide Compound. In one embodiment, the unit dosage formulations comprise between about 1 mg and 250 mg of an Isoindolinone Carboxamide Compound. In one embodiment, the unit dosage formulations comprise between about 1 mg and about 100 mg of an Isoindolinone Carboxamide Compound. In one embodiment, the unit dosage formulations comprise between about 1 mg and about 50 mg of an Isoindolinone Carboxamide Compound. In one embodiment, the unit dosage formulations comprise between about 1 mg and about 25 mg of an Isoindolinone Carboxamide Compound. In one embodiment, the unit dosage formulations comprise between about 1 mg and about 10 mg of an Isoindolinone Carboxamide Compound of an Isoindolinone Carboxamide Compound.

In a particular embodiment, provided herein are unit dosage formulations comprising about 0.1 mg or 100 mg of an Isoindolinone Carboxamide Compound.

In another embodiment, provided herein are unit dosage formulations that comprise 0.5 mg, 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of an Isoindolinone Carboxamide Compound. In one embodiment, the unit dosage formulations comprise 0.5 mg of an Isoindolinone Carboxamide Compound. In one embodiment, the unit dosage formulations comprise 1 mg of an Isoindolinone Carboxamide Compound. In one embodiment, the unit dosage formulations comprise 5 mg of an Isoindolinone Carboxamide Compound. In one embodiment, the unit dosage formulations comprise 10 mg of an Isoindolinone Carboxamide Compound. In one embodiment, the unit dosage formulations comprise 15 mg of an Isoindolinone Carboxamide Compound. In one embodiment, the unit dosage formulations comprise 20 mg of an Isoindolinone Carboxamide Compound. In one embodiment, the unit dosage formulations comprise 30 mg of an Isoindolinone Carboxamide Compound. In one embodiment, the unit dosage formulations comprise 35 mg of an Isoindolinone Carboxamide Compound. In one embodiment, the unit dosage formulations comprise 50 mg of an Isoindolinone Carboxamide Compound. In one embodiment, the unit dosage formulations comprise 70 mg of an Isoindolinone Carboxamide Compound. In one embodiment, the unit dosage formulations comprise 100 mg of an Isoindolinone Carboxamide Compound. In one embodiment, the unit dosage formulations comprise 125 mg of an Isoindolinone Carboxamide Compound. In one embodiment, the unit dosage formulations comprise 140 mg of an Isoindolinone Carboxamide Compound. In one embodiment, the unit dosage formulations comprise 175 mg of an Isoindolinone Carboxamide Compound. In one embodiment, the unit dosage formulations comprise 200 mg of an Isoindolinone Carboxamide Compound. In one embodiment, the unit dosage formulations comprise 250 mg of an Isoindolinone Carboxamide Compound. In one embodiment, the unit dosage formulations comprise 280 mg of an Isoindolinone Carboxamide Compound. In one embodiment, the unit dosage formulations comprise 350 mg of an Isoindolinone Carboxamide Compound. In one embodiment, the unit dosage formulations comprise 500 mg of an Isoindolinone Carboxamide Compound. In one embodiment, the unit dosage formulations comprise 560 mg of an Isoindolinone Carboxamide Compound. In one embodiment, the unit dosage formulations comprise 700 mg of an Isoindolinone Carboxamide Compound. In one embodiment, the unit dosage formulations comprise 750 mg of an Isoindolinone Carboxamide Compound. In one embodiment, the unit dosage formulations comprise 1000 mg of an Isoindolinone Carboxamide Compound. In one embodiment, the unit dosage formulations comprise 1400 mg of an Isoindolinone Carboxamide Compound.

An Isoindolinone Carboxamide Compound can be administered once, twice, three, four or more times daily. In a particular embodiment, doses of 100 mg or less are administered as a once daily dose and doses of more than 100 mg are administered twice daily in an amount equal to one half of the total daily dose.

An Isoindolinone Carboxamide Compound can be administered orally for reasons of convenience. In one embodiment, when administered orally, an Isoindolinone Carboxamide Compound is administered with a meal and water. In another embodiment, the Isoindolinone Carboxamide Compound is dispersed in water or juice (e.g., apple juice or orange juice) and administered orally as a solution or a suspension.

The Isoindolinone Carboxamide Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing an Isoindolinone Carboxamide Compound without an additional carrier, excipient or vehicle.

In another embodiment, provided herein are compositions comprising an effective amount of an Isoindolinone Carboxamide Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing an Isoindolinone Carboxamide Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer an Isoindolinone Carboxamide Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Isoindolinone Carboxamide Compound can be delayed or prolonged by proper formulation. For example, a slowly soluble pellet of the Isoindolinone Carboxamide Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the Isoindolinone Carboxamide Compound in oily or emulsified vehicles that allow it to disperse slowly in the serum.

EXAMPLES

The following Examples are presented by way of illustration, not limitation. Compounds are named using the automatic name generating tool provided in ChemBiodraw Ultra (Cambridgesoft), which generates systematic names for chemical structures, with support for the Cahn-Ingold-Prelog rules for stereochemistry. One skilled in the art can modify the procedures set forth in the illustrative examples to arrive at the desired products.

Abbreviations used:

| Ac    | Acetyl          |
|-------|-----------------|
| ACN   | Acetonitrile    |
| nBuLi | n-Butyllithium  |
| DCM   | Dichloromethane |
| DEA   | Diethylamine    |

-continued

| DIPEA | N,N-Diisopropylethylamine |
| DMA | N,N-Dimethylacetamide |
| DMAP | 4-Dimethylaminopyridine |
| DMF | N,N-Dimethylformamide |
| DMSO | Dimethylsulfoxide |
| DSMZ | Deutsche Sammlung von Mikroorganismen und Zellkulturen GmbH |
| EDCI | 1-Ethyl-3-(3-dimethylaminopropyl)carbodiimide |
| ESI | Electrospray ionization |
| EtOH | Ethanol |
| EtOAc | Ethyl acetate |
| FBS | Fetal bovine serum |
| HATU | Hexafluorophosphate Azabenzotriazole Tetramethyl Uronium |
| HOBt | Hydroxybenzotriazole |
| HPLC | High performance liquid chromatography |
| IMDM | Iscove's Modified Dulbecco's Medium |
| LCMS | Liquid chromatography mass spectrometry |
| MeOH | Methanol |
| MEM | Minimum Essential Medium |
| 2-MePyBH$_3$ | 2-Methylpyridine borane complex |
| MS | Mass spectrometry |
| NMM | N-Methylmorpholine |
| NMP | N-Methylpyrrolidone |
| NMR | Nuclear magnetic resonance |
| SFC | Supercritical fluid chromatography |
| T3P | Propylphosphonic anhydride |
| TEA | Triethylamine |
| THF | Tetrahydrofuran |
| TLC | Thin layer chromatography |

Compound Synthesis

Example 1: 2-(2,6-Dioxopiperidin-3-yl)-1-oxo-N—((S)-1-phenylethyl)isoindoline-5-carboxamide

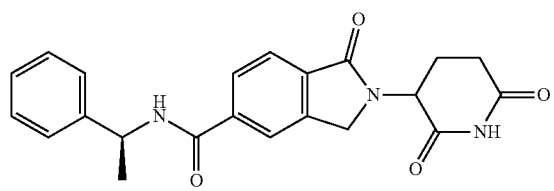 [SMILES: C[C@H](NC(=O)c1ccc2c(c1)CN(C1CCC(=O)NC1=O)C2=O)c1ccccc1]

A. 2-(2,6-Dioxopiperidin-3-yl)-1-oxo-N—((S)-1-phenylethyl)isoindoline-5-carboxamide 2-(2,6-Dioxopiperidin-3-yl)-1-oxoisoindoline-5-carboxylic acid (1.0 eq), (S)-1-phenylethanamine (1.0 eq), DIPEA (3.0 eq), and DMF (0.17 M) were stirred for 5 min. HATU (1.1 eq) was added and the resulting mixture was stirred at ambient temperature for 18 h. The reaction mixture was purified by standard methods to afford 2-(2,6-dioxopiperidin-3-yl)-1-oxo-N—((S)-1-phenylethyl)isoindoline-5-carboxamide (78.0% yield). $^1$H NMR (500 MHz, DMSO-d$_6$) δ 11.01 (s, 1H), 9.00 (d, J=7.88 Hz, 1H), 8.10 (d, J=0.63 Hz, 1H), 8.02 (dd, J=1.26, 7.88 Hz, 1H), 7.83 (d, J=7.57 Hz, 1H), 7.40-7.44 (m, 2H), 7.31-7.37 (m, 2H), 7.22-7.26 (m, 1H), 5.11-5.24 (m, 2H), 4.49-4.56 (m, 1H), 4.37-4.44 (m, 1H), 2.93 (ddd, J=5.36, 13.64, 17.58 Hz, 1H), 2.58-2.66 (m, 1H), 2.38-2.48 (m, 1H), 2.04 (dtd, J=2.05, 5.32, 12.53 Hz, 1H), 1.51 (d, J=7.25 Hz, 3H). LCMS (ESI) m/z 392.3 [M+H]$^+$.

Example 2: N—((S)-1-Cyclohexylethyl)-2-(2,6-dioxopiperidin-3-yl)-1-oxoisoindoline-5-carboxamide

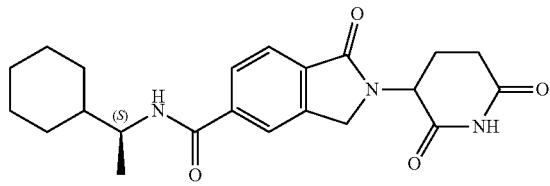

A. N—((S)-1-Cyclohexylethyl)-2-(2,6-dioxopiperidin-3-yl)-1-oxoisoindoline-5-carboxamide 2-(2,6-Dioxopiperidin-3-yl)-1-oxoisoindoline-5-carboxylic acid (1.0 eq), (S)-1-cyclohexylethan-1-amine (1.25 eq), DIPEA (3.0 eq), HOBt (1.5 eq), EDCI (1.5 eq), and DMF (1.0 M) were combined and the resulting mixture was stirred at ambient temperature for 12 h. The reaction mixture was purified by standard methods to afford N—((S)-1-cyclohexylethyl)-2-(2,6-dioxopiperidin-3-yl)-1-oxoisoindoline-5-carboxamide (71.7% yield). $^1$H NMR (400 MHz, DMSO-$d_6$) δ 11.01 (s, 1H), 8.32 (d, J=8.8 Hz, 1H), 8.04 (s, 1H), 7.96 (d, J=7.6 Hz, 1H), 7.80 (d, J=8.0 Hz, 1H), 5.14 (dd, J=5.2, 13.2 Hz, 1H), 4.52 (dd, J=2.8, 17.6 Hz, 1H), 4.40 (dd, J=2.8, 17.6 Hz, 1H), 4.92-3.82 (m, 1H), 2.96-2.87 (m, 1H), 2.65-2.57 (m, 1H), 2.45-2.36 (m, 1H), 2.07-1.98 (m, 1H), 1.82-1.67 (m, 4H), 1.65-1.57 (m, 1H), 1.44-1.39 (m, 1H), 1.18-1.11 (m, 6H), 0.97-0.94 (m, 2H). LCMS (ESI) m/z 398.1 [M+H]$^+$.

Example 3: 2-(2,6-Dioxopiperidin-3-yl)-1-oxo-N—((S)-1-phenylpropyl)isoindoline-5-carboxamide

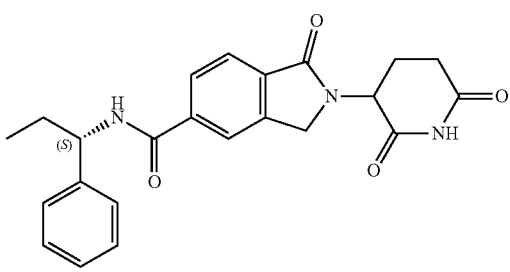

A. 2-(2,6-Dioxopiperidin-3-yl)-1-oxo-N—((S)-1-phenylpropyl)isoindoline-5-carboxamide 2-(2,6-Dioxopiperidin-3-yl)-1-oxoisoindoline-5-carboxylic acid (1.0 eq), (S)-1-phenylpropan-1-amine (1.0 eq), DIPEA (3.0 eq), HOBt (1.5 eq), EDCI (1.5 eq), and DMF (0.27 M) were combined and the resulting mixture was stirred at ambient temperature for 12 h. The reaction mixture was purified by standard methods to afford 2-(2,6-dioxopiperidin-3-yl)-1-oxo-N—((S)-1-phenylpropyl)isoindoline-5-carboxamide (59.5% yield). $^1$H NMR (400 MHz, DMSO-$d_6$) δ 10.99 (s, 1H), 8.93 (d, J=8.4 Hz, 1H), 8.07 (s, 1H), 7.99 (d, J=8.0 Hz, 1H), 7.81 (d, J=7.6 Hz, 1H), 7.40 (d, J=7.6 Hz, 2H), 7.32 (t, J=7.2 Hz, 2H), 7.22 (t, J=7.2 Hz, 1H), 5.13 (dd, J=5.2, 8.0 Hz, 1H), 4.95-4.89 (m, 1H), 4.51 (d, J=17.6 Hz, 1H), 4.39 (d, J=17.2 Hz, 1H), 2.96-2.86 (m, 1H), 2.62-2.58 (m, 1H), 2.43-2.39 (m, 1H), 2.03-2.01 (m, 1H), 1.88-1.79 (m, 2H), 0.91 (t, J=7.2 Hz, 3H). LCMS (ESI) m/z 406.2 [M+H]$^+$.

Example 4: N—((R)-1-Cyclohexylethyl)-2-(2,6-dioxopiperidin-3-yl)-1-oxoisoindoline-5-carboxamide

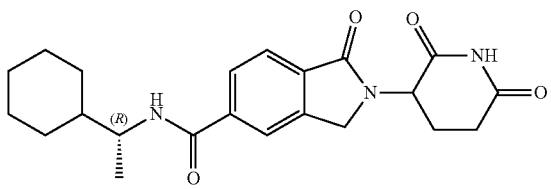

A. 2 N—((R)-1-Cyclohexylethyl)-2-(2,6-dioxopiperidin-3-yl)-1-oxoisoindoline-5-carboxamide 2-(2,6-Dioxopiperidin-3-yl)-1-oxoisoindoline-5-carboxylic acid (1.0 eq), (R)-1-cyclohexylethan-1-amine, DIPEA (3.0 eq), HOBt (1.2 eq), EDCI (1.2 eq), and DMF (0.3 M) were combined and the resulting mixture was stirred at ambient temperature for 12 h. The reaction mixture was purified by standard methods to afford N—((R)-1-cyclohexylethyl)-2-(2,6-dioxopiperidin-3-yl)-1-oxoisoindoline-5-carboxamide (50.2% yield). $^1$H NMR (400 MHz, DMSO-$d_6$) δ 11.00 (s, 1H), 8.31 (d, J=8.8 Hz, 1H), 8.04 (s, 1H), 7.96 (d, J=8.0 Hz, 1H), 7.80 (d, J=8.0 Hz, 1H), 5.14 (dd, J=6.0, 12.8 Hz, 1H), 4.57-4.45 (m, 1H), 4.44-4.32 (m, 1H), 3.92-3.79 (m, 1H), 2.97-2.87 (m, 1H), 2.61 (d, J=17.2 Hz, 1H), 2.47-2.36 (m, 1H), 2.10-1.97 (m, 1H), 1.81-1.65 (m, 4H), 1.65-1.54 (m, 1H), 1.48-1.37 (m, 1H), 1.25-1.06 (m, 6H), 1.01-0.91 (m, 2H. LCMS (ESI) m/z 398.1 [M+H]$^+$.

Example 5: N—((R)-1-Cyclohexyl-2,2,2-trifluoroethyl)-2-(2,6-dioxopiperidin-3-yl)-1-oxoisoindoline-5-carboxamide

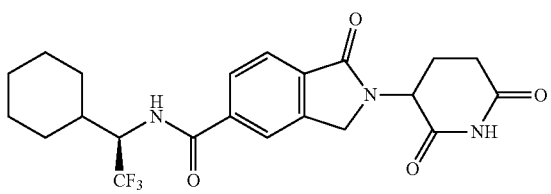

A. N—((R)-1-Cyclohexyl-2,2,2-trifluoroethyl)-2-(2,6-dioxopiperidin-3-yl)-1-oxoisoindoline-5-carboxamide 2-(2,6-Dioxopiperidin-3-yl)-1-oxoisoindoline-5-carboxylic acid (1.0 eq), (R)-1-cyclohexyl-2,2,2-trifluoroethan-1-amine hydrochloride (1.0 eq), DIPEA (4.0 eq), and DMF (0.17 M) were and stirred for 5 min. HATU (1.1 eq) was added and the resulting mixture was stirred at ambient temperature for 4 h. The reaction mixture was purified by standard methods to afford 2-(2,6-dioxopiperidin-3-yl)-1- oxo-N—((R)-2,2,2-trifluoro-1-phenylethyl)isoindoline-5-carboxamide (59.7% yield). ¹H NMR (400 MHz, DMSO-d₆) δ 10.99-11.04 (m, 1H), 8.91-8.98 (m, 1H), 8.09 (s, 1H), 7.97-8.02 (m, 1H), 7.82-7.88 (m, 1H), 5.11-5.18 (m, 1H), 4.57-4.70 (m, 1H), 4.38-4.57 (m, 2H), 2.87-2.98 (m, 1H), 2.57-2.65 (m, 1H), 2.36-2.46 (m, 1H), 1.99-2.08 (m, 1H), 1.59-1.95 (m, 6H), 1.07-1.33 (m, 5H). LCMS (ESI) m/z 452.2 [M+H]⁺.

Example 6: 2-(2,6-Dioxopiperidin-3-yl)-1-oxo-N—((R)-2,2,2-trifluoro-1-phenylethyl)isoindoline-5-carboxamide

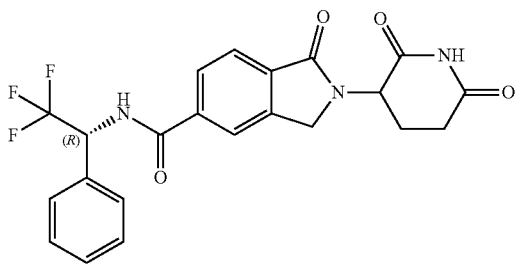

A. 2-(2,6-Dioxopiperidin-3-yl)-1-oxo-N—((R)-2,2,2-trifluoro-1-phenylethyl)isoindoline-5-carboxamide 2-(2,6-Dioxopiperidin-3-yl)-1-oxoisoindoline-5-carboxylic acid (1.0 eq), (R)-2,2,2-trifluoro-1-phenylethanamine (1.0 eq), DIPEA (3.0 eq), and DMF (0.17 M) were and stirred for 5 min. HATU (1.1 eq) was added and the resulting mixture was stirred at ambient temperature for 16 h. The reaction mixture was purified by standard methods to afford 2-(2,6-dioxopiperidin-3-yl)-1-oxo-N—((R)-2,2,2-trifluoro-1-phenylethyl)isoindoline-5-carboxamide (60.5% yield). ¹H NMR (400 MHz, DMSO-d₆) δ 10.97-11.04 (m, 1H), 9.66-9.77 (m, 1H), 8.10-8.14 (m, 1H), 7.99-8.05 (m, 1H), 7.82-7.88 (m, 1H), 7.68-7.74 (m, 2H), 7.39-7.50 (m, 3H), 6.02-6.15 (m, 1H), 5.11-5.19 (m, 1H), 4.36-4.58 (m, 2H), 2.85-2.98 (m, 1H), 2.57-2.65 (m, 1H), 2.36-2.47 (m, 1H), 1.99-2.08 (m, 1H). LCMS (ESI) m/z 446.2 [M+H]⁺.

Example 7: 2-(2,6-Dioxopiperidin-3-yl)-1-oxo-N—((S)-3,3,3-trifluoro-1-phenylpropyl)isoindoline-5-carboxamide

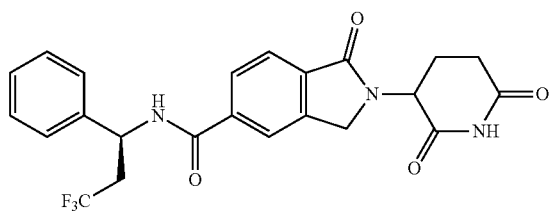 [SMILES: O=C1CCC(N2Cc3cc(C(=O)N[C@@H](CC(F)(F)F)c4ccccc4)ccc3C2=O)C(=O)N1]

A. 2-(2,6-Dioxopiperidin-3-yl)-1-oxo-N—((S)-3,3,3-trifluoro-1-phenylpropyl)isoindoline-5-carboxamide 2-(2,6-Dioxopiperidin-3-yl)-1-oxoisoindoline-5-carboxylic acid (1.0 eq), (S)-3,3,3-trifluoro-1-phenylpropan-1-amine (1.0 eq), DIPEA (3.0 eq), and DMF (0.17 M) were and stirred for 5 min. HATU (1.1 eq) was added and the resulting mixture was stirred at ambient temperature for 16 h. The reaction mixture was purified by standard methods to afford 2-(2,6-dioxopiperidin-3-yl)-1-oxo-N—((S)-3,3,3-trifluoro-1-phenylpropyl)isoindoline-5-carboxamide (44.7% yield). ¹H NMR (400 MHz, DMSO-d₆) δ 10.98-11.04 (m, 1H), 9.20-9.27 (m, 1H), 8.03-8.07 (m, 1H), 7.95-8.00 (m, 1H), 7.82-7.88 (m, 1H), 7.45-7.51 (m, 2H), 7.34-7.41 (m, 2H), 7.26-7.32 (m, 1H), 5.43-5.51 (m, 1H), 5.10-5.18 (m, 1H), 4.50-4.57 (m, 1H), 4.37-4.44 (m, 1H), 2.79-3.08 (m, 3H), 2.57-2.65 (m, 1H), 2.35-2.47 (m, 1H), 1.98-2.07 (m, 1H). LCMS (ESI) m/z 452.2 [M+H]⁺.

Example 8: 2-(2,6-Dioxopiperidin-3-yl)-1-oxo-N—((R)-2,2,2-trifluoro-1-(4-fluorophenyl)ethyl)isoindoline-5-carboxamide

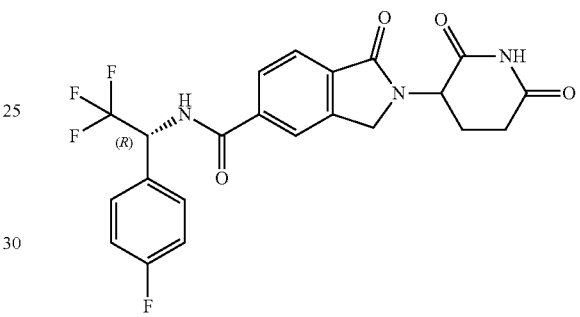

A. (S,E)-N-(4-Fluorobenzylidene)-2-methylpropane-2-sulfinamide

A mixture of 4-fluorobenzaldehyde (1.0 eq) and 2-methylpropane-2-sulfinamide (1.0 eq) in titanium tetraethanolate (2.0 eq) was stirred at 60° C. for 12 h. The mixture was diluted by EtOAc and a saturated aqueous solution of sodium chloride was added. The mixture was filtered through celite and washed with EtOAc. The combined filtrate was concentrated under reduced pressure to afford (S,E)-N-(4-fluorobenzylidene)-2-methylpropane-2-sulfinamide (quantitative yield). LCMS (ESI) m/z: 228.1 [M+H]⁺.

B. (S)-2-Methyl-N—((R)-2,2,2-trifluoro-1-(4-fluorophenyl)ethyl)propane-2-sulfinamide To a solution of (S,E)-N-(4-fluorobenzylidene)-2-methylpropane-2-sulfinamide (1.0 eq) in THF (0.3 M) at −60° C. was added tetrabutylammonium difluorotriphenylsilicate (0.2 eq). Then the mixture was stirred for 0.5 h and (trifluoromethyl)trimethylsilane (2.0 eq) was added to the solution dropwise. The mixture was stirred at −60° C. for 2.5 h and then stirred at −20° C. for 12 h. The reaction was quenched with an aqueous ammonium chloride solution and extracted with EtOAc. The organic layer was washed with brine, dried over sodium sulfate, filtered and the filtrate was concentrated. The residue was purified by column chromatography on silica gel (petroleum ether to 10:1 petroleum ether:EtOAc) to afford (S)-2-methyl-N—((R)-2,2,2-trifluoro-1-(4-fluorophenyl)ethyl)propane-2-sulfinamide (79.8% yield) as a white solid. ¹H NMR (400 MHz, CDCl₃)

δ 7.45-7.41 (m, 2H), 7.13-7.08 (m, 2H), 4.87-4.80 (m, 1H), 3.61 (d, J=6.0 Hz, 1H), 1.26 (s, 9H). LCMS (ESI) m/z: 298.1 [M+H]$^+$.

C. (R)-2,2,2-Trifluoro-1-(4-fluorophenyl)ethan-1-amine hydrochloride

To a solution of (S)-2-methyl-N—((R)-2,2,2-trifluoro-1-(4-fluorophenyl)ethyl)propane-2-sulfinamide (1.0 eq) in DCM (0.24 M) was added a 4M solution of hydrochloric acid in EtOAc (19.5 eq) at 0° C. The solution was stirred at 25° C. for 48 h. The solution was concentrated to afford (R)-2,2,2-trifluoro-1-(4-fluorophenyl)ethan-1-amine hydrochloride (97.9% yield). LCMS (ESI) m/z: 194.0 [M+H]$^+$.

D. 2-(2,6-Dioxopiperidin-3-yl)-1-oxo-N—((R)-2,2,2-trifluoro-1-(4-fluorophenyl)ethyl)isoindoline-5-carboxamide To a solution of 2-(2,6-dioxo-3-piperidyl)-1-oxo-isoindoline-5-carboxylic acid (1.0 eq) in DMF (0.73 M) was added HATU (1.2 eq), DIPEA (3.0 eq), and (R)-2,2,2-trifluoro-1-(4-fluorophenyl)ethan-1-amine hydrochloride (1.0 eq). The solution was stirred at 25° C. for 12 h. The reaction mixture was purified by standard methods to afford 2-(2,6-dioxo-3-piperidyl)-1-oxo-N—[(R)-2,2,2-trifluoro-1-(4-fluorophenyl)ethyl]isoindoline-5-carboxamide (59.1% yield). $^1$H NMR (400 MHz, DMSO-d$_6$) δ 11.03 (s, 1H), 9.72 (d, J=9.2 Hz, 1H), 8.11 (s, 1H), 8.05-8.01 (m, 1H), 7.87-7.85 (m, 1H), 7.81-7.77 (m, 2H), 7.32-7.28 (m, 2H), 6.19-6.12 (m, 1H), 5.18-5.13 (m, 1H), 4.57-4.40 (m, 2H), 2.97-2.92 (m, 1H), 2.64-2.55 (m, 1H), 2.44-2.41 (m, 1H), 2.05-2.03 (m, 1H). LCMS (ESI) m/z: 464.2 [M+H]$^+$.

Example 9: 2-(2,6-Dioxopiperidin-3-yl)-1-oxo-N—((R)-2,2,2-trifluoro-1-(pyridin-2-yl)ethyl)isoindoline-5-carboxamide

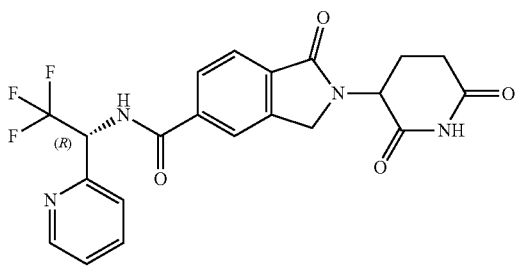

A. (S,E)-2-Methyl-N-(pyridin-2-ylmethylene)propane-2-sulfinamide

To a solution of picolinaldehyde (1.0 eq) and (S)-2-methylpropane-2-sulfinamide (1.0 eq) in DCM (0.6 M) was added Cs$_2$CO$_3$ (2.0 eq). The mixture was stirred at ambient temperature for 12 h. The mixture was filtered and concentrated under reduced pressure to afford (S,E)-2-methyl-N-(pyridin-2-ylmethylene)propane-2-sulfinamide (quantitative yield). $^1$H NMR (400 MHz, CDCl$_3$) δ (d, J=4.4 Hz, 1H), 8.69 (s, 1H), 8.01 (d, J=8.0 Hz, 1H), 7.81 (t, J=7.6 Hz, 1H), 7.42-7.35 (m, 1H), 1.27 (s, 9H). LCMS (ESI) m/z 211.0 [M+H]$^+$.

B. (S)-2-Methyl-N—((R)-2,2,2-trifluoro-1-(pyridin-2-yl)ethyl)propane-2-sulfinamide To a solution of (S,E)-2-methyl-N-(pyridin-2-ylmethylene)propane-2-sulfinamide (1.0 eq) in THF (0.19 M) was added tetrabutylammonium difluorotriphenylsilicate (0.20 eq) at −60° C. and the mixture was stirred for 0.5 h. (Trifluoromethyl)trimethylsilane (2.0 eq) was added dropwise and the mixture was stirred at −60° C. for 5 h. Then the mixture was warmed to −10° C. and was stirred for 12 h. The mixture was quenched with saturated ammonium chloride aqueous solution and extracted with EtOAc. The combined organic layers were concentrated under reduced pressure. The residue was purified by preparative TLC (50% EtOAc in petroleum ether) to afford the crude product and was then further purified by preparative HPLC (28-58% acetonitrile in water+0.05% ammonia hydroxide, over 10 min). Product containing fractions were extracted with EtOAc. The organic layer was concentrated in vacuo to afford (S)-2-methyl-N—((R)-2,2,2-trifluoro-1-(pyridin-2-yl)propane-2-sulfinamide (49.5% yield). $^1$H NMR (400 MHz, DMSO-d$_6$) δ 8.64 (d, J=4.8 Hz, 1H), 7.96-7.89 (m, 1H), 7.68 (d, J=7.6 Hz, 1H), 7.51-7.44 (m, 1H), 6.05 (d, J=7.6 Hz, 1H), 5.53-5.43 (m, 1H), 1.18 (s, 9H). LCMS (ESI) m/z: 281.1 [M+H]$^+$.

C. (R)-2,2,2-Trifluoro-1-(pyridin-2-yl)ethan-1-amine hydrochloride

To a solution of (S)-2-methyl-N—((R)-2,2,2-trifluoro-1-(pyridin-2-yl)ethyl)propane-2-sulfinamide (1.0 eq) in DCM (0.33 M) was added a 4M solution of hydrochloric acid in EtOAc (8.4 eq) at 0° C. The mixture was stirred at 15° C. for 1 h. The mixture was concentrated under reduced pressure to afford (R)-2,2,2-trifluoro-1-(pyridin-2-yl)ethan-1-amine hydrochloride (98.8% yield). LCMS (ESI) m/z: 176.0 [M+H]$^+$.

D. 2-(2,6-Dioxopiperidin-3-yl)-1-oxo-N—((R)-2,2,2-trifluoro-1-(pyridin-2-yl)ethyl)isoindoline-5-carboxamide To a solution of (R)-2,2,2-trifluoro-1-(pyridin-2-yl)ethan-1-amine hydrochloride (1.2 eq) and 2-(2,6-dioxopiperidin-3-yl)-1-oxoisoindoline-5-carboxylic acid (1.0 eq) in DMF (0.33 M) was added DIPEA (3.0 eq) and HATU (1.2 eq). The mixture was stirred at 20° C. for 12 h. The reaction mixture was purified by standard methods to afford 2-(2,6-dioxopiperidin-3-yl)-1-oxo-N—((R)-2,2,2-trifluoro-1-(pyridin-2-yl)ethyl)isoindoline-5-carboxamide (43.4% yield). $^1$H NMR (400 MHz, DMSO-d$_6$) δ 11.02 (s, 1H), 9.65 (d, J=9.2 Hz, 1H), 8.65 (d, J=4.4 Hz, 1H), 8.15 (s, 1H), 8.04 (d, J=7.6 Hz, 1H), 7.97-7.91 (m, 1H), 7.88-7.79 (m, 2H), 7.52-7.45 (m, 1H), 6.24-6.12 (m, 1H), 5.15 (dd, J=5.2, 13.2 Hz, 1H), 4.58-4.49 (m, 1H), 4.46-4.37 (m, 1H), 2.98-2.86 (m, 1H), 2.65-2.58 (m, 1H), 2.46-2.35 (m, 1H), 2.07-1.99 (m, 1H). LCMS (ESI) m/z: 447.0 [M+H]$^+$.

Example 10: 2-(2,6-Dioxopiperidin-3-yl)-1-oxo-N—((R)-2,2,2-trifluoro-1-(pyridin-3-yl)ethyl)isoindoline-5-carboxamide

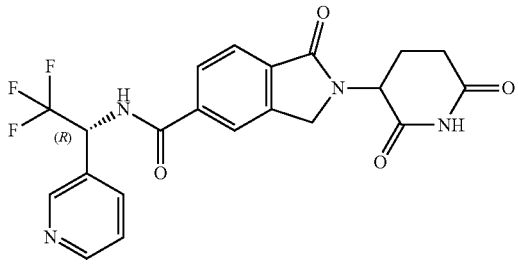

A. 2-(2,6-Dioxopiperidin-3-yl)-1-oxo-N—((R)-2,2,2-trifluoro-1-(pyridin-3-yl)ethyl)isoindoline-5-carboxamide 2-(2,6-Dioxopiperidin-3-yl)-1-oxoisoindoline-5-carboxylic acid (1.0 eq), (R)-2,2,2-trifluoro-1-(pyridin-3-yl)ethan-1-amine hydrochloride (1.2 eq), DIPEA (5.0 eq), and DMF (0.19 M) were and stirred for 5 min. HATU (1.2 eq) was added and the resulting mixture was stirred at ambient temperature for 12 h. The reaction mixture was purified by standard methods to afford 2-(2,6-dioxopiperidin-3-yl)-1-oxo-N—((R)-2,2,2-trifluoro-1-(pyridin-3-yl)ethyl)isoindoline-5-carboxamide (29.0% yield). $^1$H NMR (400 MHz, DMSO-$d_6$) δ 11.01 (s, 1H), 9.85 (dd, J=2.0 Hz, 9.6 Hz, 1H), 9.07 (d, J=2.0 Hz, 1H), 8.79 (dd, J=1.2 Hz, 4.8 Hz, 1H), 8.47 (d, J=8.0 Hz, 1H), 8.13 (s, 1H), 8.04 (d, J=8.0 Hz, 1H), 7.87 (d, J=8.0 Hz, 1H), 7.77 (dd, J=5.2 Hz, 8.0 Hz, 1H), 6.43-6.34 (m, 1H), 5.15 (dd, J=4.8 Hz, 13.2 Hz, 1H), 4.54 (dd, J=4.0 Hz, 17.6 Hz, 1H), 4.42 (d, J=17.2 Hz, 1H), 2.97-2.88 (m, 1H), 2.64-2.59 (m, 1H), 2.45-2.37 (m, 1H), 2.06-2.01 (m, 1H). LCMS (ESI) m/z 447.1 [M+H]$^+$.

Example 11 and 12: 2-((R)-2,6-Dioxopiperidin-3-yl)-1-oxo-N—((R)-2,2,2-trifluoro-1-phenylethyl)isoindoline-5-carboxamide and 2-((S)-2,6-dioxopiperidin-3-yl)-1-oxo-N—((R)-2,2,2-trifluoro-1-phenylethyl)isoindoline-5-carboxamide

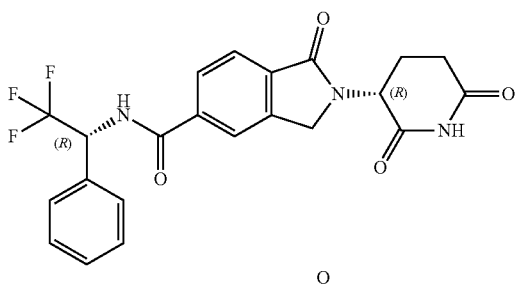

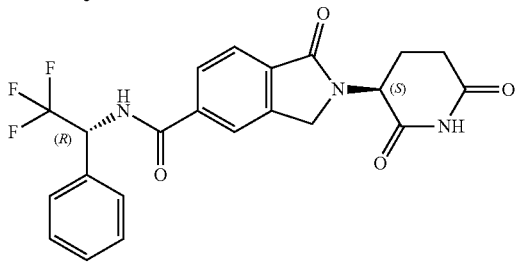

A. 2-((R)-2,6-dioxopiperidin-3-yl)-1-oxo-N—((R)-2,2,2-trifluoro-1-phenylethyl)isoindoline-5-carboxamide and 2-((S)-2,6-dioxopiperidin-3-yl)-1-oxo-N—((R)-2,2,2-trifluoro-1-phenylethyl)isoindoline-5-carboxamide 2-(2,6-Dioxopiperidin-3-yl)-1-oxo-N—((R)-2,2,2-trifluoro-1-phenylethyl)isoindoline-5-carboxamide (preparation described herein) was separated by preparative chiral SFC chromatography to provide the individual diastereomers, whose absolute stereochemistry was confirmed using vibrational circular dichroism.

2-((R)-2,6-Dioxopiperidin-3-yl)-1-oxo-N—((R)-2,2,2-trifluoro-1-phenylethyl)isoindoline-5-carboxamide was obtained in a 42.0% yield after separation. $^1$H NMR (400 MHz, DMSO-$d_6$) δ 11.02 (s, 1H), 9.73 (d, J=9.2 Hz, 1H), 8.12 (s, 1H), 8.03 (d, J=7.6 Hz, 1H), 7.86 (d, J=8.0 Hz, 1H), 7.72-7.71 (m, 2H), 7.46-7.43 (m, 3H), 6.11-6.07 (m, 1H), 5.18-5.13 (m, 1H), 4.57-4.40 (m, 2H), 2.96-2.90 (m, 1H), 2.64-2.59 (m, 1H), 2.49-2.42 (m, 1H), 2.05-2.03 (m, 1H). LCMS (ESI) m/z 446.3 [M+H]$^+$.

2-((S)-2,6-Dioxopiperidin-3-yl)-1-oxo-N—((R)-2,2,2-trifluoro-1-phenylethyl)isoindoline-5-carboxamide was obtained in a 29.0% yield after separation. $^1$H NMR (400 MHz, DMSO-$d_6$) δ 11.02 (s, 1H), 9.73 (d, J=9.2 Hz, 1H), 8.12 (s, 1H), 8.03 (d, J=8.0 Hz, 1H), 7.86 (d, J=8.0 Hz, 1H), 7.73-7.71 (m, 2H), 7.47-7.43 (m, 3H), 6.11-6.07 (m, 1H), 5.18-5.14 (m, 1H), 4.56-4.40 (m, 2H), 2.97-2.93 (m, 1H), 2.64-2.51 (m, 1H), 2.45-2.41 (m, 1H), 2.08-2.04 (m, 1H). LCMS (ESI) m/z 446.1 [M+H]$^+$.

Example 13: 2-(2,6-Dioxopiperidin-3-yl)-6-fluoro-1-oxo-N—((R)-2,2,2-trifluoro-1-phenylethyl)isoindoline-5-carboxamide

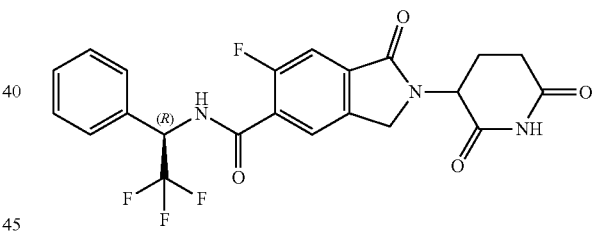

A. 3-(5-Bromo-6-fluoro-1-oxoisoindolin-2-yl)piperidine-2,6-dione

To a solution of methyl 4-bromo-2-(bromomethyl)-5-fluoro-benzoate (1.0 eq) in acetonitrile (0.13 M) was added 3-aminopiperidine-2,6-dione hydrochloride (1.0 eq), and DIPEA (2.5 eq). The solution was stirred at 80° C. for 12 h. The solution was concentrated, triturated with EtOAc, filtered, and washed with EtOAc to afford 3-(5-bromo-6-fluoro-1-oxoisoindolin-2-yl)piperidine-2,6-dione (quantitative yield). $^1$H NMR (400 MHz, CDCl$_3$) δ 9.05 (s, 1H), 8.70-8.68 (m, 1H), 7.81 (dd, J=0.8, 8.0 Hz, 1H), 7.36 (dd, J=4.4, 8.4 Hz, 1H), 1.30 (s, 9H). LCMS (ESI) m/z 340.9 [M+H]$^+$.

B. 2-(2,6-Dioxopiperidin-3-yl)-6-fluoro-1-oxoisoindoline-5-carboxylic acid

To a solution of 3-(5-bromo-6-fluoro-1-oxoisoindolin-2-yl)piperidine-2,6-dione (1.0 eq) in DMF (0.15 M) was added palladium acetate (0.5 eq), 1,3-bis(diphenylphosphino)propane (0.5 eq), DIPEA (1.0 eq) and water (10.0 eq). The mixture was stirred at 80° C. under a carbon monoxide atmosphere (50 psi) for 48 h. The reaction was filtered and the filtrate the concentrated under reduced pressure. The residue was purified by standard methods to afford 2-(2,6-dioxopiperidin-3-yl)-6-fluoro-1-oxoisoindoline-5-carboxylic acid (6.3% yield). $^1$H NMR (400 MHz, DMSO-d$_6$) δ 11.01 (s, 1H), 8.09 (d, J=6.0 Hz, 1H), 7.62 (d, J=9.2 Hz, 1H), 5.16-5.11 (m, 1H), 4.52-4.36 (m, 1H), 2.95-2.85 (m, 1H), 2.68-2.55 (m, 1H), 2.45-2.30 (m, 1H), 2.10-1.98 (m, 1H). LCMS (ESI) m/z: 307.1 [M+H]$^+$.

C. 2-(2,6-Dioxopiperidin-3-yl)-6-fluoro-1-oxo-N—((R)-2,2,2-trifluoro-1-phenylethyl)isoindoline-5-carboxamide 2-(2,6-Dioxopiperidin-3-yl)-6-fluoro-1-oxoisoindoline-5-carboxylic acid (1.0 eq), (R)-2,2,2-trifluoro-1-phenylethanamine (1.0 eq), DIPEA (3.0 eq), and DMF (0.16 M) were combined and stirred for 5 min. HATU (1.1 eq) was added and the resulting mixture was stirred at ambient temperature for 3 h. The reaction mixture was purified by standard methods to afford 2-(2,6-dioxopiperidin-3-yl)-6-fluoro-1-oxo-N—((R)-2,2,2-trifluoro-1-phenylethyl)isoindoline-5-carboxamide (61.8% yield). $^1$H NMR (400 MHz, DMSO-d$_6$) δ 10.93-11.07 (m, 1H), 9.83-9.93 (m, 1H), 7.74-7.81 (m, 1H), 7.59-7.71 (m, 3H), 7.35-7.52 (m, 3H), 5.97-6.10 (m, 1H), 5.09-5.20 (m, 1H), 4.44-4.52 (m, 1H), 4.31-4.40 (m, 1H), 2.86-2.98 (m, 1H), 2.56-2.65 (m, 1H), 2.34-2.46 (m, 1H), 1.98-2.08 (m, 1H). LCMS (ESI) m/z 464.0 [M+H]$^+$.

Example 14: 2-(2,6-Dioxopiperidin-3-yl)-4-fluoro-1-oxo-N—((R)-2,2,2-trifluoro-1-phenylethyl)isoindoline-5-carboxamide

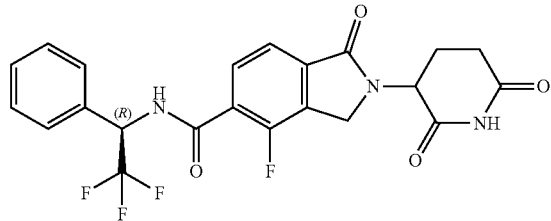

A. 3-((3,6-Dibromo-2-fluorobenzyl)amino)piperidine-2,6-dione

To a solution of 3,6-dibromo-2-fluorobenzaldehyde (1.0 eq) in acetonitrile (0.21 M) was added 3-aminopiperidine-2,6-dione hydrochloride (1.5 eq), and sodium acetate (1.5 eq). 2-Methylpyridine borane complex (2.0 eq) was added and the solution was stirred at ambient temperature for 12 h. The solution was concentrated, dissolved in EtOAc, washed with water and the organic layer was concentrated. The residue was purified by standard methods to afford 3-((3,6-dibromo-2-fluorobenzyl)amino)piperidine-2,6-dione (71.5% yield). $^1$H NMR (400 MHz, CDCl$_3$) δ 8.03-7.89 (m, 1H), 7.42-7.38 (m, 1H), 7.32-7.30 (m, 1H), 4.17-4.10 (m, 2H), 3.36-3.32 (m, 1H), 2.98-2.83 (m, 1H), 2.63-2.59 (m, 1H), 2.41-2.40 (m, 1H), 2.07-1.96 (m, 1H). LCMS (ESI) m/z 394.8 [M+H]$^+$.

B. 2-(2,6-Dioxopiperidin-3-yl)-4-fluoro-1-oxoisoindoline-5-carboxylic acid

To a solution of 3-((3,6-dibromo-2-fluorobenzyl)amino)piperidine-2,6-dione (1.0 eq) in DMF (0.19 M) was added 1,3-bis(diphenylphosphino)propane (0.1 eq), palladium acetate (0.1 eq), DIPEA (5.0 eq), and water (3.0 eq). The solution was stirred at 80° C. for 12 h under a carbon monoxide atmosphere (50 psi). The solution was filtered, washed with DMF and concentrated under reduced pressure to provide a residue. The residue was purified by standard methods to afford 2-(2,6-dioxopiperidin-3-yl)-4-fluoro-1-oxoisoindoline-5-carboxylic acid (60.8% yield). $^1$H NMR (400 MHz, DMSO-d$_6$) δ 11.04 (s, 1H), 8.04-8.00 (m, 1H), 7.68-7.66 (m, 1H), 5.17-5.13 (m, 1H), 4.65-4.44 (m, 1H), 2.95-2.92 (m, 1H), 2.63-2.53 (m, 1H), 2.48-2.44 (m, 1H), 2.05-2.03 (m, 1H). LCMS (ESI) m/z: 329.1 [M+H]$^+$.

C. 2-(2,6-Dioxopiperidin-3-yl)-4-fluoro-1-oxo-N—((R)-2,2,2-trifluoro-1-phenylethyl)isoindoline-5-carboxamide 2-(2,6-Dioxopiperidin-3-yl)-4-fluoro-1-oxoisoindoline-5-carboxylic acid (1.0 eq), (R)-2,2,2-trifluoro-1-phenylethanamine (1.0 eq), DIPEA (3.0 eq), and DMF (0.16 M) were combined and stirred for 5 min. HATU (1.1 eq) was added and the resulting mixture was stirred at ambient temperature for 3 h. The reaction mixture was purified by standard methods to afford 2-(2,6-dioxopiperidin-3-yl)-4-fluoro-1-oxo-N—((R)-2,2,2-trifluoro-1-phenylethyl)isoindoline-5-carboxamide (49.8% yield). $^1$H NMR (400 MHz, DMSO-d$_6$) δ ppm 10.99-11.06 (m, 1H), 9.83-9.92 (m, 1H), 7.61-7.72 (m, 4H), 7.40-7.50 (m, 3H), 5.97-6.09 (m, 1H), 5.10-5.20 (m, 1H), 4.58-4.65 (m, 1H), 4.41-4.49 (m, 1H), 2.87-2.98 (m, 1H), 2.57-2.65 (m, 1H), 2.39-2.48 (m, 1H), 1.99-2.09 (m, 1H). LCMS (ESI) m/z 464.2 [M+H]$^+$.

Example 15 and 16: 2-((S)-2,6-Dioxopiperidin-3-yl)-1-oxo-N—((R)-2,2,2-trifluoro-1-(4-fluorophenyl)ethyl)isoindoline-5-carboxamide and 2-((R)-2,6-dioxopiperidin-3-yl)-1-oxo-N—((R)-2,2,2-trifluoro-1-(4-fluorophenyl)ethyl)isoindoline-5-carboxamide

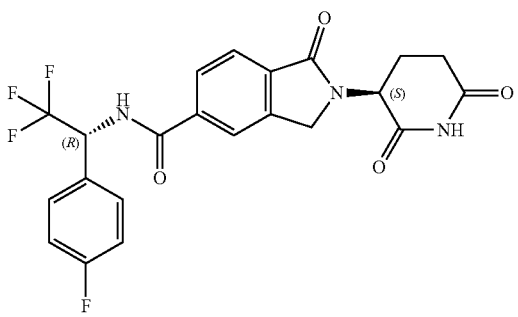

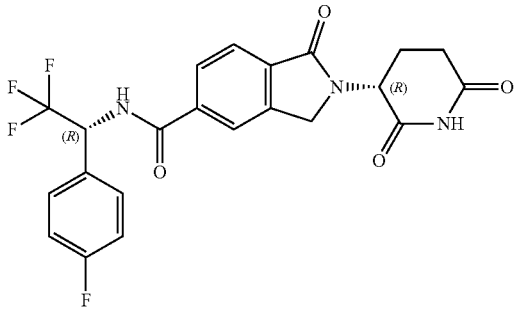

A. 2-((S)-2,6-Dioxopiperidin-3-yl)-1-oxo-N—((R)-2,2,2-trifluoro-1-(4-fluorophenyl)ethyl)isoindoline-5-carboxamide and 2-((R)-2,6-dioxopiperidin-3-yl)-1-oxo-N—((R)-2,2,2-trifluoro-1-(4-fluorophenyl)ethyl)isoindoline-5-carboxamide 2-(2,6-Dioxopiperidin-3-yl)-1-oxo-N—((R)-2,2,2-trifluoro-1-(4-fluorophenyl)ethyl)isoindoline-5-carboxamide (preparation described herein) was separated by chiral preparative SFC chromatography to provide the individual diastereomers whose absolute stereochemistry was confirmed using vibrational circular dichroism.

2-((S)-2,6-Dioxopiperidin-3-yl)-1-oxo-N—((R)-2,2,2-trifluoro-1-(4-fluorophenyl)ethyl)isoindoline-5-carboxamide was obtained in 44.0% yield after separation. $^1$H NMR (400 MHz, DMSO-d$_6$) δ 11.01 (s, 1H), 9.70 (d, J=9.6 Hz, 1H), 8.10 (s, 1H), 8.02 (d, J=8.0 Hz, 1H), 7.87-7.77 (m, 3H), 7.32-7.28 (m, 2H), 6.16-6.11 (m, 1H), 5.15 (dd, J=5.2, 13.2 Hz, 1H), 4.55-4.39 (m, 2H), 2.97-2.87 (m, 1H), 2.64-2.58 (m, 1H), 2.45-2.41 (m, 1H), 2.07-2.02 (m, 1H). LCMS (ESI) m/z 464.3 [M+H]$^+$.

2-((R)-2,6-Dioxopiperidin-3-yl)-1-oxo-N—((R)-2,2,2-trifluoro-1-(4-fluorophenyl)ethyl)isoindoline-5-carboxamide was obtained in 43.0% yield after separation. $^1$H NMR (400 MHz, DMSO-d$_6$) δ 11.01 (s, 1H), 9.70 (d, J=9.6 Hz, 1H), 8.11 (s, 1H), 8.01 (d, J=8.0 Hz, 1H), 7.87-7.77 (m, 3H), 7.32-7.28 (m, 2H), 6.16-6.11 (m, 1H), 5.15 (dd, J=5.2, 13.2 Hz, 1H), 4.56-4.39 (m, 2H), 2.96-2.88 (m, 1H), 2.63-2.59 (m, 1H), 2.45-2.41 (m, 1H), 2.07-2.03 (m, 1H). LCMS (ESI) m/z 464.4 [M+H]$^+$.

Example 17: N—((R)-1-(3-Chloropyridin-2-yl)-2,2,2-trifluoroethyl)-2-(2,6-dioxopiperidin-3-yl)-1-oxoisoindoline-5-carboxamide

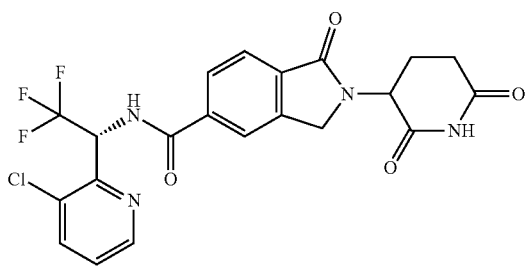 [SMILES: O=C1CCC(N2Cc3cc(C(=O)N[C@H](c4ncccc4Cl)C(F)(F)F)ccc3C2=O)C(=O)N1]

A. N—((R)-1-(3-Chloropyridin-2-yl)-2,2,2-trifluoroethyl)-2-(2,6-dioxopiperidin-3-yl)-1-oxoisoindoline-5-carboxamide To a solution of (R)-1-(3-chloropyridin-2-yl)-2,2,2-trifluoroethan-1-amine hydrochloride (preparation described herein, 1.1 eq) and 2-(2,6-dioxopiperidin-3-yl)-1-oxoisoindoline-5-carboxylic acid (1.0 eq) in DMF (0.28 M) was added DIPEA (3.0 eq) and HATU (1.2 eq). The mixture was stirred at 25° C. for 12 h. The reaction mixture was purified by standard methods to afford N—((R)-1-(3-chloropyridin-2-yl)-2,2,2-trifluoroethyl)-2-(2,6-dioxopiperidin-3-yl)-1-oxoisoindoline-5-carboxamide (52.2% yield). $^1$H NMR (400 MHz, DMSO-d$_6$) δ 11.01 (s, 1H), 9.68 (d, J=8.8 Hz, 1H), 8.67 (dd, J=0.8, 4.8 Hz, 1H), 8.14 (s, 1H), 8.10 (dd, J=1.6, 8.4 Hz, 1H), 8.04-8.00 (m, 1H), 7.81 (d, J=8.0 Hz, 1H), 7.57 (dd, J=4.4, 8.0 Hz, 1H), 6.57-6.53 (m, 1H), 5.14 (dd, J=4.8, 13.2 Hz, 1H), 4.54-4.37 (m, 2H), 2.93-2.87 (m, 1H), 2.63-2.58 (m, 1H), 2.44-2.37 (m, 1H), 2.07-1.96 (m, 1H). LCMS (ESI) m/z: 481.0 [M+H]$^+$.

Example 18: N—((R)-1-(5-Chloropyridin-2-yl)-2,2,2-trifluoroethyl)-2-(2,6-dioxopiperidin-3-yl)-1-oxoisoindoline-5-carboxamide

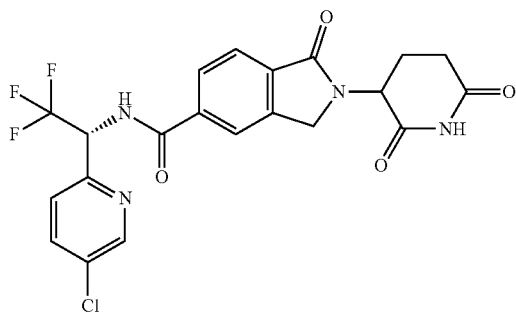 [SMILES: O=C1CCC(N2Cc3cc(C(=O)N[C@H](c4ccc(Cl)cn4)C(F)(F)F)ccc3C2=O)C(=O)N1]

A. (S,E)-N-((5-Chloropyridin-2-yl)methylene)-2-methylpropane-2-sulfinamide

To a solution of 5-chloropicolinaldehyde (1.0 eq) and (S)-2-methylpropane-2-sulfinamide (1.0 eq) in DCM (0.35 M) was added Cs$_2$CO$_3$ (2.0 eq). The mixture was stirred at 40° C. for 12 h. The mixture was filtered and concentrated under reduced pressure to afford (S,E)-N-((5-chloropyridin-2-yl)methylene)-2-methylpropane-2-sulfinamide (quantitative yield). LCMS (ESI) m/z 245.0 [M+H]$^+$.

B. (S)—N—((R)-1-(5-Chloropyridin-2-yl)-2,2,2-trifluoroethyl)-2-methylpropane-2-sulfinamide To a solution of (S,E)-N-((5-chloropyridin-2-yl)methylene)-2-methylpropane-2-sulfinamide (1.0 eq) in THF (0.33 M) was added tetrabutylammonium difluorotriphenylsilicate (0.20 eq) at −60° C. and the mixture was stirred for 0.5 h. (Trifluoromethyl)trimethylsilane (2.0 eq) was added dropwise and the mixture was stirred at −60° C. for 2.5 h. Then the mixture was warmed to −20° C. and it was stirred for 2.5 h. The mixture was quenched with saturated ammonium chloride aqueous solution and extracted with EtOAc. The combined organic layers were dried over anhydrous Na$_2$SO$_4$. The organic layer was filtered and the filtrate was concentrated under reduced pressure. The residue was purified by preparative HPLC (40-58% acetonitrile+0.2% formic acid in water, over 25 min) and product containing fractions were concentrated under reduced pressure to afford (S)—N—((R)-1-(5-chloropyridin-2-yl)-2,2,2-trifluoroethyl)-2-methylpropane-2-sulfinamide (58.3% yield). $^1$H NMR (400 MHz, CDCl$_3$) δ 8.59 (d, J=2.4 Hz, 1H), 7.76-7.73 (m, 1H), 7.38 (d, J=8.4 Hz, 1H), 5.61 (d, J=6.4 Hz, 1H), 4.96-4.89 (m, 1H), 1.33 (s, 9H). LCMS (ESI) m/z: 315.1 [M+H]$^+$.

C. (R)-1-(5-Chloropyridin-2-yl)-2,2,2-trifluoroethan-1-amine hydrochloride

To a solution of (S)—N—((R)-1-(5-chloropyridin-2-yl)-2,2,2-trifluoroethyl)-2-methylpropane-2-sulfinamide (1.0 eq) in DCM (0.18 M) was added a 4 M solution of hydrochloric acid in EtOAc (19.5 eq) at 0° C. The mixture was stirred at 25° C. for 12 h. The mixture was concentrated under reduced pressure and the residue was triturated with petroleum ether (60 mL), filtered, and dried under reduced pressure to afford (R)-1-(5-chloropyridin-2-yl)-2,2,2-trifluoroethan-1-amine hydrochloride (quantitative yield). LCMS (ESI) m/z: 211.0 [M+H]$^+$.

D. N—((R)-1-(5-Chloropyridin-2-yl)-2,2,2-trifluoroethyl)-2-(2,6-dioxopiperidin-3-yl)-1-oxoisoindoline-5-carboxamide To a solution of (R)-1-(5-chloropyridin-2-yl)-2,2,2-trifluoroethan-1-amine hydrochloride (1.1 eq) and 2-(2,6-dioxopiperidin-3-yl)-1-oxoisoindoline-5-carboxylic acid (1.0 eq) in DMF (0.30 M) was added DIPEA (3.0 eq) and HATU (1.2 eq). The mixture was stirred at 25° C. for 12 h. The reaction mixture was purified by standard methods to afford N—((R)-1-(5-chloropyridin-2-yl)-2,2,2-trifluoroethyl)-2-(2,6-dioxopiperidin-3-yl)-1-oxoisoindoline-5-carboxamide (33.5% yield). $^1$H NMR (400 MHz, DMSO-d$_6$) δ 11.03 (s, 1H), 9.72 (d, J=9.2 Hz, 1H), 8.72 (d, J=2.4 Hz, 1H), 8.14-8.11 (m, 2H), 8.10-8.05 (m, 1H), 7.87-7.84 (m, 2H), 6.25-6.20 (m, 1H), 5.17-5.13 (m, 1H), 4.56-4.39 (m, 2H), 2.93-2.92 (m, 1H), 2.63-2.52 (m, 1H), 2.45-2.42 (m, 1H), 2.07-2.04 (m, 1H). LCMS (ESI) m/z: 481.2 [M+H]$^+$.

Example 19: 2-(2,6-Dioxopiperidin-3-yl)-1-oxo-N—((R)-2,2,2-trifluoro-1-(3-fluoropyridin-2-yl)ethyl)isoindoline-5-carboxamide

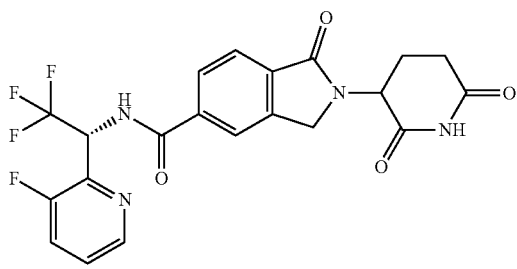 [SMILES: O=C1CCC(N2Cc3cc(C(=O)N[C@H](c4ncccc4F)C(F)(F)F)ccc3C2=O)C(=O)N1]

A. (S,E)-N-((3-Fluoropyridin-2-yl)methylene)-2-methylpropane-2-sulfinamide

To a solution of 3-fluoropicolinaldehyde (1.0 eq) and (S)-2-methylpropane-2-sulfinamide (1.2 eq) in DCM (0.53 M) was added CuSO$_4$ (2.0 eq). The mixture was stirred at ambient temperature for 3 h. The mixture was filtered and concentrated under reduced pressure to afford (S,E)-N-((3-fluoropyridin-2-yl)methylene)-2-methylpropane-2-sulfinamide (quantitative yield). $^1$H NMR (400 MHz, DMSO-d$_6$) δ 8.63 (d, J=4.4 Hz, 1H), 8.59 (s, 1H), 7.96-7.91 (m, 1H), 7.73-7.69 (m, 1H), 1.19 (s, 9H). LCMS (ESI) m/z 229.0 [M+H]$^+$.

B. (S)-2-Methyl-N—((R)-2,2,2-trifluoro-1-(3-fluoropyridin-2-yl)ethyl)propane-2-sulfinamide To a solution of (S,E)-N-((3-fluoropyridin-2-yl)methylene)-2-methylpropane-2-sulfinamide (1.0 eq) in THF (0.22 M) was added tetrabutylammonium difluorotriphenylsilicate (0.20 eq) at −60° C. and the mixture was stirred for 0.5 h. (Trifluoromethyl)trimethylsilane (2.0 eq) was added dropwise and the mixture was stirred at −60° C. for 2.5 h. Then the mixture was warmed to −20° C. and it was stirred for 11.5 h. The mixture was concentrated under reduced pressure. The residue was purified by preparative HPLC (38-68% acetonitrile+0.05% ammonia hydroxide in water, over 10 min), and product containing fractions were concentrated under reduced pressure to afford (S)-2-methyl-N—((R)-2,2,2-trifluoro-1-(3-fluoropyridin-2-yl)ethyl)propane-2-sulfinamide (18.4% yield). $^1$H NMR (400 MHz, DMSO-d$_6$) δ 8.57-8.55 (m, 1H), 7.94-7.89 (m, 1H), 7.66-7.61 (m, 1H), 6.07 (d, J=8.4 Hz, 1H), 5.59 (t, J=7.6 Hz, 1H), 1.16 (s, 9H). LCMS (ESI) m/z: 299.1 [M+H]$^+$.

C. (R)-2,2,2-Trifluoro-1-(3-fluoropyridin-2-yl)ethan-1-amine hydrochloride

To a solution of (S)-2-methyl-N—((R)-2,2,2-trifluoro-1-(3-fluoropyridin-2-yl)ethyl)propane-2-sulfinamide (1.0 eq) in DCM (0.13 M) was added a 4M solution of hydrochloric acid in EtOAc (30.0 eq). The mixture was stirred at 25° C. for 1 h. The mixture was concentrated under reduced pressure to afford (R)-2,2,2-trifluoro-1-(3-fluoropyridin-2-yl)ethan-1-amine hydrochloride (97.0% yield). LCMS (ESI) m/z: 195.0 [M+H]$^+$.

D. 2-(2,6-Dioxopiperidin-3-yl)-1-oxo-N—((R)-2,2,2-trifluoro-1-(3-fluoropyridin-2-yl)ethyl)isoindoline-5-carboxamide To a solution of (R)-2,2,2-trifluoro-1-(3-fluoropyridin-2-yl)ethan-1-amine hydrochloride (1.0 eq) and 2-(2,6-dioxopiperidin-3-yl)-1-oxoisoindoline-5-carboxylic acid (1.2 eq) in DMF (0.13 M) was added DIPEA (3.0 eq) and HATU (1.2 eq). The mixture was stirred at 25° C. for 12 h. The reaction mixture was purified by standard methods to afford 2-(2,6-dioxopiperidin-3-yl)-1-oxo-N—((R)-2,2,2-trifluoro-1-(3-fluoropyridin-2-yl)ethyl)isoindoline-5-carboxamide (31.4% yield). $^1$H NMR (400 MHz, DMSO-d$_6$) δ 11.01 (s, 1H), 9.76 (d, J=8.8 Hz, 1H), 8.56 (d, J=4.4 Hz, 1H), 8.15 (s, 1H), 8.05 (dd, J=4.0, 7.6 Hz, 1H), 7.92-7.87 (m, 1H), 7.83 (d, J=8.0 Hz, 1H), 7.64-7.61 (m, 1H), 6.45-6.37 (m, 1H), 5.16 (dd, J=5.2, 13.2 Hz, 1H), 4.54-4.37 (m, 2H), 2.96-2.86 (m, 1H), 2.62-2.58 (m, 1H), 2.44-2.38 (m, 1H), 2.04-2.00 (m, 1H). LCMS (ESI) m/z: 465.2 [M+H]$^+$.

Example 20: N—((R)-1-(5-Chloro-3-fluoropyridin-2-yl)-2,2,2-trifluoroethyl)-2-(2,6-dioxopiperidin-3-yl)-1-oxoisoindoline-5-carboxamide

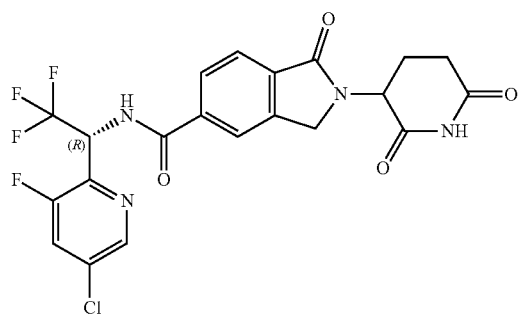

A. (S,E)-N-((5-Chloro-3-fluoropyridin-2-yl)methylene)-2-methylpropane-2-sulfinamide To a solution of 5-chloro-3-fluoropicolinaldehyde (1.0 eq) and (S)-2-methylpropane-2-sulfinamide (1.2 eq) in DCM

47

(0.5 M) was added CuSO₄ (1.5 eq). The mixture was stirred at ambient temperature for 3 h. The mixture was filtered and concentrated under reduced pressure to afford (S,E)-N-((5-chloro-3-fluoropyridin-2-yl)methylene)-2-methylpropane-2-sulfinamide (98.7% yield). LCMS (ESI) m/z 262.0 [M+H]⁺.

B. (S)—N—((R)-1-(5-Chloro-3-fluoropyridin-2-yl)-2,2,2-trifluoroethyl)-2-methylpropane-2-sulfinamide To a solution of (S,E)-N-((5-chloro-3-fluoropyridin-2-yl)methylene)-2-methylpropane-2-sulfinamide (1.0 eq) in THF (0.38 M) was added tetrabutylammonium difluorotriphenylsilicate (0.20 eq) at −78° C. and the mixture was stirred for 0.5 h. (Trifluoromethyl)trimethylsilane (3.0 eq) was added dropwise and the mixture was stirred at −10° C. for 1 h. The mixture was concentrated under reduced pressure. The residue was purified by preparative HPLC (48-78% acetonitrile+0.05% ammonia hydroxide in water, over 10 min) and product containing fractions were concentrated under reduced pressure to afford (S)—N—((R)-1-(5-chloro-3-fluoropyridin-2-yl)-2,2,2-trifluoroethyl)-2-methylpropane-2-sulfinamide (22.1% yield). ¹H NMR (400 MHz, DMSO-d₆) δ 8.66 (d, J=2.0 Hz, 1H), 8.30 (dd, J=2.0, 9.6 Hz, 1H), 6.14 (d, J=8.8 Hz, 1H), 5.61-5.58 (m, 1H), 1.13 (s, 9H). LCMS (ESI) m/z: 333.1 [M+H]⁺.

C. (R)-1-(5-Chloro-3-fluoropyridin-2-yl)-2,2,2-trifluoroethan-1-amine hydrochloride To a solution of (S)—N—((R)-1-(5-chloro-3-fluoropyridin-2-yl)-2,2,2-trifluoroethyl)-2-methylpropane-2-sulfinamide (1.0 eq) in DCM (0.28 M) was added a 4 M solution of hydrochloric acid in EtOAc (14.3 eq). The mixture was stirred at 25° C. for 1 h. The mixture was concentrated under reduced pressure to afford (R)-1-(5-chloro-3-fluoropyridin-2-yl)-2,2,2-trifluoroethan-1-amine hydrochloride (98.6% yield). LCMS (ESI) m/z: 229.0 [M+H]⁺.

D. N—((R)-1-(5-Chloro-3-fluoropyridin-2-yl)-2,2,2-trifluoroethyl)-2-(2,6-dioxopiperidin-3-yl)-1-oxoisoindoline-5-carboxamide To a solution of (R)-1-(5-chloro-3-fluoropyridin-2-yl)-2,2,2-trifluoroethan-1-amine hydrochloride (1.0 eq) and 2-(2,6-dioxopiperidin-3-yl)-1-oxoisoindoline-5-carboxylic acid (1.2 eq) in DMF (0.11 M) was added DIPEA (3.0 eq) and HATU (1.2 eq). The mixture was stirred at 25° C. for 12 h. The reaction mixture was purified by standard methods to afford N—((R)-1-(5-chloro-3-fluoropyridin-2-yl)-2,2,2-trifluoroethyl)-2-(2,6-dioxopiperidin-3-yl)-1-oxoisoindoline-5-carboxamide (63.1% yield). ¹H NMR (400 MHz, DMSO-d₆) δ 11.02 (s, 1H), 9.82 (d, J=8.8 Hz, 1H), 8.67 (s, 1H), 8.29 (dd, J=2.0, 9.6 Hz, 1H), 8.14 (s, 1H), 8.04-8.01 (m, 1H), 7.83 (d, J=8.0 Hz, 1H), 6.41 (t, J=8.0 Hz, 1H), 5.15 (dd, J=5.2, 13.2 Hz, 1H), 4.55-4.50 (m, 1H), 4.42-4.38 (m, 1H), 2.95-2.92 (m, 1H), 2.63-2.59 (m, 1H), 2.45-2.41 (m, 1H), 2.06-2.01 (m, 1H). LCMS (ESI) m/z: 499.0 [M+H]⁺.

48

Example 21: N—((R)-1-(3,5-Difluoropyridin-2-yl)-2,2,2-trifluoroethyl)-2-(2,6-dioxopiperidin-3-yl)-1-oxoisoindoline-5-carboxamide

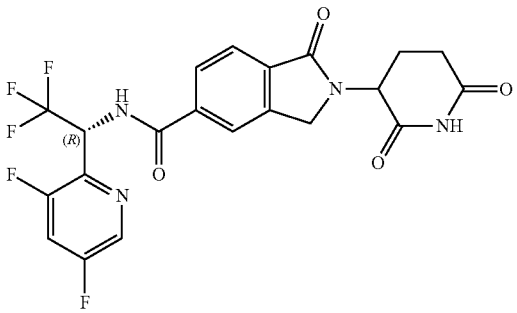

A. (S,E)-N-((3,5-Difluoropyridin-2-yl)methylene)-2-methylpropane-2-sulfinamide

To a solution of 3,5-difluoropicolinaldehyde (1.0 eq) and (S)-2-methylpropane-2-sulfinamide (1.2 eq) in DCM (0.63 M) was added CuSO₄ (1.5 eq). The mixture was stirred at ambient temperature for 23 h. The mixture was filtered and concentrated under reduced pressure to afford (S,E)-N-((3,5-difluoropyridin-2-yl)methylene)-2-methylpropane-2-sulfinamide (quantitative yield). ¹H NMR (400 MHz, CDCl₃) δ 8.85 (s, 1H), 8.53 (s, 1H), 7.37-7.27 (m, 1H), 1.31 (s, 9H). LCMS (ESI) m/z 247.0 [M+H]⁺.

B. (S)—N—((R)-1-(3,5-Difluoropyridin-2-yl)-2,2,2-trifluoroethyl)-2-methylpropane-2-sulfinamide To a solution of (S,E)-N-((3,5-difluoropyridin-2-yl)methylene)-2-methylpropane-2-sulfinamide (1.0 eq) in THF (0.29 M) was added tetrabutylammonium difluorotriphenylsilicate (0.20 eq) at −70° C. and the mixture was stirred for 0.5 h. (Trifluoromethyl)trimethylsilane (3.0 eq) was added dropwise and the mixture was stirred at −70° C. for 4 h. The mixture was warmed to −10° C. and it was stirred for 12 h, then quenched with saturated ammonium chloride aqueous solution, and extracted with EtOAc. The combined organic layer was dried over anhydrous sodium sulfate. The organic layer was filtered and the filtrate was concentrated in vacuo. The residue was purified by silica column chromatography on silica gel (9%-33% of EtOAc in petroleum ether). The residue was purified by preparative HPLC (38-68% acetonitrile+0.225% formic acid in water, over 10 min) and product containing fractions were concentrated under reduced pressure to afford (S)—N—((R)-1-(3,5-difluoropyridin-2-yl)-2,2,2-trifluoroethyl)-2-methylpropane-2-sulfinamide (6.8% yield). ¹H NMR (400 MHz, CDCl₃) δ 8.39 (d, J=2.0 Hz, 1H), 7.33-7.29 (m, 1H), 5.34-5.31 (m, 1H), 5.23 (t, J=6.4 Hz, 1H), 1.32 (s, 9H). LCMS (ESI) m/z: 316.9 [M+H]⁺.

C. (R)-1-(3,5-Difluoropyridin-2-yl)-2,2,2-trifluoroethan-1-amine hydrochloride

To a solution of (S)—N—((R)-1-(3,5-difluoropyridin-2-yl)-2,2,2-trifluoroethyl)-2-methylpropane-2-sulfinamide (1.0 eq) in DCM (0.14 M) was added a 4 M solution of hydrochloric acid in EtOAc (30.0 eq). The mixture was stirred at 25° C. for 1 h. The mixture was concentrated under reduced pressure to afford (R)-1-(3,5-difluoropyridin-2-yl)-

2,2,2-trifluoroethan-1-amine hydrochloride (quantitative yield). LCMS (ESI) m/z: 212.9 [M+H]⁺.

D. N—((R)-1-(3,5-Difluoropyridin-2-yl)-2,2,2-trifluoroethyl)-2-(2,6-dioxopiperidin-3-yl)-1-oxoisoindoline-5-carboxamide To a solution of (R)-1-(3,5-difluoropyridin-2-yl)-2,2,2-trifluoroethan-1-amine hydrochloride (1.0 eq) and 2-(2,6-dioxopiperidin-3-yl)-1-oxoisoindoline-5-carboxylic acid (1.0 eq) in DMF (0.35 M) was added DIPEA (3.0 eq) and HATU (1.5 eq). The mixture was stirred at 25° C. for 12 h. The reaction mixture was purified by standard methods to afford N—((R)-1-(3,5-difluoropyridin-2-yl)-2,2,2-trifluoroethyl)-2-(2,6-dioxopiperidin-3-yl)-1-oxoisoindoline-5-carboxamide (64.9% yield). ¹H NMR (400 MHz, DMSO-d₆) δ 11.00 (s, 1H), 9.79 (d, J=8.8 Hz, 1H), 8.66 (d, J=2.0 Hz, 1H), 8.16-8.11 (m, 2H), 8.05-8.01 (m, 1H), 7.82 (d, J=8.0 Hz, 1H), 6.40 (t, J=8.4 Hz, 1H), 5.14 (dd, J=5.2, 13.6 Hz, 1H), 4.55-4.38 (m, 2H), 2.92-2.89 (m, 1H), 2.63-2.59 (m, 1H), 2.45-2.37 (m, 1H), 2.06-1.97 (m, 1H). LCMS (ESI) m/z: 483.2 [M+H]⁺.

Example 22: 4-Chloro-2-(2,6-dioxopiperidin-3-yl)-1-oxo-N—((R)-2,2,2-trifluoro-1-(4-fluorophenyl)ethyl)isoindoline-5-carboxamide

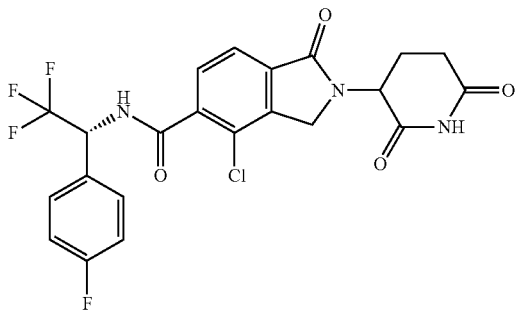 [SMILES: O=C1CCC(N2Cc3c(ccc(C(=O)N[C@H](c4ccc(F)cc4)C(F)(F)F)c3Cl)C2=O)C(=O)N1]

A. 3-((3,6-Dibromo-2-chlorobenzyl)amino)piperidine-2,6-dione

To a solution of 1,4-dibromo-2-(bromomethyl)-3-chlorobenzene (1.0 eq) and 3-aminopiperidine-2,6-dione hydrochloride (3.0 eq.) in acetonitrile (0.28 M) was added DIPEA (5.0 eq). The mixture was stirred at 60° C. for 12 h. The mixture was concentrated. The residue was purified by silica gel column chromatography (9%-33% of EtOAc in petroleum ether) to afford 3-((3,6-dibromo-2-chlorobenzyl)amino)piperidine-2,6-dione (69.5% yield). ¹H NMR (400 MHz, DMSO-d₆) δ 10.79 (s, 1H), 7.65-7.55 (m, 2H), 4.20-4.07 (m, 2H), 3.38 (dd, J=3.6, 11.2 Hz, 1H), 2.58-2.50 (m, 2H), 2.23-2.19 (m, 1H), 1.82-1.72 (m, 1H). LCMS (ESI) m/z 410.7 [M+H]⁺.

B. 4-Chloro-2-(2,6-dioxopiperidin-3-yl)-1-oxoisoindoline-5-carboxylic acid

To a solution of 3-((3,6-dibromo-2-chlorobenzyl)amino) piperidine-2,6-dione (1.0 eq) in DMF (0.22 M) was added palladium acetate (0.1 eq), 1,3-bis(diphenylphosphino)propane (0.1 eq), DIPEA (5.0 eq) and water (3.0 eq). The mixture was stirred at 80° C. for 60 h under a carbon monoxide atmosphere (50 psi). The mixture was filtered and the filtrate was concentrated. The residue was purified by preparative HPLC (1-30% acetonitrile+0.2% formic acid in water, over 30 min) to afford 4-chloro-2-(2,6-dioxopiperidin-3-yl)-1-oxoisoindoline-5-carboxylic acid (35.7% yield). ¹H NMR (400 MHz, DMSO-d₆) δ 11.03 (s, 1H), 7.94 (d, J=8.0 Hz, 1H), 7.79-7.77 (m, 1H), 5.15 (dd, J=4.8, 13.2 Hz, 1H), 4.56-4.35 (m, 2H), 2.96-2.87 (m, 1H), 2.61 (d, J=17.2 Hz, 1H), 2.46-2.45 (m, 1H), 2.07-2.02 (m, 1H). LCMS (ESI) m/z: 322.8 [M+H]⁺.

C. 4-Chloro-2-(2,6-dioxopiperidin-3-yl)-1-oxo-N—((R)-2,2,2-trifluoro-1-(4-fluorophenyl)ethyl)isoindoline-5-carboxamide 4-Chloro-2-(2,6-dioxo-3-piperidyl)-1-oxo-isoindoline-5-carboxylic acid (1.0 eq), (R)-2,2,2-trifluoro-1-(4-fluorophenyl)ethanamine hydrochloride (1.0 eq), and DIPEA (4.0 eq) were combined in DMF (0.16 M). To this solution was added HATU (1.1 eq) and the resulting mixture was stirred at ambient temperature for 16 h. The reaction mixture was purified by standard methods to afford 4-chloro-2-(2,6-dioxopiperidin-3-yl)-1-oxo-N—((R)-2,2,2-trifluoro-1-(4-fluorophenyl)ethyl)isoindoline-5-carboxamide (53.6% yield). ¹H NMR (400 MHz, DMSO-d₆) δ 10.98-11.06 (m, 1H), 9.88-9.97 (m, 1H), 7.77-7.84 (m, 1H), 7.66-7.76 (m, 2H), 7.55-7.62 (m, 1H), 7.25-7.37 (m, 2H), 6.03-6.16 (m, 1H), 5.12-5.22 (m, 1H), 4.50-4.59 (m, 1H), 4.32-4.43 (m, 1H), 2.86-2.98 (m, 1H), 2.55-2.65 (m, 1H), 2.39-2.48 (m, 1H), 1.99-2.10 (m, 1H). LCMS (ESI) m/z: 498.0 [M+H]⁺.

Example 23: 2-(2,6-Dioxopiperidin-3-yl)-N—((S)-2-methyl-1-phenylpropyl)-1-oxoisoindoline-5-carboxamide

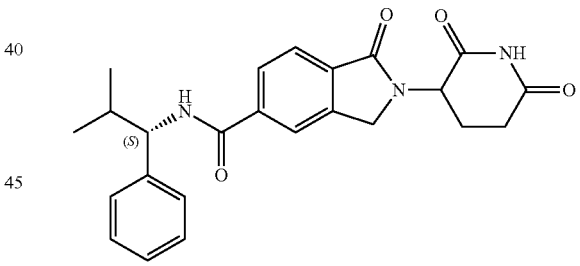

A. 2-(2,6-Dioxopiperidin-3-yl)-N—((S)-2-methyl-1-phenylpropyl)-1-oxoisoindoline-5-carboxamide 2-(2,6-Dioxopiperidin-3-yl)-1-oxoisoindoline-5-carboxylic acid (1.0 eq), (S)-2-methyl-1-phenyl-propan-1-amine hydrochloride (1.0 eq), and DIPEA (4.0 eq) were combined in DMF (0.17 M). To this solution was added HATU (1.1 eq) and the resulting mixture was stirred at ambient temperature for 16 h. The reaction mixture was purified by standard methods to afford 2-(2,6-dioxopiperidin-3-yl)-N—((S)-2-methyl-1-phenylpropyl)-1-oxoisoindoline-5-carboxamide (52.8% yield). ¹H NMR (400 MHz, DMSO-d₆) δ 10.98-11.03 (m, 1H), 8.88-8.95 (m, 1H), 8.02-8.06 (m, 1H), 7.94-7.99 (m, 1H), 7.79-7.84 (m, 1H), 7.38-7.47 (m, 2H), 7.32 (s, 2H), 7.18-7.26 (m, 1H), 5.09-5.17 (m, 1H), 4.65-4.72 (m, 1H), 4.48-4.55 (m, 1H), 4.35-4.43 (m, 1H), 2.86-2.98 (m, 1H), 2.57-2.65 (m, 1H), 2.35-2.45 (m, 1H), 2.09-

2.20 (m, 1H), 1.97-2.06 (m, 1H), 0.99-1.05 (m, 3H), 0.69-0.76 (m, 3H). LCMS (ESI) m/z: 420.2 [M+H]⁺.

Example 24: N—((R)-1-(2-cyclopropoxyphenyl)-2,2,2-trifluoroethyl)-2-(2,6-dioxopiperidin-3-yl)-1-oxoisoindoline-5-carboxamide

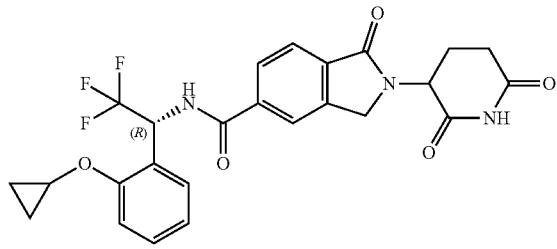

A. 2-Cyclopropoxybenzaldehyde

To a solution of 2-hydroxybenzaldehyde (1.0 eq) and bromocyclopropane (10.0 eq) in DMA (0.82 M) was added Cs₂CO₃ (2.0 eq) and potassium iodide (0.3 eq). The mixture was stirred at 150° C. for 12 h. The reaction mixture was diluted with water, extracted with EtOAc, and the combined organic layers were washed with brine, dried over sodium sulfate, filtered and concentrated under reduced pressure to give a residue. The residue was purified by standard methods to afford 2-cyclopropoxybenzaldehyde (25.1% yield). ¹H NMR (400 MHz, CDCl₃) δ 10.41 (s, 1H), 7.83-7.81 (m, 1H), 7.58-7.56 (m, 1H), 7.37 (d, J=8.0 Hz, 1H), 7.05-7.03 (m, 1H), 3.88-3.83 (m, 1H), 0.88-0.86 (m, 4H).

B. (S,E)-N-(2-Cyclopropoxybenzylidene)-2-methylpropane-2-sulfinamide

To a solution of 2-cyclopropoxybenzaldehyde (1.0 eq), (S)-2-methylpropane-2-sulfinamide (1.0 eq) in THF (0.28 M) was added tetraethoxytitanium (2.0 eq), and the mixture was stirred at 20° C. for 0.5 h. Then the mixture was stirred at 60° C. for 11.5 h. To the mixture was added water, the mixture was filtered and the filter cake was washed with EtOAc. The filtrate was diluted with water and extracted with EtOAc. The combined organic layers were washed with brine, dried over anhydrous sodium sulfate, filtered and concentrated under reduced pressure to give a residue. The residue was purified by standard methods to afford (S,E)-N-(2-cyclopropoxybenzylidene)-2-methylpropane-2-sulfinamide (81.5% yield). ¹H NMR (400 MHz, CDCl₃) δ 8.98 (s, 1H), 7.99-7.97 (m, 1H), 7.50-7.46 (m, 1H), 7.36-7.33 (m, 1H), 7.05-7.01 (m, 1H), 3.82-3.77 (m, 1H), 1.26 (s, 9H), 0.87-0.82 (m, 4H). LCMS (ESI) m/z: 266.1 [M+H]⁺.

C. (S)—N—((R)-1-(2-Cyclopropoxyphenyl)-2,2,2-trifluoroethyl)-2-methylpropane-2-sulfinamide To a solution of (S,E)-N-(2-cyclopropoxybenzylidene)-2-methylpropane-2-sulfinamide (1.0 eq) in THF (50 mL) at −60° C. was added tetrabutylammonium difluorotriphenylsilicate (0.5 eq). The mixture was stirred at −60° C. for 30 min and (trifluoromethyl)trimethylsilane (3.0 eq) was added. The mixture was stirred at −60° C. for 11.5 h. The reaction quenched with a saturated aqueous ammonium chloride solution, diluted with water and extracted with EtOAc. The organic layer was washed with brine, dried over anhydrous sodium sulfate, filtered, and concentrated under reduced pressure. The residue was purified by standard methods to afford (S)—N—((R)-1-(2-cyclopropoxyphenyl)-2,2,2-trifluoroethyl)-2-methylpropane-2-sulfinamide (47.47% yield). LCMS (ESI) m/z: 336.0 [M+H]⁺.

D. (R)-1-(2-Cyclopropoxyphenyl)-2,2,2-trifluoroethan-1-amine hydrochloride

To a solution of (S)—N—((R)-1-(2-cyclopropoxyphenyl)-2,2,2-trifluoroethyl)-2-methylpropane-2-sulfinamide (1.0 eq) in DCM (0.3 M) was added a 4 M solution of hydrochloric acid in EtOAc (13.4 eq). The solution was stirred at 20° C. for 2 h. The reaction mixture was concentrated under reduced pressure to give a residue. To the residue was added water and the mixture was then concentrated under reduced pressure to afford (R)-1-(2-cyclopropoxyphenyl)-2,2,2-trifluoroethanamine hydrochloride (62.65% yield). ¹H NMR (400 MHz, DMSO-d₆) δ 9.23 (s, 3H), 7.60 (m, 1H), 7.58-7.51 (m, 1H), 7.46-7.43 (m, 1H), 7.15-7.10 (m, 1H), 5.45-5.28 (m, 1H), 4.01-3.97 (m, 1H), 0.84-0.69 (m, 4H). LCMS (ESI) m/z: 232.0 [M+H]⁺.

E. N—((R)-1-(2-Cyclopropoxyphenyl)-2,2,2-trifluoroethyl)-2-(2,6-dioxopiperidin-3-yl)-1-oxoisoindoline-5-carboxamide To a solution of (R)-1-(2-cyclopropoxyphenyl)-2,2,2-trifluoroethanamine hydrochloride (1.0 eq) and 2-(2,6-dioxopiperidin-3-yl)-1-oxoisoindoline-5-carboxylic acid (1.2 eq) in DMF (0.11 M) was added DIPEA (3.0 eq) and HATU (1.2 eq). The mixture was stirred at 25° C. for 12 h. The reaction mixture was purified by standard methods to afford N—((R)-1-(2-cyclopropoxyphenyl)-2,2,2-trifluoroethyl)-2-(2,6-dioxopiperidin-3-yl)-1-oxoisoindoline-5-carboxamide (63.1% yield). ¹H NMR (400 MHz, DMSO-d₆) δ 11.00 (s, 1H), 9.53 (d, J=9.2 Hz, 1H), 8.08 (s, 1H), 7.99 (d, J=7.6 Hz, 1H), 7.84 (d, J=8.0 Hz, 1H), 7.78 (d, J=7.6 Hz, 1H), 7.43-7.37 (m, 2H), 7.07 (t, J=7.2 Hz, 1H), 6.43-6.36 (m, 1H), 5.16-5.12 (m, 1H), 4.55-4.51 (m, 1H), 4.43-4.39 (m, 1H), 4.00 (d, J=2.0 Hz, 1H), 2.95-2.88 (m, 1H), 2.63 (s, 1H), 2.42-2.41 (m, 1H), 2.05-2.02 (m, 1H), 0.82 (d, J=3.1 Hz, 2H), 0.66 (s, 2H). LCMS (ESI) m/z: 502.2 [M+H]⁺.

Example 25 and 26: N—((R)-1-(3-Chloropyridin-2-yl)-2,2,2-trifluoroethyl)-2-((S)-2,6-dioxopiperidin-3-yl)-1-oxoisoindoline-5-carboxamide and N—((R)-1-(3-chloropyridin-2-yl)-2,2,2-trifluoroethyl)-2-((R)-2,6-dioxopiperidin-3-yl)-1-oxoisoindoline-5-carboxamide

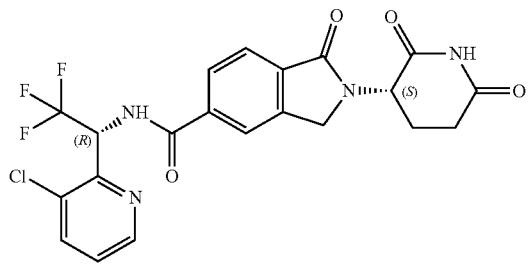

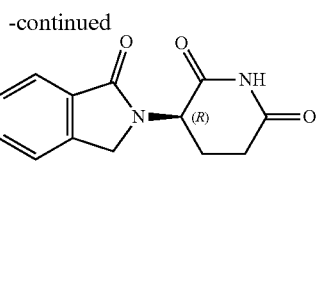

A. N—((R)-1-(3-Chloropyridin-2-yl)-2,2,2-trifluoroethyl)-2-((S)-2,6-dioxopiperidin-3-yl)-1-oxoisoindoline-5-carboxamide and N—((R)-1-(3-chloropyridin-2-yl)-2,2,2-trifluoroethyl)-2-((R)-2,6-dioxopiperidin-3-yl)-1-oxoisoindoline-5-carboxamide N—((R)-1-(3-Chloropyridin-2-yl)-2,2,2-trifluoroethyl)-2-(2,6-dioxopiperidin-3-yl)-1-oxoisoindoline-5-carboxamide (preparation described herein) was separated by chiral preparative SFC chromatography to provide the individual diastereomers whose absolute stereochemistry was confirmed using vibrational circular dichroism.

N—((R)-1-(3-Chloropyridin-2-yl)-2,2,2-trifluoroethyl)-2-((S)-2,6-dioxopiperidin-3-yl)-1-oxoisoindoline-5-carboxamide was obtained in 19.2% yield after separation. $^1$H NMR (400 MHz, DMSO-$d_6$) δ 11.01 (s, 1H), 9.68 (d, J=8.8 Hz, 1H), 8.67 (dd, J=1.2, 4.4 Hz, 1H), 8.14 (s, 1H), 8.10 (dd, J=1.2, 8.4 Hz, 1H), 8.04-8.02 (m, 1H), 7.81 (d, J=8.0 Hz, 1H), 7.57 (dd, J=4.4, 8.0 Hz, 1H), 6.55 (t, J=8.4 Hz, 1H), 5.14 (dd, J=5.2, 13.2 Hz, 1H), 4.54-4.37 (m, 2H), 2.96-2.87 (m, 1H), 2.63-2.58 (m, 1H), 2.44-2.40 (m, 1H), 2.07-2.00 (m, 1H). LCMS (ESI) m/z 481.1 [M+H]$^+$.

N—((R)-1-(3-Chloropyridin-2-yl)-2,2,2-trifluoroethyl)-2-((R)-2,6-dioxopiperidin-3-yl)-1-oxoisoindoline-5-carboxamide was obtained in 14.9% yield after separation. $^1$H NMR (400 MHz, DMSO-$d_6$) δ 11.01 (s, 1H), 9.67 (d, J=8.8 Hz, 1H), 8.67 (dd, J=1.2, 4.4 Hz, 1H), 8.14 (s, 1H), 8.10 (dd, J=1.2, 8.0 Hz, 1H), 8.02 (d, J=7.6 Hz, 1H), 7.81 (d, J=7.6 Hz, 1H), 7.57 (dd, J=4.4, 8.0 Hz, 1H), 6.59-6.51 (m, 1H), 5.14 (dd, J=5.2, 13.2 Hz, 1H), 4.54-4.50 (m, 1H), 4.42-4.37 (m, 1H), 2.96-2.87 (m, 1H), 2.63-2.59 (m, 1H), 2.38-2.37 (m, 1H), 2.07-2.00 (m, 1H). LCMS (ESI) m/z 481.1 [M+H]$^+$.

Example 27: Alternative synthesis of N—((R)-1-(3-chloropyridin-2-yl)-2,2,2-trifluoroethyl)-2-((S)-2,6-dioxopiperidin-3-yl)-1-oxoisoindoline-5-carboxamide

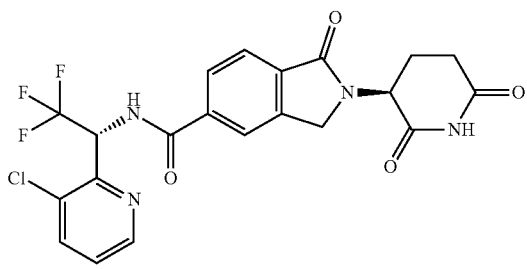 [SMILES: O=C1CC[C@H](N2Cc3cc(C(=O)N[C@H](c4ncccc4Cl)C(F)(F)F)ccc3C2=O)C(=O)N1]

A. (S,E)-N-((3-Chloropyridin-2-yl)methylene)-2-methylpropane-2-sulfinamide

To a solution of 3-chloropicolinaldehyde (1.0 eq) and (S)-2-methylpropane-2-sulfinamide (1.0 eq) in DCM (0.6 M) was added Cs$_2$CO$_3$ (1.2 eq). The mixture was stirred at ambient temperature for 12 h. The mixture was filtered and concentrated under reduced pressure to afford (S,E)-N-((3-chloropyridin-2-yl)methylene)-2-methylpropane-2-sulfinamide (quantitative yield). $^1$H NMR (400 MHz, CDCl$_3$) δ 9.05 (s, 1H), 8.70-8.68 (m, 1H), 7.81 (dd, J=0.8, 8.0 Hz, 1H), 7.36 (dd, J=4.4, 8.4 Hz, 1H), 1.30 (s, 9H). LCMS (ESI) m/z 245.0 [M+H]$^+$.

B. (S)—N—((R)-1-(3-Chloropyridin-2-yl)-2,2,2-trifluoroethyl)-2-methylpropane-2-sulfinamide To a solution of (S,E)-N-((3-chloropyridin-2-yl)methylene)-2-methylpropane-2-sulfinamide (1.0 eq) in THF (0.4 M) was added tetrabutylammonium difluorotriphenylsilicate (0.20 eq) at −70° C. and the mixture was stirred for 0.5 h. (Trifluoromethyl)trimethylsilane (2.0 eq) was added dropwise and the mixture was stirred at −70° C. for 2 h. Then the mixture was warmed to −10° C. and was stirred for 2 h. The mixture was quenched with a saturated ammonium chloride aqueous solution and extracted with EtOAc. The combined organic layers were dried over anhydrous sodium sulfate. The organic layer was filtered and the filtrate was concentrated under reduced pressure. The residue was purified by preparative HPLC (40-58% acetonitrile+0.2% formic acid in water, over 25 min) and product containing fractions were concentrated under reduced pressure to afford (S)—N—((R)-1-(3-chloropyridin-2-yl)-2,2,2-trifluoroethyl)-2-methylpropane-2-sulfinamide (58.2% yield). $^1$H NMR (400 MHz, DMSO-$d_6$) δ 8.67 (d, J=4.8 Hz, 1H), 8.12 (d, J=8.0 Hz, 1H), 7.57 (dd, J=4.8, 8.4 Hz, 1H), 6.08 (d, J=8.8 Hz, 1H), 5.58-5.54 (m, 1H), 1.13 (s, 9H). LCMS (ESI) m/z: 315.1 [M+H]$^+$.

C. (R)-1-(3-Chloropyridin-2-yl)-2,2,2-trifluoroethan-1-amine hydrochloride

To a solution of (S)—N—((R)-1-(3-chloropyridin-2-yl)-2,2,2-trifluoroethyl)-2-methylpropane-2-sulfinamide (1.0 eq) in DCM (0.2 M) was added a 4 M solution of hydrochloric acid in EtOAc (12.6 eq) at 0° C. The mixture was stirred at 25° C. for 2 h. The mixture was concentrated under reduced pressure and the residue was triturated with petroleum ether, filtered, and dried under reduced pressure to afford (R)-1-(3-chloropyridin-2-yl)-2,2,2-trifluoroethan-1-amine hydrochloride (quantitative yield). $^1$H NMR (400 MHz, DMSO-$d_6$) δ 10.00-9.17 (m, 3H), 8.72-8.71 (m, 1H), 8.18 (dd, J=1.2, 8.4 Hz, 1H), 7.66 (dd, J=4.4, 8.0 Hz, 1H), 5.84-5.75 (m, 1H). LCMS (ESI) m/z: 211.0 [M+H]$^+$.

D. (S)-2-(1-Amino-5-(tert-butoxy)-1,5-dioxopentan-2-yl)-1-oxoisoindoline-5-carboxylic acid To a solution of tert-butyl 5-amino-4-[(2S)-5-bromo-1-oxo-isoindolin-2-yl]-5-oxo-pentanoate (1.0 eq) and dicyclohexyl (3-dicyclohexylphosphaniumylpropyl) phosphonium ditetrafluoroborate (1.0 eq) in DMF (0.5 M) was added water (2.0 eq), palladium acetate (0.1 eq) and K$_2$CO$_3$ (1.5 eq). The suspension was degassed under vacuum and purged with carbon monoxide several times. The mixture was stirred under a carbon monoxide atmosphere (50 psi) at 80° C. for 16 h, then cooled to ambient temperature, and filtered.

To the filtrate was added water, and the aqueous layer was washed with EtOAc. The aqueous layer was then acidified with a 12 N aqueous solution of hydrochloric acid to pH 2 and extracted with EtOAc and the combined organic layers were washed with water, brine, dried over anhydrous sodium sulfate, filtered and concentrated. The crude product was triturated with methyl t-butyl ether and filtered to afford (2S)-2-(4-tert-butoxy-1-carbamoyl-4-oxo-butyl)-1-oxo-isoindoline-5-carboxylic acid (44.2% yield). LCMS (ESI) m/z: 385.1 [M+Na]+.

E. (S)-tert-Butyl 5-Amino-4-(5-(((R)-1-(3-chloro-pyridin-2-yl)-2,2,2-trifluoroethyl)carbamoyl)-1-oxoi-soindolin-2-yl)-5-oxopentanoate To a solution of (S)-2-(1-amino-5-(tert-butoxy)-1,5-di-oxopentan-2-yl)-1-oxoisoindoline-5-carboxylic acid (1.0 eq) and (R)-1-(3-chloropyridin-2-yl)-2,2,2-trifluoroethan-1-amine hydrochloride (1.0 eq) in DMF (0.28 M) was added HATU (1.2 eq) and DIPEA (3.0 eq). The mixture was stirred at 25° C. for 2 h and then concentrated under reduced pressure. The residue was purified by preparative HPLC (40-70% acetonitrile+0.2% formic acid in water, over 13 min) and product containing fractions were concentrated under reduced pressure to afford (S)-tert-butyl 5-amino-4-(5-(((R)-1-(3-chloropyridin-2-yl)-2,2,2-trifluoroethyl)car-bamoyl)-1-oxoisoindolin-2-yl)-5-oxopentanoate (52.0% yield). $^1$H NMR (400 MHz, DMSO-$d_6$) δ 9.62 (d, J=8.8 Hz, 1H), 8.67 (dd, J=1.2, 4.4 Hz, 1H), 8.13 (s, 1H), 8.10 (dd, J=1.6, 8.4 Hz, 1H), 8.01 (d, J=8.0 Hz, 1H), 7.78 (d, J=8.0 Hz, 1H), 7.58-7.55 (m, 2H), 7.20 (s, 1H), 6.59-6.51 (m, 1H), 4.75 (dd, J=3.6, 10.0 Hz, 1H), 4.67-4.63 (m, 1H), 4.54-4.49 (m, 1H), 2.19-2.15 (m, 3H), 2.07-1.95 (m, 1H), 1.32 (s, 9H). LCMS (ESI) m/z: 555.2 [M+H]+.

F. N—((R)-1-(3-chloropyridin-2-yl)-2,2,2-trifluoro-ethyl)-2-((S)-2,6-dioxopiperidin-3-yl)-1-oxoisoindo-line-5-carboxamide A mixture of (S)-tert-butyl 5-amino-4-(5-(((R)-1-(3-chlo-ropyridin-2-yl)-2,2,2-trifluoroethyl)carbamoyl)-1-oxoisoin-dolin-2-yl)-5-oxopentanoate (1.0 eq), benzenesulfonic acid (2.5 eq) in acetonitrile (0.18 M) was degassed and purged with nitrogen for 3 times and then the mixture was stirred at 60° C. for 12 h under a nitrogen atmosphere. The mixture was concentrated and then diluted with DCM. The organic layer was washed with a saturated sodium bicarbonate aqueous solution, dried over anhydrous sodium sulfate, filtered and the filtrate was concentrated under reduced pressure. The residue was purified by standard methods to afford N—((R)-1-(3-chloropyridin-2-yl)-2,2,2-trifluoro-ethyl)-2-((S)-2,6-dioxopiperidin-3-yl)-1-oxoisoindoline-5-carboxamide (58.6% yield). $^1$H NMR (400 MHz, DMSO-$d_6$) δ 11.02 (s, 1H), 9.70 (d, J=8.8 Hz, 1H), 8.67 (dd, J=1.2, 4.4 Hz, 1H), 8.14 (s, 1H), 8.10 (dd, J=1.2, 8.0 Hz, 1H), 8.03 (d, J=8.0 Hz, 1H), 7.82 (d, J=8.0 Hz, 1H), 7.57 (dd, J=4.4, 8.0 Hz, 1H), 6.55 (q, J=8.0 Hz, 1H), 5.14 (dd, J=5.2, 13.2 Hz, 1H), 4.54-4.37 (m, 2H), 2.96-2.87 (m, 1H), 2.63 (s, 1H), 2.41-2.38 (m, 1H), 2.07-1.99 (m, 1H). LCMS (ESI) m/z: 481.1 [M+H]+.

Example 28: N—((R)-1-(3,5-Difluoropyridin-2-yl)-2,2,2-trifluoroethyl)-2-(2,6-dioxopiperidin-3-yl)-1-oxoisoindoline-5-carboxamide

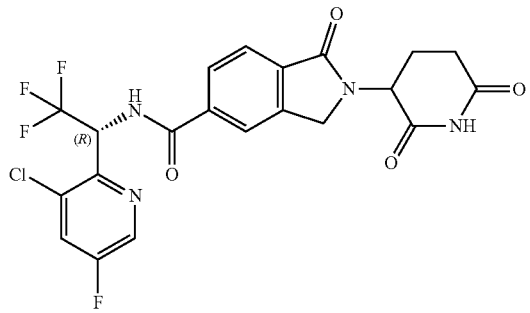

A. (S,E)-N-((3-Chloro-5-fluoropyridin-2-yl)methyl-ene)-2-methylpropane-2-sulfinamide To a solution of 3-chloro-5-fluoropicolinaldehyde (1.0 eq) and (S)-2-methylpropane-2-sulfinamide (1.5 eq) in DCM (0.34 M) was added CuSO$_4$ (2.0 eq). The mixture was stirred at ambient temperature for 12 h. The mixture was filtered, concentrated under reduced pressure, and then purified by silica gel chromatography (0-8% EtOAc in petroleum ether to afford (S,E)-N-((3-chloro-5-fluoropyridin-2-yl)methyl-ene)-2-methylpropane-2-sulfinamide (90.0% yield). $^1$H NMR (400 MHz, CDCl$_3$) δ 9.02 (s, 1H), 8.61 (d, J=2.4 Hz, 1H), 7.62 (dd, J=2.4 Hz, 7.6 Hz, 1H), 1.33 (s, 9H). LCMS (ESI) m/z 262.9 [M+H]+.

B. (S)—N—((R)-1-(3-Chloro-5-fluoropyridin-2-yl)-2,2,2-trifluoroethyl)-2-methylpropane-2-sulfinamide To a solution of (S,E)-N-((3-chloro-5-fluoropyridin-2-yl) methylene)-2-methylpropane-2-sulfinamide (1.0 eq) in THF (0.26 M) was added tetrabutylammonium difluorotriphenyl-silicate (0.2 eq) at −60° C. and the mixture was stirred for 0.5 h. (Trifluoromethyl)trimethylsilane (1.6 eq) was added drop-wise and the mixture was stirred at −60° C. for 3 h. The mixture was warmed to −10° C., stirred for 12 h, then quenched with a saturated ammonium chloride aqueous solution, and extracted with EtOAc. The combined organic layers were dried over anhydrous sodium sulfate, filtered and the filtrate was concentrated in vacuo. The residue was purified by standard methods to afford (S)—N—((R)-1-(3-chloro-5-fluoropyridin-2-yl)-2,2,2-trifluoroethyl)-2-methyl-propane-2-sulfinamide (20.0% yield). $^1$H NMR (400 MHz, CDCl$_3$) δ 8.36 (d, J=2.4 Hz, 1H), 7.49 (dd, J=2.4 Hz, 7.6 Hz, 1H), 5.36-5.29 (m, 1H), 5.13 (d, J=8.8 Hz, 1H), 1.22 (s, 9H). LCMS (ESI) m/z: 332.9 [M+H]+.

C. (R)-1-(3-Chloro-5-fluoropyridin-2-yl)-2,2,2-trif-luoroethan-1-amine hydrochloride To a solution of (S)—N—((R)-1-(3-chloro-5-fluoropyri-din-2-yl)-2,2,2-trifluoroethyl)-2-methylpropane-2-sulfina-mide (1.0 eq) in DCM (0.09 M) was added a 4 M solution of hydrochloric acid in EtOAc (7.5 eq). The mixture was stirred at 15° C. for 1 h. The mixture was concentrated under reduced pressure to afford (R)-1-(3-chloro-5-fluoropyridin-2-yl)-2,2,2-trifluoroethan-1-amine hydrochloride (96.6% yield). $^1$H NMR (400 MHz, CD$_3$OD) δ 8.69 (d, J=2.4 Hz, 1H), 8.12 (dd, J=2.4 Hz, 8.0 Hz, 1H), 5.93 (q, J=6.4 Hz, 1H). LCMS (ESI) m/z: 228.9 [M+H]⁺.

D. N—((R)-1-(3-Chloro-5-fluoropyridin-2-yl)-2,2,2-trifluoroethyl)-2-(2,6-dioxopiperidin-3-yl)-1-oxoisoindoline-5-carboxamide To a solution of (R)-1-(3-chloro-5-fluoropyridin-2-yl)-2,2,2-trifluoroethan-1-amine hydrochloride (1.0 eq) and 2-(2,6-dioxopiperidin-3-yl)-1-oxoisoindoline-5-carboxylic acid (1.0 eq) in DMF (0.13 M) was added DIPEA (5.0 eq) and HATU (1.2 eq). The mixture was stirred at 25° C. for 12 h. The reaction mixture was purified by standard methods to afford N—((R)-1-(3-chloro-5-fluoropyridin-2-yl)-2,2,2-trifluoroethyl)-2-(2,6-dioxopiperidin-3-yl)-1-oxoisoindoline-5-carboxamide (45.1% yield). ¹H NMR (400 MHz, DMSO-d₆) δ 11.00 (s, 1H), 9.70 (d, J=8.4 Hz, 1H), 8.75 (d, J=2.0 Hz, 1H), 8.29 (dd, J=2.4 Hz, 8.4 Hz, 1H), 8.13 (s, 1H), 8.02 (t, J=3.2 Hz, 1H), 7.82 (d, J=8.0 Hz, 1H), 6.57-6.49 (m, 1H), 5.14 (dd, J=5.2 Hz, 13.2 Hz, 1H), 4.52 (d, J=17.6 Hz, 1H), 4.40 (d, J=17.6 Hz, 1H), 2.96-2.87 (m, 1H), 2.63-2.59 (m, 1H), 2.45-2.40 (m, 1H), 2.04-2.03 (m, 1H). LCMS (ESI) m/z: 499.0 [M+H]⁺.

Example 29: N—((R)-1-(3,5-Dichloropyridin-2-yl)-2,2,2-trifluoroethyl)-2-(2,6-dioxopiperidin-3-yl)-1-oxoisoindoline-5-carboxamide

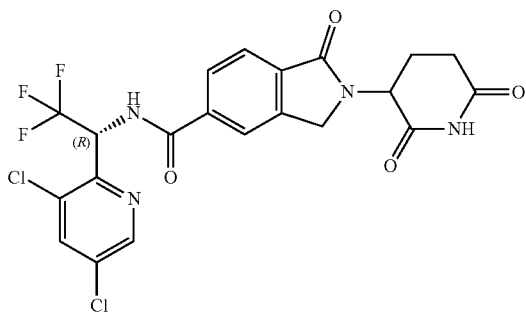

A. (S,E)-N-((3,5-Dichloropyridin-2-yl)methylene)-2-methylpropane-2-sulfinamide

To a solution of 3,5-dichloropicolinaldehyde (1.0 eq) and (S)-2-methylpropane-2-sulfinamide (1.5 eq) in DCM (0.61 M) was added CuSO₄ (2.0 eq). The mixture was stirred at ambient temperature for 12 h. The mixture was filtered, concentrated under reduced pressure, and then purified by silica gel chromatography (0-8% EtOAc in petroleum ether to afford (S,E)-N-((3,5-dichloropyridin-2-yl)methylene)-2-methylpropane-2-sulfinamide (47.3% yield). ¹H NMR (400 MHz, CDCl₃) δ 9.01 (s, 1H), 8.67 (d, J=2.0 Hz, 1H), 7.87 (d, J=2.0 Hz, 1H), 1.33 (s, 9H). LCMS (ESI) m/z 278.9 [M+H]⁺.

B. (S)—N—((R)-1-(3,5-Dichloropyridin-2-yl)-2,2,2-trifluoroethyl)-2-methylpropane-2-sulfinamide To a solution of (S,E)-N-((3,5-dichloropyridin-2-yl)methylene)-2-methylpropane-2-sulfinamide (1.0 eq) in THF (0.24 M) was added tetrabutylammonium difluorotriphenylsilicate (0.2 eq) at −60° C. and the mixture was stirred for 0.5 h. (Trifluoromethyl)trimethylsilane (1.5 eq) was added dropwise and the mixture was stirred at −60° C. for 3 h. The mixture was warmed to −10° C. and it was stirred for 12 h, then quenched with a saturated ammonium chloride aqueous solution, and extracted with EtOAc. The combined organic layers were dried over anhydrous sodium sulfate, filtered and the filtrate was concentrated in vacuo. The residue was purified by standard methods to afford (S)—N—((R)-1-(3,5-dichloropyridin-2-yl)-2,2,2-trifluoroethyl)-2-methylpropane-2-sulfinamide (29.9% yield). ¹H NMR (400 MHz, CDCl₃) δ 8.52 (d, J=2.4 Hz, 1H), 7.82 (d, J=2.0 Hz, 1H), 5.44-5.37 (m, 1H), 5.23 (d, J=8.8 Hz, 1H), 1.32 (s, 9H). LCMS (ESI) m/z: 349.1 [M+H]⁺.

C. (R)-1-(3,5-Dichloropyridin-2-yl)-2,2,2-trifluoroethan-1-amine hydrochloride

To a solution of (S)—N—((R)-1-(3,5-dichloropyridin-2-yl)-2,2,2-trifluoroethyl)-2-methylpropane-2-sulfinamide (1.0 eq) in DCM (0.3 M) was added a 4 M solution of hydrochloric acid in EtOAc (40.0 eq). The mixture was stirred at 15° C. for 1 h. The mixture was concentrated under reduced pressure to afford (R)-1-(3,5-dichloropyridin-2-yl)-2,2,2-trifluoroethan-1-amine hydrochloride (quantitative yield). ¹H NMR (400 MHz, DMSO-d₆) δ 9.17 (s, 2H), 8.84 (d, J=2.0 Hz, 1H), 8.53 (d, J=2.0 Hz, 1H), 5.82 (q, J=6.8 Hz, 1H). LCMS (ESI) m/z: 244.9 [M+H]⁺.

D. N—((R)-1-(3,5-Dichloropyridin-2-yl)-2,2,2-trifluoroethyl)-2-(2,6-dioxopiperidin-3-yl)-1-oxoisoindoline-5-carboxamide To a solution of (R)-1-(3,5-dichloropyridin-2-yl)-2,2,2-trifluoroethan-1-amine hydrochloride (1.0 eq) and 2-(2,6-dioxopiperidin-3-yl)-1-oxoisoindoline-5-carboxylic acid (1.0 eq) in DMF (0.42 M) was added DIPEA (4.7 eq) and HATU (1.1 eq). The mixture was stirred at 25° C. for 12 h. The reaction mixture was purified by standard methods to afford N—((R)-1-(3,5-dichloropyridin-2-yl)-2,2,2-trifluoroethyl)-2-(2,6-dioxopiperidin-3-yl)-1-oxoisoindoline-5-carboxamide (54.3% yield). ¹H NMR (400 MHz, DMSO-d₆) δ 11.02 (s, 1H), 9.73 (d, J=8.4 Hz, 1H), 8.77 (s, 1H), 8.43 (s, 1H), 8.13 (s, 1H), 8.02 (dd, J=4.0 Hz, 7.2 Hz, 1H), 7.82 (d, J=8.0 Hz, 1H), 6.55-6.47 (m, 1H), 5.15 (dd, J=5.2 Hz, 13.2 Hz, 1H), 4.52 (d, J=17.6 Hz, 1H), 4.40 (d, J=17.6 Hz, 1H), 2.97-2.87 (m, 1H), 2.63-2.59 (m, 1H), 2.45-2.40 (m, 1H), 2.04-2.01 (m, 1H). LCMS (ESI) m/z: 515.0 [M+H]⁺.

Example 30: N—((R)-1-(5-Chloro-3-fluoropyridin-2-yl)-2,2,2-trifluoroethyl)-2-((S)-2,6-dioxopiperidin-3-yl)-1-oxoisoindoline-5-carboxamide

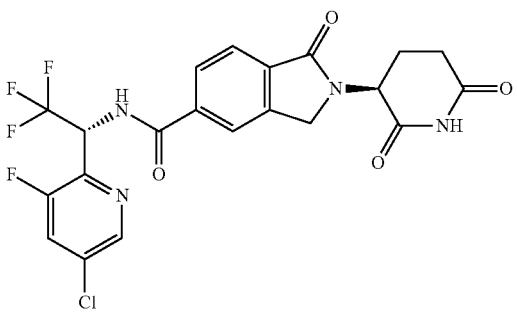 [SMILES: O=C1CC[C@H](N2Cc3cc(C(=O)N[C@H](c4ncc(Cl)cc4F)C(F)(F)F)ccc3C2=O)C(=O)N1]

A. tert-Butyl (S)-5-amino-4-(5-(((R)-1-(5-chloro-3-fluoropyridin-2-yl)-2,2,2-trifluoroethyl)carbamoyl)-1-oxoisoindolin-2-yl)-5-oxopentanoate To a solution of (S)-2-(1-amino-5-(tert-butoxy)-1,5-dioxopentan-2-yl)-1-oxoisoindoline-5-carboxylic acid (preparation described herein, 1.0 eq) and (R)-1-(5-chloro-3-fluoropyridin-2-yl)-2,2,2-trifluoroethan-1-amine hydrochloride (preparation described herein, 1.0 eq) in DMF (0.26 M) was added HATU (1.2 eq) and DIPEA (3.0 eq). The mixture was stirred at 25° C. for 12 h and then concentrated under reduced pressure. The residue was purified by preparative HPLC (45-75% acetonitrile+0.2% formic acid in water, over 15 min) and product containing fractions were concentrated under reduced pressure to afford tert-butyl (S)-5-amino-4-(5-(((R)-1-(5-chloro-3-fluoropyridin-2-yl)-2,2,2-trifluoroethyl)carbamoyl)-1-oxoisoindolin-2-yl)-5-oxopentanoate (59.5% yield). $^1$H NMR (400 MHz, DMSO-$d_6$) δ 9.78 (d, J=8.8 Hz, 1H), 8.67 (d, J=1.6 Hz, 1H), 8.29 (dd, J=1.6, 9.6 Hz, 1H), 8.14 (s, 1H), 8.01 (d, J=8.4 Hz, 1H), 7.79 (d, J=8.0 Hz, 1H), 7.60 (s, 1H), 7.22 (s, 1H), 6.42-6.38 (m, 1H), 4.77-4.50 (m, 1H), 4.67-4.63 (m, 3H), 2.17-2.15 (m, 3H), 2.02-2.01 (m, 1H), 1.32 (s, 9H). LCMS (ESI) m/z: 573.2 [M+H]$^+$.

B. N—((R)-1-(5-Chloro-3-fluoropyridin-2-yl)-2,2,2-trifluoroethyl)-2-((S)-2,6-dioxopiperidin-3-yl)-1-oxoisoindoline-5-carboxamide A mixture of tert-butyl (S)-5-amino-4-(5-(((R)-1-(5-chloro-3-fluoropyridin-2-yl)-2,2,2-trifluoroethyl)carbamoyl)-1-oxoisoindolin-2-yl)-5-oxopentanoate (1.0 eq) and benzenesulfonic acid (2.5 eq) in acetonitrile (0.18 M) was stirred at 60° C. for 12 h under a nitrogen atmosphere. The mixture was concentrated, diluted with DCM, and washed with a saturated sodium bicarbonate aqueous solution. The organic layer was dried over anhydrous sodium sulfate, filtered and the filtrate was concentrated. The residue was purified by standard methods to afford N—((R)-1-(5-chloro-3-fluoropyridin-2-yl)-2,2,2-trifluoroethyl)-2-((S)-2,6-dioxopiperidin-3-yl)-1-oxoisoindoline-5-carboxamide (72.7% yield). $^1$H NMR (400 MHz, DMSO-$d_6$) δ 11.01 (s, 1H), 9.81 (d, J=8.8 Hz, 1H), 8.67 (s, 1H), 8.31-8.30 (m, 1H), 8.15 (s, 1H), 8.04 (d, J=8.0 Hz, 1H), 7.82 (d, J=8.0 Hz, 1H), 6.43-6.39 (m, 1H), 5.18-5.11 (m, 1H), 4.55-4.39 (m, 2H), 2.97-2.90 (m, 1H), 2.63-2.58 (m, 1H), 2.45-2.33 (m, 1H), 2.05-2.04 (m, 1H). LCMS (ESI) m/z: 499.2 [M+H]$^+$.

Example 31: N—((R)-1-(3-Chloro-5-((dimethylamino)methyl)pyridin-2-yl)-2,2,2-trifluoroethyl)-2-(2,6-dioxopiperidin-3-yl)-1-oxoisoindoline-5-carboxamide hydrochloride

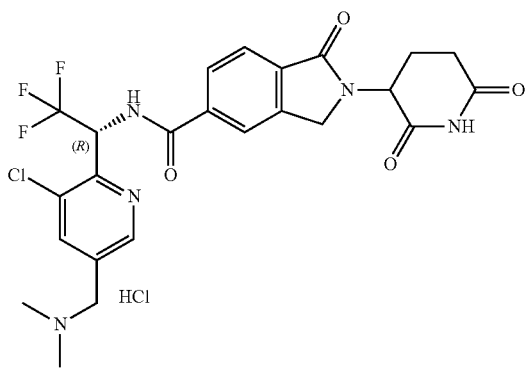

A. 3-Chloro-5-((dimethylamino)methyl)picolinonitrile

To a solution of 3-chloro-5-(chloromethyl)picolinonitrile (1.0 eq) in acetonitrile (0.4 M) was added dimethylamine hydrochloride (2.0 eq) and $K_2CO_3$ (3.0 eq). The resulting mixture was stirred at 55° C. for 12 h, and then filtered. The filtrate was concentrated under reduced pressure. The residue was purified by silica gel chromatography (0-25% EtOAc in petroleum ether) to afford 3-chloro-5-((dimethylamino)methyl)picolinonitrile (84.0% yield). $^1$H NMR (400 MHz, CDCl$_3$) δ 8.54 (s, 1H), 7.90 (s, 1H), 3.52 (s, 2H), 2.29 (s, 6H). LCMS (ESI) m/z: 195.9 [M+H]$^+$.

B. 3-Chloro-5-((dimethylamino)methyl)picolinic acid hydrochloride

To a solution of 3-chloro-5-((dimethylamino)methyl)picolinonitrile (1.0 eq) in EtOH (0.8 M) was added an aqueous solution of sodium hydroxide (5.0 eq) in water (0.8 M). The resulting mixture was stirred at 90° C. for 12 h. The pH of the reaction mixture was adjusted to 1 with an aqueous solution of hydrochloric acid. The mixture was concentrated under reduced pressure. The residue was suspended in methanol, filtered, and concentrated under reduced pressure to afford 3-chloro-5-((dimethylamino)methyl)picolinic acid hydrochloride (quantitative yield) as a white solid. LCMS (ESI) m/z: 215.0 [M+H]$^+$.

C. 3-Chloro-5-((dimethylamino)methyl)-N-methoxy-N-methylpicolinamide

To a mixture of 3-chloro-5-((dimethylamino)methyl)picolinic acid hydrochloride (1.0 eq) in DCM (0.22 M) were added N,O-dimethylhydroxylamine hydrochloride (1.6 eq), 4-methylmorpholine (10.0 eq), HOBt (1.0 eq) and EDCI (1.7 eq). The resulting mixture was stirred at 15° C. for 12 h. The mixture was diluted with DCM, filtered, and the filtrate was concentrated under reduced pressure. The residue was purified by standard methods to afford 3-chloro-5-((dimethylamino)methyl)-N-methoxy-N-methylpicolinamide (47.2% yield). $^1$H NMR (400 MHz, CDCl$_3$) δ 8.34 (s, 1H), 7.69 (s, 1H), 3.49 (s, 3H), 3.38 (s, 2H), 3.33 (s, 3H), 2.19 (s, 6H). LCMS (ESI) m/z: 258.0 [M+H]$^+$.

D. 3-Chloro-5-((dimethylamino)methyl)picolinaldehyde

To a solution of 3-chloro-5-((dimethylamino)methyl)-N-methoxy-N-methylpicolinamide (1.0 eq) in THF (0.29 M) was added a 2.4 M solution of lithium aluminum hydride in THF (1.0 eq) under a nitrogen atmosphere at −70° C. The resulting mixture was stirred under a nitrogen atmosphere at −70° C. for 4 h. The mixture was quenched with saturated aqueous solution of ammonium chloride at −70° C. The mixture was diluted with DCM and stirred at 10° C. for 30 min. The mixture was filtered and the filtrate was concentrated under reduced pressure to give 3-chloro-5-((dimethylamino)methyl)picolinaldehyde (47.2% yield). $^1$H NMR (400 MHz, CDCl$_3$) δ 10.33 (s, 1H), 8.65 (d, J=1.6 Hz, 1H), 7.87 (s, 1H), 2.74 (s, 2H), 2.30 (s, 6H). LCMS (ESI) m/z: 198.9 [M+H]$^+$.

E. (S,E)-N-((3-Chloro-5-((dimethylamino)methyl)pyridin-2-yl)methylene)-2-methylpropane-2-sulfinamide To a solution of 3-chloro-5-((dimethylamino)methyl)picolinaldehyde (1.0 eq) and (S)-2-methylpropane-2-sulfinamide (1.0 eq) in DCM (0.36 M) was added Cs₂CO₃ (2.0 eq). The mixture was stirred at ambient temperature for 12 h. The mixture was filtered, concentrated under reduced pressure, and then purified by standard methods to afford (S,E)-N-((3-chloro-5-((dimethylamino)methyl)pyridin-2-yl)methylene)-2-methylpropane-2-sulfinamide. ¹H NMR (400 MHz, CDCl₃) δ 8.98 (s, 1H), 8.52 (s, 1H), 7.76 (d, J=1.6 Hz, 1H), 3.42 (s, 2H), 2.20 (s, 6H), 1.24 (s, 9H). LCMS (ESI) m/z 302.0 [M+H]⁺.

F. (S)—N—((R)-1-(3-Chloro-5-((dimethylamino)methyl)pyridin-2-yl)-2,2,2-trifluoroethyl)-2-methylpropane-2-sulfinamide To a solution of (S,E)-N-((3-chloro-5-((dimethylamino)methyl)pyridin-2-yl)methylene)-2-methylpropane-2-sulfinamide (1.0 eq) in THF (0.28 M) was added tetrabutylammonium difluorotriphenylsilicate (0.20 eq) at −60° C. and the mixture was stirred for 10 min. (Trifluoromethyl)trimethylsilane (2.0 eq) was added dropwise and the mixture was stirred at −60° C. for 2 h. The mixture was warmed to −20° C. and it was stirred for 12 h, then quenched with a saturated ammonium chloride aqueous solution, and extracted with EtOAc. The combined organic layer was dried over anhydrous sodium sulfate. The organic layer was filtered and the filtrate was concentrated under reduced pressure. The residue was purified by standard methods to afford (S)—N—((R)-1-(3-chloro-5-((dimethylamino)methyl)pyridin-2-yl)-2,2,2-trifluoroethyl)-2-methylpropane-2-sulfinamide (43.2% yield). ¹H NMR (400 MHz, CDCl₃) δ 8.36 (s, 1H), 7.74 (s, 1H), 5.38-5.31 (m, 1H), 5.28 (d, J=8.4 Hz, 1H), 3.39 (s, 2H), 2.21 (s, 6H), 1.23 (s, 9H). LCMS (ESI) m/z: 372.0 [M+H]⁺.

G. (R)-1-(3-Chloro-5-((dimethylamino)methyl)pyridin-2-yl)-2,2,2-trifluoroethan-1-amine dihydrochloride To a solution of (S)—N—((R)-1-(3-chloro-5-((dimethylamino)methyl)pyridin-2-yl)-2,2,2-trifluoroethyl)-2-methylpropane-2-sulfinamide (1.0 eq) in EtOAc (0.14 M) was added a 4 M solution of hydrochloric acid in EtOAc (16.8 eq). The mixture was stirred at 15° C. for 1 h and the solids filtered to afford (R)-1-(3-chloro-5-((dimethylamino)methyl)pyridin-2-yl)-2,2,2-trifluoroethan-1-amine dihydrochloride (88.2% yield). ¹H NMR (400 MHz, DMSO-d₆) δ 11.53 (s, 1H), 9.18 (s, 2H), 8.96 (d, J=1.6 Hz, 1H), 8.51 (s, 1H), 5.85 (q, J=6.8 Hz, 1H), 2.43 (s, 2H), 2.73 (s, 6H). LCMS (ESI) m/z: 267.9 [M+H]⁺.

H. N—((R)-1-(3-Chloro-5-((dimethylamino)methyl)pyridin-2-yl)-2,2,2-trifluoroethyl)-2-(2,6-dioxopiperidin-3-yl)-1-oxoisoindoline-5-carboxamide hydrochloride To a solution of (R)-1-(3-chloro-5-((dimethylamino)methyl)pyridin-2-yl)-2,2,2-trifluoroethan-1-amine dihydrochloride (1.0 eq) and 2-(2,6-dioxopiperidin-3-yl)-1-oxoisoindoline-5-carboxylic acid (1.0 eq) in DMF (0.14 M) was added DIPEA (5.0 eq) and HATU (1.2 eq). The mixture was stirred at 25° C. for 12 h. The reaction mixture was purified by standard methods to afford N—((R)-1-(3-chloro-5-((dimethylamino)methyl)pyridin-2-yl)-2,2,2-trifluoroethyl)-2-(2,6-dioxopiperidin-3-yl)-1-oxoisoindoline-5-carboxamide hydrochloride (61.1% yield). ¹H NMR (400 MHz, DMSO-d₆) δ 11.25 (s, 1H), 11.01 (s, 1H), 9.73 (d, J=8.8 Hz, 1H), 8.86 (s, 1H), 8.41 (s, 1H), 8.15 (s, 1H), 8.04 (t, J=7.2 Hz, 1H), 7.82 (d, J=8.0 Hz, 1H), 6.62-6.54 (m, 1H), 5.15 (dd, J=5.2 Hz, 13.6 Hz, 1H), 4.53 (d, J=17.6 Hz, 1H), 4.42 (s, 2H), 4.38 (d, J=4.0 Hz, 1H), 2.97-2.88 (m, 1H), 2.74 (t, J=3.2 Hz, 6H), 2.63-2.59 (m, 1H), 2.45-2.38 (m, 1H), 2.08-2.02 (m, 1H). LCMS (ESI) m/z: 538.3.0 [M+H]⁺.

Example 32: 2-(2,6-Dioxopiperidin-3-yl)-1-oxo-N—((R)-2,2,2-trifluoro-1-(2-morpholinophenyl)ethyl)isoindoline-5-carboxamide

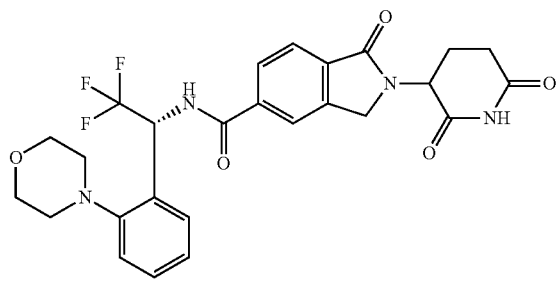 [SMILES: O=C1CCC(N2Cc3cc(C(=O)N[C@H](c4ccccc4N4CCOCC4)C(F)(F)F)ccc3C2=O)C(=O)N1]

A. (S,E)-2-Methyl-N-(2-morpholinobenzylidene)propane-2-sulfinamide

To a solution of (S,E)-2-methyl-N-(2-morpholinobenzylidene)propane-2-sulfinamide (1.0 eq) and (S)-2-methylpropane-2-sulfinamide (1.0 eq) in DCM (0.36 M) was added tetraethoxytitanium (2.0 eq). The mixture was stirred at 60° C. for 12 h. The mixture was filtered, concentrated under reduced pressure, and then purified by standard methods to afford (S,E)-2-methyl-N-(2-morpholinobenzylidene)propane-2-sulfinamide. H NMR (400 MHz, CDCl₃) δ 9.02 (s, 1H), 7.97 (dd, J=1.6, 7.6 Hz, 1H), 7.50-7.46 (m, 1H), 7.17-7.12 (m, 2H), 3.92-3.89 (m, 4H), 3.01-2.99 (m, 4H), 1.27 (s, 9H). LCMS (ESI) m/z 295.0 [M+H]⁺.

B. (S)—N—((R)-1-(3-Chloro-5-((dimethylamino)methyl)pyridin-2-yl)-2,2,2-trifluoroethyl)-2-methylpropane-2-sulfinamide To a solution of (S,E)-2-methyl-N-(2-morpholinobenzylidene)propane-2-sulfinamide (1.0 eq) in THF (0.45 M) was added tetrabutylammonium difluorotriphenylsilicate (0.20 eq) at −70° C. and the mixture was stirred for 0.5 h. (Trifluoromethyl)trimethylsilane (2.0 eq) was added dropwise and the mixture was stirred at −70° C. for 0.5 h. The mixture was warmed to 0° C., stirred for 2 h, then quenched with a saturated ammonium chloride aqueous solution, and extracted with EtOAc. The combined organic layers were dried over anhydrous sodium sulfate, filtered and the filtrate was concentrated under reduced pressure. The residue was purified by standard methods to afford (S)—N—((R)-1-(3-chloro-5-((dimethylamino)methyl)pyridin-2-yl)-2,2,2-trifluoroethyl)-2-methylpropane-2-sulfinamide (4.1% yield). ¹H NMR (400 MHz, CDCl₃) δ 7.42-7.36 (m, 3H), 7.27-7.23 (m, 1H), 5.64 (t, J=8.4 Hz, 1H), 4.61 (d, J=7.2 Hz, 1H), 3.89 (s, 4H), 3.00-2.90 (m, 4H), 1.27 (s, 9H). LCMS (ESI) m/z: 365.3.0 [M+H]⁺.

C. (R)-2,2,2-Trifluoro-1-(2-morpholinophenyl)ethan-1-amine hydrochloride

To a solution of (S)—N—((R)-1-(3-chloro-5-((dimethylamino)methyl)pyridin-2-yl)-2,2,2-trifluoroethyl)-2-methylpropane-2-sulfinamide (1.0 eq) in DCM (0.18 M) was added a 4 M solution of hydrochloric acid in EtOAc (22.2 eq). The mixture was stirred at 15° C. for 1 h and the solids were filtered to afford (R)-2,2,2-trifluoro-1-(2-morpholinophenyl) ethan-1-amine hydrochloride (quantitative yield). LCMS (ESI) m/z: 261.3 [M+H]$^+$.

D. 2-(2,6-Dioxopiperidin-3-yl)-1-oxo-N—((R)-2,2, 2-trifluoro-1-(2-morpholinophenyl)ethyl)isoindoline-5-carboxamide To a solution of (R)-2,2,2-trifluoro-1-(2-morpholinophenyl)ethan-1-amine hydrochloride (1.0 eq) and 2-(2,6-dioxopiperidin-3-yl)-1-oxoisoindoline-5-carboxylic acid (1.0 eq) in DMF (0.28 M) was added DIPEA (3.0 eq) and HATU (1.2 eq). The mixture was stirred at 25° C. for 12 h. The reaction mixture was purified by standard methods to afford 2-(2,6-Dioxopiperidin-3-yl)-1-oxo-N—((R)-2,2,2-trifluoro-1-(2-morpholinophenyl)ethyl)isoindoline-5-carboxamide (38.5% yield). $^1$H NMR (400 MHz, DMSO-d$_6$) δ 11.00 (s, 1H), 9.57 (d, J=9.6 Hz, 1H), 8.09 (s, 1H), 8.00 (d, J=7.6 Hz, 1H), 7.86-7.82 (m, 2H), 7.45-7.39 (m, 2H), 7.31-7.29 (m, 1H), 6.94 (t, J=9.2 Hz, 1H), 5.14 (dd, J=4.8, 13.2 Hz, 1H), 4.50-4.38 (m, 2H), 3.85-3.81 (m, 2H), 3.75-3.71 (m, 2H), 2.98-2.95 (m, 3H), 2.70-2.67 (m, 2H), 2.65-2.63 (m, 1H), 2.50-2.40 (m, 1H), 2.07-2.01 (m, 1H). LCMS (ESI) m/z: 531.2 [M+H]$^+$.

Example 33: N—((R)-1-(3,5-Dichloropyridin-2-yl)-2,2,2-trifluoroethyl)-2-((S)-2,6-dioxopiperidin-3-yl)-1-oxoisoindoline-5-carboxamide

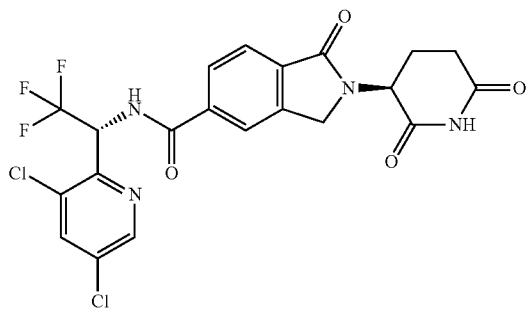 [SMILES: O=C1CC[C@H](N2Cc3cc(C(=O)N[C@H](c4ncc(Cl)cc4Cl)C(F)(F)F)ccc3C2=O)C(=O)N1]

A. tert-Butyl (S)-5-amino-4-(5-(((R)-1-(3,5-dichloropyridin-2-yl)-2,2,2-trifluoroethyl)carbamoyl)-1-oxoisoindolin-2-yl)-5-oxopentanoate To a solution of (S)-2-(1-amino-5-(tert-butoxy)-1,5-dioxopentan-2-yl)-1-oxoisoindoline-5-carboxylic acid (preparation described herein, 1.0 eq) and (R)-1-(3,5-dichloropyridin-2-yl)-2,2,2-trifluoroethan-1-amine hydrochloride (preparation described herein, 1.0 eq) in DMF (0.20 M) was added HATU (1.2 eq) and DIPEA (3.0 eq). The mixture was stirred at 25° C. for 12 h and then concentrated under reduced pressure. The residue was purified by preparative HPLC (40-55% acetonitrile+0.2% formic acid in water, over 24 min) and product containing fractions were concentrated under reduced pressure to afford tert-butyl (S)-5-amino-4-(5-(((R)-1-(3,5-dichloropyridin-2-yl)-2,2,2-trifluoroethyl)carbamoyl)-1-oxoisoindolin-2-yl)-5-oxopentanoate (77.6% yield). $^1$H NMR (400 MHz, DMSO-d$_6$) δ 9.68 (d, J=8.8 Hz, 1H), 8.77 (d, J=2.4 Hz, 1H), 8.44 (s, 1H), 8.13 (d, J=6.0 Hz, 1H), 8.02-7.99 (m, 1H), 7.79 (d, J=8.0 Hz, 1H), 7.60 (s, 1H), 7.21 (s, 1H), 6.55-6.47 (m, 1H), 4.77-4.76 (m, 1H), 4.75-4.50 (m, 2H), 2.17-2.15 (m, 1H), 2.08-2.01 (m, 1H), 1.33 (s, 9H). LCMS (ESI) m/z: 589.2 [M+H]$^+$.

B. N—((R)-1-(3,5-Dichloropyridin-2-yl)-2,2,2-trifluoroethyl)-2-((S)-2,6-dioxopiperidin-3-yl)-1-oxoisoindoline-5-carboxamide A mixture of tert-butyl (S)-5-amino-4-(5-(((R)-1-(3,5-dichloropyridin-2-yl)-2,2,2-trifluoroethyl)carbamoyl)-1-oxoisoindolin-2-yl)-5-oxopentanoate (1.0 eq) and benzenesulfonic acid (2.5 eq) in acetonitrile (0.18 M) was stirred at 60° C. for 12 h under a nitrogen atmosphere. The mixture was concentrated, diluted with DCM, and washed with a saturated sodium bicarbonate aqueous solution. The organic layer was dried over anhydrous sodium sulfate, filtered and the filtrate was concentrated. The residue was purified by standard methods to afford N—((R)-1-(3,5-dichloropyridin-2-yl)-2,2,2-trifluoroethyl)-2-((S)-2,6-dioxopiperidin-3-yl)-1-oxoisoindoline-5-carboxamide (50.0% yield). $^1$H NMR (400 MHz, DMSO-d$_6$) δ 11.02 (s, 1H), 9.73 (d, J=8.8 Hz, 1H), 8.77 (d, J=2.0 Hz, 1H), 8.43 (d, J=2.0 Hz, 1H), 8.14 (s, 1H), 8.03 (d, J=8.0 Hz, 1H), 7.82 (d, J=8.0 Hz, 1H), 6.54-6.50 (m, 1H), 5.17-5.13 (m, 1H), 4.54-4.38 (m, 2H), 2.97-2.92 (m, 1H), 2.64-2.59 (m, 1H), 2.45-2.41 (m, 1H), 2.05-2.03 (m, 1H). LCMS (ESI) m/z: 515.2 [M+H]$^+$.

Assays

Ck1α Degradation Assay

CK1α ePL Assay.

The following is an example of an assay that can be used to determine the CK1α degradation activity of Isoindolinone Carboxamide Compounds in a cell line, for example, the MDS-L cell line.

MDS-L cells stably expressing enhanced ProLabel (ePL)-tagged CK1α were dispensed into a 384-well plate (catalog number 3712, Corning), pre-spotted with compound. Compounds were dispensed by an acoustic dispenser (ATS acoustic transfer system from EDC Biosystems) into a 384-well in a 10 point dose-response curve using 3-fold dilutions starting at 10 μM and going down to 0.0005 μM in DMSO. Twenty-five microliters of media (RPMI 1640+20% Heat Inactivated FBS+1×BME+2 μg/mL Puromycin+200 μg/mL Hygromycin) containing 5000 cells was dispensed per well. Assay plates were incubated at 37° C. with 5% CO$_2$ for the indicated times. At the different time points, 25 μL of the InCELL Hunter™ Detection Reagent Working Solution (catalog number 96-0002, DiscoverX, Fremont, Calif.) was added to each well and incubated at RT for 30 min protected from light. After 30 min, luminescence was read on a PHERAstar luminometer (BMG LABTECH, Cary, N.C.). All percentage of control CK1α destruction curves were processed and evaluated using Activity Base (IDBS, Alameda, Calif.) and then results were pooled and graphed using using Activity Base (IDBS).

CK1α levels in compound-treated wells were normalized to that of DMSO control and expressed as percent of control (PoC) (y). A Four Parameter Logistic Model (Sigmoidal Dose-Response Model) was used to determine the compound's DC$_{50}$ and EC$_{50}$, using the following equation:

$$y=(A+((B-A)/(1+((C/x)^{\wedge}D))))$$

A=Y$_{Min}$ (lowest CK1α level normalized to DMSO control in response to compound treatment, as determined by curve fit)
B=Y$_{Max}$ (CK1α level in DMSO control)
C=EC$_{50}$
D=Hill Slope x=compound concentration $EC_{50}$=the concentration of compound when $y=(Y_{Max}-Y_{Min})/2$ $DC_{50}$=the concentration of the compound when y=50% of DMSO control (50% CK1α degradation)

y=CK1α protein level normalized to DMSO control

The lowest measured CK1α level normalized to DMSO control in response to compound treatment, termed Y value, was used to characterize the compound-mediated CK1α degradation efficiency.

Each of the Isoindolinone Carboxamide Compounds in Table 1, was tested in the MDS-L CK1α ePL degradation assay, and was found to have activity therein. All of the compounds in Table 1 were shown to have an $DC_{50}$<1 µM and Y<50% of DMSO control.

Cell Based Assays

OCI-AML2 Cell Proliferation Assay.

The following is an example of an assay that can be used to determine the anti-proliferative activity of CK1α degrading Isoindolinone Carboxamide Compounds in an AML cell line, for example, the OCI-AML2 cell line (DSMZ: catalogue number ACC-99) or the MV-4-11 cell line (ATCC: catalogue number CRL-9591) at 120 h post-treatment. The seeding density (2000 cells per well) was optimized to ensure assay linearity in 384-well plates.

Increasing concentrations of test compounds (0 to 10 M, half log interval) were spotted in a 10-point dilution fashion via an HP300 digital dispenser into an empty 384-well plate. The DMSO concentration was kept constant for a final assay concentration of 0.1% DMSO. Prior to testing, cells were grown in medium (MEM for OCI-AML2 cell line, IMDM for MV-4-11 cell line) with 10% FBS (HyClone) and expanded in culture flasks to provide sufficient amounts of starting material. Cells were then diluted to 2000 cells per well in 50 µL volume, and added directly to the compound-spotted 384-well plates. Cells were allowed to grow for 120 h in 5% $C_{O2}$ at 37° C. After 120 h of exposure of cells to compounds, viable cell number was assessed via Cell Titer-Glo© Luminescent Cell Viability Assay at a 1 vol: 2 vol ratio according to manufacturer's instructions (Promega Corporation, Madison, Wis.) by quantifying the level of luminescence generated by adenosine-5'-triphosphate (ATP) present and read for luminescence. All growth inhibition curves were processed and evaluated using Activity Base (IDBS, Alameda, Calif.). Cell viability $IC_{50}$ values were calculated using a four parameter logistic model (sigmoidal dose-response model):

$$y=(A+((B-A)/(1+((C/x)^{\wedge}D))))$$

wherein:

$A=Y_{Min}$ $B=Y_{Max}$ $C=EC_{50}$

D=Hill slope $IC_{50}$=the concentration of the compound when Y=50% of DMSO control Y=cell viability measured as luminescence unit, and x=concentration of compound.

Isoindolinone Carboxamide Compounds have been, or will be tested in the cell based assays and have shown, or will be shown, to be effective as inhibitors of AML cell growth.

In Vivo Assays

MV4-11 or OCI-AML2 AML Xenograft Model.

MV4-11 (ATCC) or OCI AML2 (DSMZ) cell lines were cultured in media according to the manufacturer's instructions. These lines were transduced to express luciferase using RediFect™ Green Renilla-Puromycin Lentiviral Particles carrying green emitting Renilla luciferase transgene under control of the stable UbC promoter.

For the establishment of the in vivo efficacy disseminated xenograft model, female NSG mice (Jackson Laboratory) were injected intravenously with $5\times10^6$ cells/mouse. On day 5 or 14 for OCI-AML2 or MV4-11 respectively, bioluminescence was measured by IVIS Lumina imaging system and animals were randomization into treatment groups. Treatment was initiated on the day of randomization and continued for up to 3 weeks. Animals were imaged once a week using the IVIS Lumina imaging system for disease progression and monitored for survival as a study endpoint.

Tumor growth inhibition (TGI) was calculated using the following formula: TGI=bioluminescence photon value of Vehicle group at final timepoint−bioluminescence photon value of Vehicle group at starting timepoint=100% growth. The starting bioluminescence photon value was subtracted from the final bioluminescence photon value for each group and compared to the vehicle control 100% growth.

CK1α Degradation Model.

For PK-PD analysis animals were inoculated with tumor cells subcutaneously in the hind flank. Four weeks following inoculation, the tumor size was measured using LCD digital calipers in mm and the tumor volume was calculated ($width^2 \times length/2$ and expressed in $mm^3$). Once tumor volume reached approximately 500 $mm^3$, animals were randomized into treatment groups. Animals received either a single dose or 5 daily doses of vehicle (5% Tween 80 in 25 mM citrate buffer pH 3.0), test article or positive control (Ara-c 50 mg/kg QD) and tumor and blood samples were taken at timepoints between 0.5 h and 48 h post last dose for assessment of pharmacokinetic and pharmacodynamics endpoints. Pharmacodynamic endpoints include measurement of CK1α levels to assess CK1α degradation, and cleaved caspase 3 via western blot, as a measure of apoptosis induction.

Cell lines that can be used in the xenograft assays described herein include AML cell lines, for example, MV4-11, OCI-AML2, MOLM-13, and HNT-34.

Isoindolinone Carboxamide Compounds have been, or will be tested in the AML xenograft models described herein and have shown, or will be shown, to be effective as treatments of AML in the models.

Activity Table

Each of the Isoindolinone Carboxamide Compounds in Table 1, was tested in one or more of the assays, for example, the ePL CK1α degradation assay, and was found to have activity therein. All of the compounds in Table 1 were shown to have a $DC_{50}$<1 µM and a Y value of <50% of DMSO control, with some compounds having a $DC_{50}$ value indicated by C: $DC_{50}$≤0.10 µM, some a $DC_{50}$ value indicated by B: 0.10 µM<$DC_{50}$≤0.50 µM, and others a $DC_{50}$ value indicated by A: 0.50 µM<$DC_{50}$≤1.0 µM.

Additionally, the compounds were shown to have a CK1α degradation efficiency Y value of <50% of DMSO control, with some compounds having a Y value (shown as *) of 0<Y≤20%, some compounds having a Y value (shown as) of 20%<Y≤35%, and others having a Y value (shown as*) of 35%<Y<50%.

TABLE 1

| Cmpd No. | Cmpd Structure | Cmpd Name | MH+ | DC$_{50}$ | Y |
|---|---|---|---|---|---|
| 1 | | 2-(2,6-dioxopiperidin-3-yl)-1-oxo-N-((S)-1-phenylethyl)isoindoline-5-carboxamide | 392.3 | C | * |
| 2 | | 2-(2,6-dioxopiperidin-3-yl)-N-isopropyl-1-oxoisoindoline-5-carboxamide | 330.1 | B | ** |
| 3 | | N-((S)-1-cyclopentylethyl)-2-(2,6-dioxopiperidin-3-yl)-1-oxoisoindoline-5-carboxamide | 384.2 | C | * |

TABLE 1-continued

| Cmpd No. | Cmpd Structure | Cmpd Name | MH+ | DC$_{50}$ | Y |
|---|---|---|---|---|---|
| 4 | | N-((S)-1-cyclohexylethyl)-2-(2,6-dioxopiperidin-3-yl)-1-oxoisoindoline-5-carboxamide | 398.1 | C | * |
| 5 | | N-((S)-1-cyclopropylethyl)-2-(2,6-dioxopiperidin-3-yl)-1-oxoisoindoline-5-carboxamide | 356.1 | B | ** |
| 6 | | 2-(2,6-dioxopiperidin-3-yl)-1-oxo-N-((S)-1-phenylpropyl)isoindoline-5-carboxamide | 406.2 | C | * |

TABLE 1-continued

| Cmpd No. | Cmpd Structure | Cmpd Name | MH+ | DC$_{50}$ | Y |
|---|---|---|---|---|---|
| 7 | | 2-(2,6-dioxopiperidin-3-yl)-1-oxo-N-((S)-1-p-tolylethyl)isoindoline-5-carboxamide | 406.2 | C | * |
| 8 | | N-((S)-1-(4-chlorophenyl)ethyl)-2-(2,6-dioxopiperidin-3-yl)-1-oxoisoindoline-5-carboxamide | 426 | C | * |
| 9 | | N-((S)-1-cyclobutylethyl)-2-(2,6-dioxopiperidin-3-yl)-1-oxoisoindoline-5-carboxamide | 370.2 | C | ** |

TABLE 1-continued
| Cmpd No. | Cmpd Structure | Cmpd Name | MH+ | DC50 | Y |
|---|---|---|---|---|---|
| 10 | 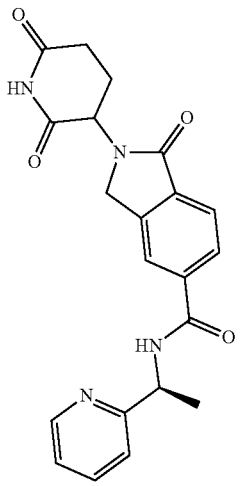 [SMILES: C[C@H](NC(=O)c1ccc2c(c1)CN(C1CCC(=O)NC1=O)C2=O)c1ccccn1] | 2-(2,6-dioxopiperidin-3-yl)-1-oxo-N-((S)-1-(pyridin-2-yl)ethyl)isoindoline-5-carboxamide | 393.1 | B | ** |
| 11 | 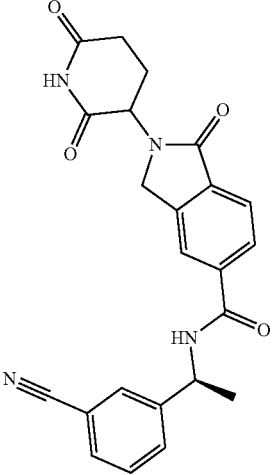 [SMILES: C[C@H](NC(=O)c1ccc2c(c1)CN(C1CCC(=O)NC1=O)C2=O)c1cccc(C#N)c1] | N-((S)-1-(3-cyanophenyl)ethyl)-2-(2,6-dioxopiperidin-3-yl)-1-oxoisoindoline-5-carboxamide | 417.1 | B | ** |
| 12 | 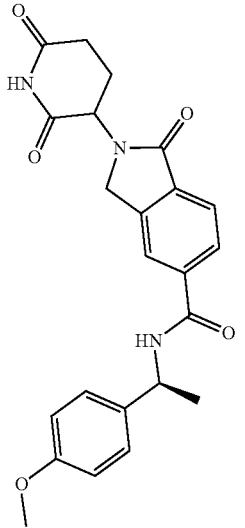 [SMILES: COc1ccc([C@H](C)NC(=O)c2ccc3c(c2)CN(C2CCC(=O)NC2=O)C3=O)cc1] | 2-(2,6-dioxopiperidin-3-yl)-N-((S)-1-(4-methoxyphenyl)ethyl)-1-oxoisoindoline-5-carboxamide | 422.2 | C | ** |

TABLE 1-continued
| Cmpd No. | Cmpd Structure | Cmpd Name | MH+ | DC$_{50}$ | Y |
|---|---|---|---|---|---|
| 13 | 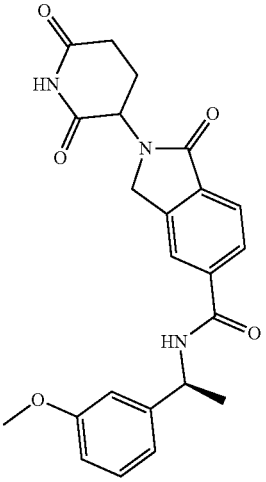 [SMILES: COc1cccc([C@H](C)NC(=O)c2ccc3c(c2)CN(C2CCC(=O)NC2=O)C3=O)c1] | 2-(2,6-dioxopiperidin-3-yl)-N-((S)-1-(3-methoxyphenyl)ethyl)-1-oxoisoindoline-5-carboxamide | 422.2 | C | ** |
| 14 | 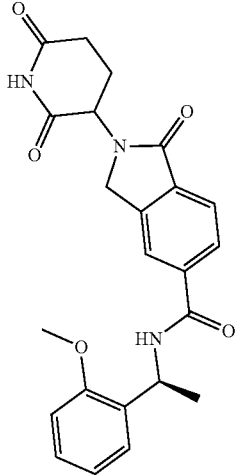 [SMILES: COc1ccccc1[C@H](C)NC(=O)c1ccc2c(c1)CN(C1CCC(=O)NC1=O)C2=O] | 2-(2,6-dioxopiperidin-3-yl)-N-((S)-1-(2-methoxyphenyl)ethyl)-1-oxoisoindoline-5-carboxamide | 422.2 | C | * |
| 15 | 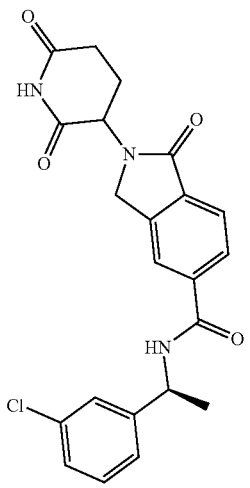 [SMILES: C[C@H](NC(=O)c1ccc2c(c1)CN(C1CCC(=O)NC1=O)C2=O)c1cccc(Cl)c1] | N-((S)-1-(3-chlorophenyl)ethyl)-2-(2,6-dioxopiperidin-3-yl)-1-oxoisoindoline-5-carboxamide | 426.1 | C | * |

TABLE 1-continued
| Cmpd No. | Cmpd Structure | Cmpd Name | MH+ | DC$_{50}$ | Y |
|---|---|---|---|---|---|
| 16 | 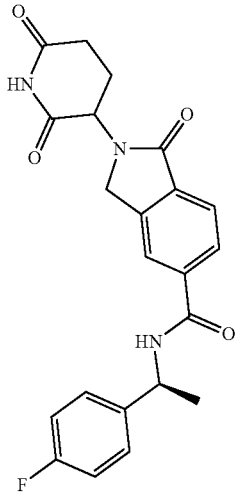 | 2-(2,6-dioxopiperidin-3-yl)-N-((S)-1-(4-fluorophenyl)ethyl)-1-oxoisoindoline-5-carboxamide | 410.1 | C | ** |
| 17 | 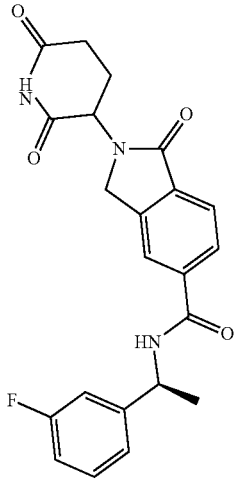 [SMILES: C[C@H](NC(=O)c1ccc2c(c1)CN(C1CCC(=O)NC1=O)C2=O)c1cccc(F)c1] | 2-(2,6-dioxopiperidin-3-yl)-N-((S)-1-(3-fluorophenyl)ethyl)-1-oxoisoindoline-5-carboxamide | 410.1 | C | ** |
| 18 | 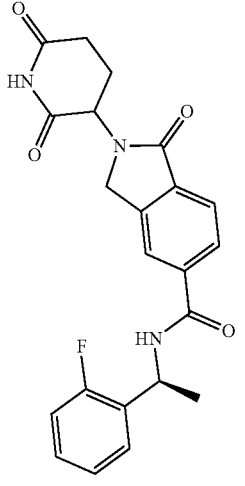 | 2-(2,6-dioxopiperidin-3-yl)-N-((S)-1-(2-fluorophenyl)ethyl)-1-oxoisoindoline-5-carboxamide | 410.1 | C | ** |

TABLE 1-continued

| Cmpd No. | Cmpd Structure | Cmpd Name | MH+ | DC$_{50}$ | Y |
|---|---|---|---|---|---|
| 19 | | 2-(2,6-dioxopiperidin-3-yl)-1-oxo-N-((S)-1-(pyridin-3-yl)ethyl)isoindoline-5-carboxamide | 393.1 | B | ** |
| 20 | | 2-(2,6-dioxopiperidin-3-yl)-1-oxo-N-((S)-1-o-tolylethyl)isoindoline-5-carboxamide | 406.2 | C | * |
| 21 | | N-((S)-1-(2-chlorophenyl)ethyl)-2-(2,6-dioxopiperidin-3-yl)-1-oxoisoindoline-5-carboxamide | 426.1 | C | * |

TABLE 1-continued

| Cmpd No. | Cmpd Structure | Cmpd Name | MH+ | DC$_{50}$ | Y |
|---|---|---|---|---|---|
| 22 | | N-((R)-1-cyclohexylethyl)-2-(2,6-dioxopiperidin-3-yl)-1-oxoisoindoline-5-carboxamide | 398.1 | A | *** |
| 23 | | N-((R)-1-cyclohexyl-2,2,2-trifluoroethyl)-2-(2,6-dioxopiperidin-3-yl)-1-oxoisoindoline-5-carboxamide | 452.2 | C | * |
| 24 | | 2-(2,6-dioxopiperidin-3-yl)-1-oxo-N-((R)-2,2,2-trifluoro-1-phenylethyl)isoindoline-5-carboxamide | 446.2 | C | * |

TABLE 1-continued

| Cmpd No. | Cmpd Structure | Cmpd Name | MH+ | DC$_{50}$ | Y |
|---|---|---|---|---|---|
| 25 | | 2-(2,6-dioxopiperidin-3-yl)-1-oxo-N-((S)-3,3,3-trifluoro-1-phenylpropyl)isoindoline-5-carboxamide | 460.2 | C | * |
| 26 | | 2-(2,6-dioxopiperidin-3-yl)-1-oxo-N-((S)-1-(tetrahydro-2H-pyran-4-yl)ethyl)isoindoline-5-carboxamide | 400.2 | B | ** |
| 27 | | N-((S)-1-cyclohexyl-2-methylpropyl)-2-(2,6-dioxopiperidin-3-yl)-1-oxoisoindoline-5-carboxamide | 426.2 | B | ** |

TABLE 1-continued

| Cmpd No. | Cmpd Structure | Cmpd Name | MH+ | DC50 | Y |
|---|---|---|---|---|---|
| 28 | | 2-(2,6-dioxopiperidin-3-yl)-N-((S)-3-methylbutan-2-yl)-1-oxoisoindoline-5-carboxamide | 358.1 | B | ** |
| 29 | | N-((S)-1-cyclohexyl-3,3,3-trifluoropropyl)-2-(2,6-dioxopiperidin-3-yl)-1-oxoisoindoline-5-carboxamide | 466.2 | C | ** |
| 30 | | N-((S)-3,3-dimethylbutan-2-yl)-2-(2,6-dioxopiperidin-3-yl)-1-oxoisoindoline-5-carboxamide | 372.3 | A | ** |

TABLE 1-continued

| Cmpd No. | Cmpd Structure | Cmpd Name | MH+ | DC$_{50}$ | Y |
|---|---|---|---|---|---|
| 31 | | 2-(2,6-dioxopiperidin-3-yl)-1-oxo-N-((R)-1,1,1-trifluoro-3-methylbutan-2-yl)isoindoline-5-carboxamide | 412.2 | B | ** |
| 32 | | 2-(2,6-dioxopiperidin-3-yl)-1-oxo-N-((R)-2,2,2-trifluoro-1-(4-fluorophenyl)ethyl)isoindoline-5-carboxamide | 464.2 | C | * |
| 33 | | 2-(2,6-dioxopiperidin-3-yl)-1-oxo-N-((R)-2,2,2-trifluoro-1-(3-methoxyphenyl)ethyl)isoindoline-5-carboxamide | 475.8 | C | * |

TABLE 1-continued

| Cmpd No. | Cmpd Structure | Cmpd Name | MH+ | DC$_{50}$ | Y |
|---|---|---|---|---|---|
| 34 | | 2-(2,6-dioxopiperidin-3-yl)-1-oxo-N-((R)-1,1,1-trifluoro-3,3-dimethylbutan-2-yl)isoindoline-5-carboxamide | 426.1 | B | ** |
| 35 | | 2-(2,6-dioxopiperidin-3-yl)-1-oxo-N-((R)-2,2,2-trifluoro-1-(4-methoxyphenyl)ethyl)isoindoline-5-carboxamide | 476 | C | * |
| 36 | | 2-(2,6-dioxopiperidin-3-yl)-1-oxo-N-((R)-2,2,2-trifluoro-1-(tetrahydro-2H-pyran-4-yl)ethyl)isoindoline-5-carboxamide | 454.1 | B | ** |

TABLE 1-continued

| Cmpd No. | Cmpd Structure | Cmpd Name | MH+ | DC$_{50}$ | Y |
|---|---|---|---|---|---|
| 37 | | 2-(2,6-dioxopiperidin-3-yl)-1-oxo-N-((R)-2,2,2-trifluoro-1-(3-fluorophenyl)ethyl)isoindoline-5-carboxamide | 426.1 | C | ** |
| 38 | | 2-(2,6-dioxopiperidin-3-yl)-1-oxo-N-((R)-2,2,2-trifluoro-1-(2-methoxyphenyl)ethyl)isoindoline-5-carboxamide | 476.1 | C | * |
| 39 | | 2-(2,6-dioxopiperidin-3-yl)-1-oxo-N-((R)-2,2,2-trifluoro-1-(pyridin-4-yl)ethyl)isoindoline-5-carboxamide | 447.1 | A | *** |

TABLE 1-continued
| Cmpd No. | Cmpd Structure | Cmpd Name | MH+ | DC50 | Y |
|---|---|---|---|---|---|
| 40 | 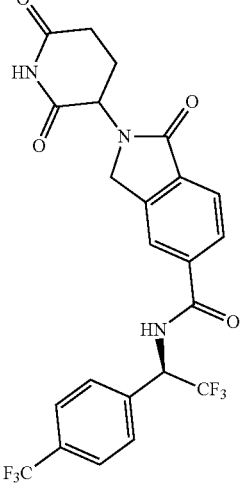 | 2-(2,6-dioxopiperidin-3-yl)-1-oxo-N-((R)-2,2,2-trifluoro-1-(4-(trifluoromethyl)phenyl)ethyl)isoindoline-5-carboxamide | 514.2 | C | * |
| 41 | 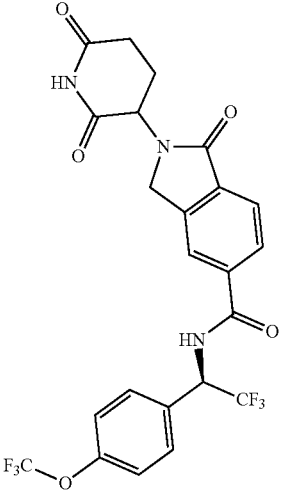 [SMILES: O=C1CCC(N2Cc3cc(C(=O)N[C@H](c4ccc(OC(F)(F)F)cc4)C(F)(F)F)ccc3C2=O)C(=O)N1] | 2-(2,6-dioxopiperidin-3-yl)-1-oxo-N-((R)-2,2,2-trifluoro-1-(4-(trifluoromethoxy)phenyl)ethyl)isoindoline-5-carboxamide | 530.2 | B | * |
| 42 | 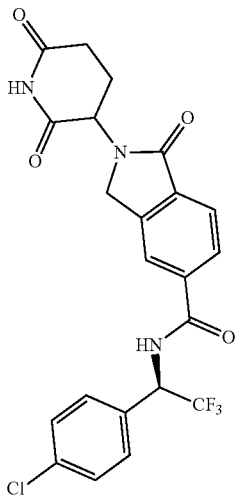 [SMILES: O=C1CCC(N2Cc3cc(C(=O)N[C@H](c4ccc(Cl)cc4)C(F)(F)F)ccc3C2=O)C(=O)N1] | N-((R)-1-(4-chlorophenyl)-2,2,2-trifluoroethyl)-2-(2,6-dioxopiperidin-3-yl)-1-oxoisoindoline-5-carboxamide | 480 | C | * |

TABLE 1-continued

| Cmpd No. | Cmpd Structure | Cmpd Name | MH+ | DC50 | Y |
|---|---|---|---|---|---|
| 43 | | N-((R)-1-(3-chlorophenyl)-2,2,2-trifluoroethyl)-2-(2,6-dioxopiperidin-3-yl)-1-oxoisoindoline-5-carboxamide | 476.3 | C | * |
| 44 | | 2-(2,6-dioxopiperidin-3-yl)-1-oxo-N-((R)-2,2,2-trifluoro-1-(2-(trifluoromethoxy)phenyl)ethyl)isoindoline-5-carboxamide | 530 | C | * |
| 45 | | N-((R)-1-(4,4-difluorocyclohexyl)-2,2,2-trifluoroethyl)-2-(2,6-dioxopiperidin-3-yl)-1-oxoisoindoline-5-carboxamide | 488.3 | B | * |

TABLE 1-continued

| Cmpd No. | Cmpd Structure | Cmpd Name | MH+ | DC$_{50}$ | Y |
|---|---|---|---|---|---|
| 46 |  | N-((R)-1-(4,4-dimethylcyclohexyl)-2,2,2-trifluoroethyl)-2-(2,6-dioxopiperidin-3-yl)-1-oxoisoindoline-5-carboxamide | 480.1 | B | * |
| 47 |  | 2-(2,6-dioxopiperidin-3-yl)-1-oxo-N-((R)-2,2,2-trifluoro-1-(2-(trifluoromethyl)phenyl)ethyl)isoindoline-5-carboxamide | 514.2 | C | * |
| 48 |  | 2-(2,6-dioxopiperidin-3-yl)-1-oxo-N-((R)-2,2,2-trifluoro-1-(pyridin-2-yl)ethyl)isoindoline-5-carboxamide | 447 | B | ** |

TABLE 1-continued

| Cmpd No. | Cmpd Structure | Cmpd Name | MH+ | DC$_{50}$ | Y |
|---|---|---|---|---|---|
| 49 | | 2-(2,6-dioxopiperidin-3-yl)-1-oxo-N-((R)-2,2,2-trifluoro-1-(2-fluorophenyl)ethyl)isoindoline-5-carboxamide | 464.1 | C | * |
| 50 | | N-((R)-1-(2-chlorophenyl)-2,2,2-trifluoroethyl)-2-(2,6-dioxopiperidin-3-yl)-1-oxoisoindoline-5-carboxamide | 480.1 | C | * |
| 51 | | N-((S)-1-(2,4-difluorophenyl)ethyl)-2-(2,6-dioxopiperidin-3-yl)-1-oxoisoindoline-5-carboxamide | 428.2 | C | * |

TABLE 1-continued

| Cmpd No. | Cmpd Structure | Cmpd Name | MH+ | DC$_{50}$ | Y |
|---|---|---|---|---|---|
| 52 | | 2-(2,6-dioxopiperidin-3-yl)-1-oxo-N-((R)-2,2,2-trifluoro-1-(3-(trifluoromethyl)phenyl)ethyl)isoindoline-5-carboxamide | 514.2 | C | * |
| 53 | | 2-(2,6-dioxopiperidin-3-yl)-1-oxo-N-((1R)-2,2,2-trifluoro-1-(spiro[3.5]nonan-7-yl)ethyl)isoindoline-5-carboxamide | 492.2 | C | * |
| 54 | | 2-(2,6-dioxopiperidin-3-yl)-1-oxo-N-((R)-2,2,2-trifluoro-1-(pyridin-3-yl)ethyl)isoindoline-5-carboxamide | 447 | B | ** |

TABLE 1-continued

| Cmpd No. | Cmpd Structure | Cmpd Name | MH⁺ | DC$_{50}$ | Y |
|---|---|---|---|---|---|
| 55 | | N-((S)-1-(4-chloro-2-fluorophenyl)ethyl)-2-(2,6-dioxopiperidin-3-yl)-1-oxoisoindoline-5-carboxamide | 444 | C | * |
| 56 | | 2-(2,6-dioxopiperidin-3-yl)-1-oxo-N-((R)-2,2,2-trifluoro-1-((1r,4R)-4-hydroxycyclohexyl)ethyl)isoindoline-5-carboxamide | 468.3 | B | * |
| 57 | | N-((R)-1-(bicyclo[1.1.1]pentan-1-yl)-2,2,2-trifluoroethyl)-2-(2,6-dioxopiperidin-3-yl)-1-oxoisoindoline-5-carboxamide | 436.1 | C | * |

TABLE 1-continued

| Cmpd No. | Cmpd Structure | Cmpd Name | MH+ | DC₅₀ | Y |
|---|---|---|---|---|---|
| 58 | | 2-(2,6-dioxopiperidin-3-yl)-1-oxo-N-((R)-2,2,2-trifluoro-1-(3-(trifluoromethoxy)phenyl)ethyl)isoindoline-5-carboxamide | 530 | C | * |
| 59 | | N-((S)-1-(2-chloro-4-fluorophenyl)ethyl)-2-(2,6-dioxopiperidin-3-yl)-1-oxoisoindoline-5-carboxamide | 444 | C | * |
| 60 | | 2-((R)-2,6-dioxopiperidin-3-yl)-1-oxo-N-((R)-2,2,2-trifluoro-1-phenylethyl)isoindoline-5-carboxamide | 446.1 | C | * |

TABLE 1-continued
| Cmpd No. | Cmpd Structure | Cmpd Name | MH+ | DC$_{50}$ | Y |
|---|---|---|---|---|---|
| 61 | 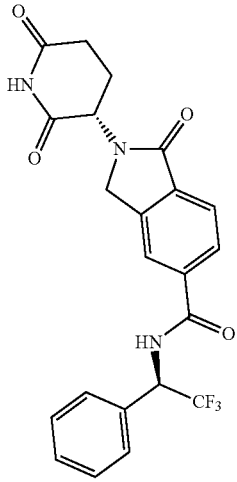 [SMILES: O=C1CC[C@H](N2Cc3cc(C(=O)N[C@H](c4ccccc4)C(F)(F)F)ccc3C2=O)C(=O)N1] | 2-((S)-2,6-dioxopiperidin-3-yl)-1-oxo-N-((R)-2,2,2-trifluoro-1-phenylethyl)isoindoline-5-carboxamide | 446.1 | C | * |
| 62 | 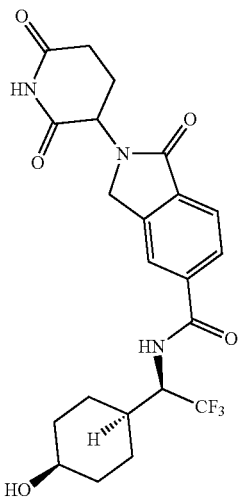 | 2-(2,6-dioxopiperidin-3-yl)-1-oxo-N-((R)-2,2,2-trifluoro-1-((1s,4S)-4-hydroxycyclohexyl)ethyl)isoindoline-5-carboxamide | 468.2 | B | * |
| 63 | 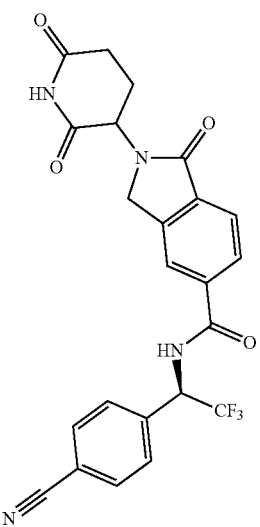 [SMILES: N#Cc1ccc([C@@H](NC(=O)c2ccc3c(c2)CN(C2CCC(=O)NC2=O)C3=O)C(F)(F)F)cc1] | N-((R)-1-(4-cyanophenyl)-2,2,2-trifluoroethyl)-2-(2,6-dioxopiperidin-3-yl)-1-oxoisoindoline-5-carboxamide | 471 | C | * |

TABLE 1-continued

| Cmpd No. | Cmpd Structure | Cmpd Name | MH+ | DC50 | Y |
|---|---|---|---|---|---|
| 64 | | N-((R)-1-(3-cyanophenyl)-2,2,2-trifluoroethyl)-2-(2,6-dioxopiperidin-3-yl)-1-oxoisoindoline-5-carboxamide | 471.1 | C | * |
| 65 | | 2-(2,6-dioxopiperidin-3-yl)-1-oxo-N-((R)-2,2,2-trifluoro-1-(1-methyl-1H-pyrazol-3-yl)ethyl)isoindoline-5-carboxamide | 450.3 | A | ** |
| 66 | | 2-(2,6-dioxopiperidin-3-yl)-1-oxo-N-((R)-2,2,2-trifluoro-1-(pyrimidin-5-yl)ethyl)isoindoline-5-carboxamide | 448 | A | ** |

TABLE 1-continued
| Cmpd No. | Cmpd Structure | Cmpd Name | MH+ | DC$_{50}$ | Y |
|---|---|---|---|---|---|
| 67 | 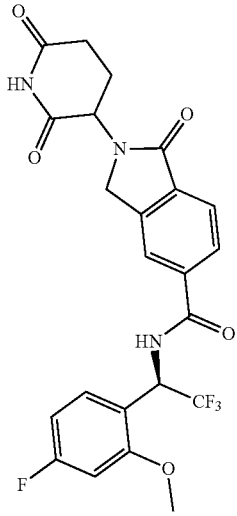 | 2-(2,6-dioxopiperidin-3-yl)-1-oxo-N-((R)-2,2,2-trifluoro-1-(4-fluoro-2-methoxyphenyl)ethyl)isoindoline-5-carboxamide | 494.1 | C | * |
| 68 | 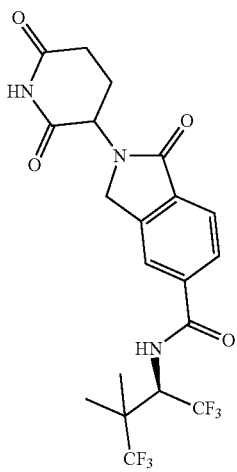 | 2-(2,6-dioxopiperidin-3-yl)-N-((R)-1,1,1,4,4,4-hexafluoro-3,3-dimethylbutan-2-yl)-1-oxoisoindoline-5-carboxamide | 480.2 | B | ** |
| 69 | 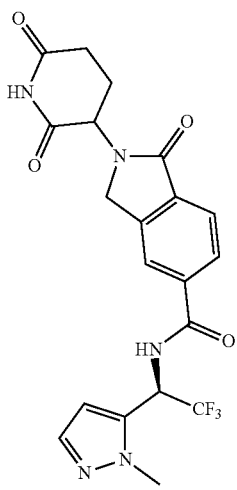 | 2-(2,6-dioxopiperidin-3-yl)-1-oxo-N-((R)-2,2,2-trifluoro-1-(1-methyl-1H-pyrazol-5-yl)ethyl)isoindoline-5-carboxamide | 450.1 | A | ** |

TABLE 1-continued
| Cmpd No. | Cmpd Structure | Cmpd Name | MH+ | DC₅₀ | Y |
|---|---|---|---|---|---|
| 70 | 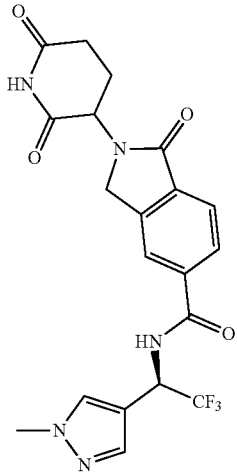 | 2-(2,6-dioxopiperidin-3-yl)-1-oxo-N-((R)-2,2,2-trifluoro-1-(1-methyl-1H-pyrazol-4-yl)ethyl)isoindoline-5-carboxamide | 450.1 | B | ** |
| 71 | 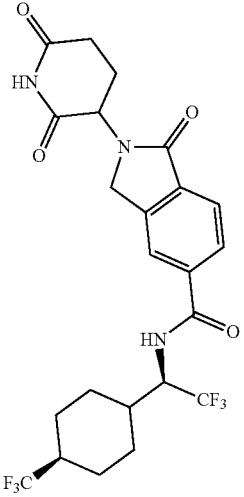 | 2-(2,6-dioxopiperidin-3-yl)-1-oxo-N-((1R)-2,2,2-trifluoro-1-(4-(trifluoromethyl)cyclohexyl)ethyl)isoindoline-5-carboxamide | 520.2 | C | * |
| 72 | 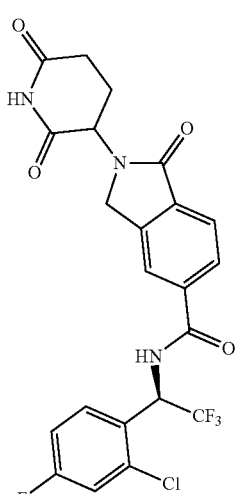 [SMILES: O=C1CCC(N2Cc3cc(C(=O)N[C@H](c4ncccc4C(F)(F)F)C(F)(F)F)ccc3C2=O)C(=O)N1] | N-((R)-1-(2-chloro-4-fluorophenyl)-2,2,2-trifluoroethyl)-2-(2,6-dioxopiperidin-3-yl)-1-oxoisoindoline-5-carboxamide | 498.1 | C | * |

TABLE 1-continued

| Cmpd No. | Cmpd Structure | Cmpd Name | MH+ | DC$_{50}$ | Y |
|---|---|---|---|---|---|
| 73 | | N-((R)-1-(3,4-difluorophenyl)-2,2,2-trifluoroethyl)-2-(2,6-dioxopiperidin-3-yl)-1-oxoisoindoline-5-carboxamide | 482.3 | C | * |
| 74 | | 2-(2,6-dioxopiperidin-3-yl)-1-oxo-N-((R)-2,2,2-trifluoro-1-(1-methylcyclobutyl)ethyl)isoindoline-5-carboxamide | 438.2 | C | * |
| 75 | | 2-(2,6-dioxopiperidin-3-yl)-1-oxo-N-((R)-2,2,2-trifluoro-1-(1-(trifluoromethyl)cyclopropyl)ethyl)isoindoline-5-carboxamide | 478 | B | ** |

TABLE 1-continued

| Cmpd No. | Cmpd Structure | Cmpd Name | MH+ | DC$_{50}$ | Y |
|---|---|---|---|---|---|
| 76 | | 2-(2,6-dioxopiperidin-3-yl)-1-oxo-N-((R)-2,2,2-trifluoro-1-(5-fluoropyridin-2-yl)ethyl)isoindoline-5-carboxamide | 465 | C | ** |
| 77 | | 2-(2,6-dioxopiperidin-3-yl)-1-oxo-N-((R)-2,2,2-trifluoro-1-(4-fluoro-2-(trifluoromethyl)phenyl)ethyl)isoindoline-5-carboxamide | 532 | C | * |
| 78 | | 2-(2,6-dioxopiperidin-3-yl)-1-oxo-N-((R)-2,2,2-trifluoro-1-(1-methylcyclopropyl)ethyl)isoindoline-5-carboxamide | 465 | C | * |

TABLE 1-continued

| Cmpd No. | Cmpd Structure | Cmpd Name | MH+ | DC50 | Y |
|---|---|---|---|---|---|
| 79 | | N-((R)-1-(4-chloro-2-fluorophenyl)-2,2,2-trifluoroethyl)-2-(2,6-dioxopiperidin-3-yl)-1-oxoisoindoline-5-carboxamide | 498 | C | * |
| 80 | | N-((R)-1-(2,4-difluorophenyl)-2,2,2-trifluoroethyl)-2-(2,6-dioxopiperidin-3-yl)-1-oxoisoindoline-5-carboxamide | 482 | C | * |
| 81 | | 2-(2,6-dioxopiperidin-3-yl)-1-oxo-N-((R)-2,2,2-trifluoro-1-(1-methylpiperidin-4-yl)ethyl)isoindoline-5-carboxamide | 467.1 | A | ** |

TABLE 1-continued

| Cmpd No. | Cmpd Structure | Cmpd Name | MH+ | DC$_{50}$ | Y |
|---|---|---|---|---|---|
| 82 | | 2-(2,6-dioxopiperidin-3-yl)-1-oxo-N-((R)-2,2,2-trifluoro-1-(pyrazin-2-yl)ethyl)isoindoline-5-carboxamide | 448 | B | ** |
| 83 | | 2-(2,6-dioxopiperidin-3-yl)-1-oxo-N-((R)-2,2,2-trifluoro-1-(1-methylcyclopentyl)ethyl)isoindoline-5-carboxamide | 452.1 | C | * |
| 84 | | 2-(2,6-dioxopiperidin-3-yl)-6-fluoro-1-oxo-N-((R)-2,2,2-trifluoro-1-phenylethyl)isoindoline-5-carboxamide | 464 | B | ** |

| Cmpd No. | Cmpd Structure | Cmpd Name | MH+ | DC$_{50}$ | Y |
|---|---|---|---|---|---|
| 85 | | 2-(2,6-dioxopiperidin-3-yl)-6-fluoro-1-oxo-N-((S)-1-phenylethyl)isoindoline-5-carboxamide | 410 | A | *** |
| 86 | | 2-(2,6-dioxopiperidin-3-yl)-1-oxo-N-((R)-2,2,2-trifluoro-1-(4-fluoro-2-(trifluoromethoxy)phenyl)ethyl)isoindoline-5-carboxamide | 548.3 | C | * |
| 87 | | N-((R)-3-cyano-1,1,1-trifluoro-3-methylbutan-2-yl)-2-(2,6-dioxopiperidin-3-yl)-1-oxoisoindoline-5-carboxamide | 437.3 | B | ** |

TABLE 1-continued

| Cmpd No. | Cmpd Structure | Cmpd Name | MH+ | DC$_{50}$ | Y |
|---|---|---|---|---|---|
| 88 | | 2-(2,6-dioxopiperidin-3-yl)-6-fluoro-1-oxo-N-((R)-2,2,2-trifluoro-1-(2-(trifluoromethyl)phenyl)ethyl)isoindoline-5-carboxamide | 532.2 | C | * |
| 89 | | 2-(2,6-dioxopiperidin-3-yl)-4-fluoro-1-oxo-N-((R)-2,2,2-trifluoro-1-phenylethyl)isoindoline-5-carboxamide | 464.2 | C | ** |
| 90 | | 2-(2,6-dioxopiperidin-3-yl)-6-fluoro-1-oxo-N-((R)-2,2,2-trifluoro-1-(3-(trifluoromethyl)phenyl)ethyl)isoindoline-5-carboxamide | 532.2 | B | ** |

TABLE 1-continued

| Cmpd No. | Cmpd Name | MH+ | DC$_{50}$ | Y |
|---|---|---|---|---|
| 91 | N-((R)-1-(4-chlorophenyl)-2,2,2-trifluoroethyl)-2-(2,6-dioxopiperidin-3-yl)-6-fluoro-1-oxoisoindoline-5-carboxamide | 498.1 | C | ** |
| 92 | 2-(2,6-dioxopiperidin-3-yl)-6-fluoro-1-oxo-N-((R)-2,2,2-trifluoro-1-(4-fluorophenyl)ethyl)isoindoline-5-carboxamide | 482.1 | B | ** |
| 93 | N-((R)-1-(4-chlorophenyl)-2,2,2-trifluoroethyl)-2-(2,6-dioxopiperidin-3-yl)-4-fluoro-1-oxoisoindoline-5-carboxamide | 498.3 | C | * |

TABLE 1-continued

| Cmpd No. | Cmpd Structure | Cmpd Name | MH+ | DC$_{50}$ | Y |
|---|---|---|---|---|---|
| 94 | | 2-(2,6-dioxopiperidin-3-yl)-1-oxo-N-((R)-2,2,2-trifluoro-1-(3-methyloxetan-3-yl)ethyl)isoindoline-5-carboxamide | 440.3 | B | ** |
| 95 | | 2-(2,6-dioxopiperidin-3-yl)-1-oxo-N-((R)-1,1,1-trifluoro-4-hydroxy-3,3-dimethylbutan-2-yl)isoindoline-5-carboxamide | 442.2 | A | ** |
| 96 | | 2-(2,6-dioxopiperidin-3-yl)-4-fluoro-1-oxo-N-((R)-2,2,2-trifluoro-1-(4-fluorophenyl)ethyl)isoindoline-5-carboxamide | 481 | C | * |

TABLE 1-continued

| Cmpd No. | Cmpd Structure | Cmpd Name | MH+ | DC$_{50}$ | Y |
|---|---|---|---|---|---|
| 97 | | 2-(2,6-dioxopiperidin-3-yl)-4-fluoro-1-oxo-N-((R)-2,2,2-trifluoro-1-(3-(trifluoromethyl)phenyl)ethyl)isoindoline-5-carboxamide | 532.3 | B | ** |
| 98 | | 2-(2,6-dioxopiperidin-3-yl)-4-fluoro-1-oxo-N-((R)-2,2,2-trifluoro-1-(2-(trifluoromethyl)phenyl)ethyl)isoindoline-5-carboxamide | 532.3 | C | * |
| 99 | | 2-(2,6-dioxopiperidin-3-yl)-6-fluoro-1-oxo-N-((R)-2,2,2-trifluoro-1-(2-fluorophenyl)ethyl)isoindoline-5-carboxamide | 482.3 | B | ** |

TABLE 1-continued

| Cmpd No. | Cmpd Structure | Cmpd Name | MH⁺ | DC$_{50}$ | Y |
|---|---|---|---|---|---|
| 100 | | 2-(2,6-dioxopiperidin-3-yl)-4-fluoro-1-oxo-N-((R)-2,2,2-trifluoro-1-(2-fluorophenyl)ethyl)isoindoline-5-carboxamide | 482.2 | B | * |
| 101 | | 2-(2,6-dioxopiperidin-3-yl)-1-oxo-N-((R)-2,2,2-trifluoro-1-(4-hydroxyphenyl)ethyl)isoindoline-5-carboxamide | 462 | C | * |
| 102 | | 2-(2,6-dioxopiperidin-3-yl)-1-oxo-N-((R)-2,2,2-trifluoro-1-(3-isopropoxyphenyl)ethyl)isoindoline-5-carboxamide | 504.2 | C | ** |

TABLE 1-continued

| Cmpd No. | Cmpd Structure | Cmpd Name | MH+ | DC$_{50}$ | Y |
|---|---|---|---|---|---|
| 103 | | 2-((S)-2,6-dioxopiperidin-3-yl)-1-oxo-N-((R)-2,2,2-trifluoro-1-(4-fluorophenyl)ethyl)isoindoline-5-carboxamide | 464.4 | C | * |
| 104 | | 2-((R)-2,6-dioxopiperidin-3-yl)-1-oxo-N-((R)-2,2,2-trifluoro-1-(4-fluorophenyl)ethyl)isoindoline-5-carboxamide | 464.3 | C | * |
| 105 | | N-((R)-1-(2,4-difluorophenyl)-2,2,2-trifluoroethyl)-2-(2,6-dioxopiperidin-3-yl)-4-fluoro-1-oxoisoindoline-5-carboxamide | 500.2 | C | * |

TABLE 1-continued

| Cmpd No. | Cmpd Name | MH+ | DC$_{50}$ | Y |
|---|---|---|---|---|
| 106 | N-((R)-1-(3-chloropyridin-2-yl)-2,2,2-trifluoroethyl)-2-(2,6-dioxopiperidin-3-yl)-1-oxoisoindoline-5-carboxamide | 481.2 | C | * |
| 107 | N-((R)-1-(3-chlorophenyl)-2,2,2-trifluoroethyl)-2-(2,6-dioxopiperidin-3-yl)-4-fluoro-1-oxoisoindoline-5-carboxamide | 498.1 | B | ** |
| 108 | 2-(2,6-dioxopiperidin-3-yl)-4-fluoro-1-oxo-N-((R)-2,2,2-trifluoro-1-(3-fluorophenyl)ethyl)isoindoline-5-carboxamide | 482.1 | B | ** |

TABLE 1-continued

| Cmpd No. | Cmpd Structure | Cmpd Name | MH+ | DC$_{50}$ | Y |
|---|---|---|---|---|---|
| 109 | | N-((R)-1-(5-chloropyridin-2-yl)-2,2,2-trifluoroethyl)-2-(2,6-dioxopiperidin-3-yl)-1-oxoisoindoline-5-carboxamide | 481.2 | C | * |
| 110 | | 2-(2,6-dioxopiperidin-3-yl)-1-oxo-N-((R)-2,2,2-trifluoro-1-(3-fluoropyridin-2-yl)ethyl)isoindoline-5-carboxamide | 465.2 | C | * |
| 111 | | N-((R)-2,2-difluoro-1-(4-fluorophenyl)ethyl)-2-(2,6-dioxopiperidin-3-yl)-1-oxoisoindoline-5-carboxamide | 446.3 | C | * |

TABLE 1-continued

| Cmpd No. | Cmpd Structure | Cmpd Name | MH+ | DC$_{50}$ | Y |
|---|---|---|---|---|---|
| 112 | | N-((R)-2,2-difluoro-1-(4-fluorophenyl)ethyl)-2-(2,6-dioxopiperidin-3-yl)-4-fluoro-1-oxoisoindoline-5-carboxamide | 464.3 | C | * |
| 113 | | N-((R)-1-(3,4-difluorophenyl)-2,2,2-trifluoroethyl)-2-(2,6-dioxopiperidin-3-yl)-4-fluoro-1-oxoisoindoline-5-carboxamide | 500.1 | B | ** |
| 114 | | N-((R)-1-(2-chlorophenyl)-2,2,2-trifluoroethyl)-2-(2,6-dioxopiperidin-3-yl)-4-fluoro-1-oxoisoindoline-5-carboxamide | 498.1 | C | * |

TABLE 1-continued

| Cmpd No. | Cmpd Structure | Cmpd Name | MH+ | DC$_{50}$ | Y |
|---|---|---|---|---|---|
| 115 | | 2-(2,6-dioxopiperidin-3-yl)-4-fluoro-1-oxo-N-((R)-2,2,2-trifluoro-1-(5-fluoropyridin-2-yl)ethyl)isoindoline-5-carboxamide | 483.1 | B | ** |
| 116 | | 2-(2,6-dioxopiperidin-3-yl)-1-oxo-N-((R)-2,2,2-trifluoro-1-(3-(trifluoromethyl)pyridin-2-yl)ethyl)isoindoline-5-carboxamide | 515.1 | B | ** |
| 117 | | 2-(2,6-dioxopiperidin-3-yl)-4-fluoro-1-oxo-N-((R)-2,2,2-trifluoro-1-(3-fluoropyridin-2-yl)ethyl)isoindoline-5-carboxamide | 483.1 | B | ** |

TABLE 1-continued

| Cmpd No. | Cmpd Structure | Cmpd Name | MH+ | DC$_{50}$ | Y |
|---|---|---|---|---|---|
| 118 | | 2-(2,6-dioxopiperidin-3-yl)-1-oxo-N-((R)-1-phenylpropyl)isoindoline-5-carboxamide | 406.1 | B | ** |
| 119 | | 2-(2,6-dioxopiperidin-3-yl)-1-oxo-N-((R)-2,2,2-trifluoro-1-(4-(trifluoromethyl)pyridin-2-yl)ethyl)isoindoline-5-carboxamide | 515.1 | C | ** |
| 120 | | 2-(2,6-dioxopiperidin-3-yl)-4-fluoro-1-oxo-N-((R)-2,2,2-trifluoro-1-(3-(trifluoromethoxy)phenyl)ethyl)isoindoline-5-carboxamide | 548.2 | B | ** |

TABLE 1-continued

| Cmpd No. | Cmpd Structure | Cmpd Name | MH+ | DC$_{50}$ | Y |
|---|---|---|---|---|---|
| 121 | | N-((R)-1-cyclohexyl-2,2,2-trifluoroethyl)-2-(2,6-dioxopiperidin-3-yl)-4-fluoro-1-oxoisoindoline-5-carboxamide | 470.3 | C | * |
| 122 | | N-((R)-1-(3-cyclopropoxyphenyl)-2,2,2-trifluoroethyl)-2-(2,6-dioxopiperidin-3-yl)-1-oxoisoindoline-5-carboxamide | 502.2 | C | * |
| 123 | | 2-(2,6-dioxopiperidin-3-yl)-1-oxo-N-((S)-3,3,3-trifluoro-1-(4-fluorophenyl)propyl)isoindoline-5-carboxamide | 478.2 | B | ** |

TABLE 1-continued

| Cmpd No. | Cmpd Structure | Cmpd Name | MH+ | DC$_{50}$ | Y |
|---|---|---|---|---|---|
| 124 | | 2-(2,6-dioxopiperidin-3-yl)-N-((R)-2-methyl-1-phenylpropyl)-1-oxoisoindoline-5-carboxamide | 420.3 | C | * |
| 125 | | 2-(2,6-dioxopiperidin-3-yl)-1-oxo-N-((R)-2,2,2-trifluoro-1-(6-(trifluoromethyl)pyridin-2-yl)ethyl)isoindoline-5-carboxamide | 515.1 | C | * |
| 126 | | 2-(2,6-dioxopiperidin-3-yl)-1-oxo-N-((R)-2,2,2-trifluoro-1-(5-(trifluoromethyl)pyridin-2-yl)ethyl)isoindoline-5-carboxamide | 515.1 | C | ** |

TABLE 1-continued

| Cmpd No. | Cmpd Structure | Cmpd Name | MH+ | DC₅₀ | Y |
|---|---|---|---|---|---|
| 127 | | N-((R)-1-(5-chloro-3-fluoropyridin-2-yl)-2,2,2-trifluoroethyl)-2-(2,6-dioxopiperidin-3-yl)-1-oxoisoindoline-5-carboxamide | 499 | C | * |
| 128 | | 2-(2,6-dioxopiperidin-3-yl)-4-fluoro-1-oxo-N-((R)-2,2,2-trifluoro-1-o-tolylethyl)isoindoline-5-carboxamide | 478.2 | C | * |
| 129 | | N-((S)-1-(4-chlorophenyl)-3,3,3-trifluoropropyl)-2-(2,6-dioxopiperidin-3-yl)-4-fluoro-1-oxoisoindoline-5-carboxamide | 512.3 | A | *** |

TABLE 1-continued

| Cmpd No. | Cmpd Structure | Cmpd Name | MH+ | DC$_{50}$ | Y |
|---|---|---|---|---|---|
| 130 | | N-((R)-1-(4-cyclopropoxyphenyl)-2,2,2-trifluoroethyl)-2-(2,6-dioxopiperidin-3-yl)-4-fluoro-1-oxoisoindoline-5-carboxamide | 520.2 | B | ** |
| 131 | | N-((R)-1-(2-cyanophenyl)ethyl)-2-(2,6-dioxopiperidin-3-yl)-1-oxoisoindoline-5-carboxamide | 417.2 | C | ** |
| 132 | | N-((R)-1-cyclopentylethyl)-2-(2,6-dioxopiperidin-3-yl)-1-oxoisoindoline-5-carboxamide | 384.1 | B | ** |

TABLE 1-continued

| Cmpd No. | Cmpd Structure | Cmpd Name | MH+ | DC$_{50}$ | Y |
|---|---|---|---|---|---|
| 133 | | N-((R)-1-(3,5-difluoropyridin-2-yl)-2,2,2-trifluoroethyl)-2-(2,6-dioxopiperidin-3-yl)-1-oxoisoindoline-5-carboxamide | 483.1 | C | * |
| 134 | | 2-(2,6-dioxopiperidin-3-yl)-4-fluoro-1-oxo-N-((R)-2,2,2-trifluoro-1-m-tolylethyl)isoindoline-5-carboxamide | 478.2 | C | ** |
| 135 | | 2-(2,6-dioxopiperidin-3-yl)-4-fluoro-1-oxo-N-((R)-2,2,2-trifluoro-1-(4-(trifluoromethoxy)phenyl)ethyl)isoindoline-5-carboxamide | 548.1 | B | ** |

TABLE 1-continued

| Cmpd No. | Cmpd Structure | Cmpd Name | MH+ | DC$_{50}$ | Y |
|---|---|---|---|---|---|
| 136 | | 2-(2,6-dioxopiperidin-3-yl)-4-fluoro-1-oxo-N-((R)-2,2,2-trifluoro-1-(2-(trifluoromethoxy)phenyl)ethyl)isoindoline-5-carboxamide | 548.1 | C | * |
| 137 | | N-((R)-1-cyclopentyl-2,2,2-trifluoroethyl)-2-(2,6-dioxopiperidin-3-yl)-4-fluoro-1-oxoisoindoline-5-carboxamide | 456.2 | C | * |
| 138 | | N-((R)-1-(bicyclo[1.1.1]pentan-1-yl)-2,2,2-trifluoroethyl)-2-(2,6-dioxopiperidin-3-yl)-4-fluoro-1-oxoisoindoline-5-carboxamide | 454.2 | C | * |

TABLE 1-continued

| Cmpd No. | Cmpd Name | MH+ | DC$_{50}$ | Y |
|---|---|---|---|---|
| 139 | N-((R)-1-(3-chloropyridin-2-yl)-2,2,2-trifluoroethyl)-2-(2,6-dioxopiperidin-3-yl)-4-fluoro-1-oxoisoindoline-5-carboxamide | 498.6 | C | * |
| 140 | 2-(2,6-dioxopiperidin-3-yl)-1-oxo-N-((R)-2,2,2-trifluoro-1-(3-(morpholinomethyl)phenyl)ethyl)isoindoline-5-carboxamide | 545.3 | C | * |
| 141 | N-((R)-1-(4-((dimethylamino)methyl)phenyl)-2,2,2-trifluoroethyl)-2-(2,6-dioxopiperidin-3-yl)-1-oxoisoindoline-5-carboxamide | 503.3 | C | * |

TABLE 1-continued

| Cmpd No. | Cmpd Structure | Cmpd Name | MH+ | DC$_{50}$ | Y |
|---|---|---|---|---|---|
| 142 | | 2-(2,6-dioxopiperidin-3-yl)-1-oxo-N-((R)-2,2,2-trifluoro-1-(4-(morpholinomethyl)phenyl)ethyl)isoindoline-5-carboxamide | 545.2 | C | * |
| 143 | | 2-(2,6-dioxopiperidin-3-yl)-1-oxo-N-((R)-2,2,2-trifluoro-1-(1-(2,2,2-trifluoroethyl)piperidin-4-yl)ethyl)isoindoline-5-carboxamide | 535.2 | B | * |
| 144 | | 2-(2,6-dioxopiperidin-3-yl)-4-fluoro-1-oxo-N-((R)-2,2,2-trifluoro-1-p-tolylethyl)isoindoline-5-carboxamide | 478.1 | B | * |

TABLE 1-continued

| Cmpd No. | Cmpd Structure | Cmpd Name | MH+ | DC₅₀ | Y |
|---|---|---|---|---|---|
| 145 | | N-((R)-1-(2-chloro-4-fluorophenyl)-2,2,2-trifluoroethyl)-2-(2,6-dioxopiperidin-3-yl)-4-fluoro-1-oxoisoindoline-5-carboxamide | 516.2 | C | * |
| 146 | | 2-(2,6-dioxopiperidin-3-yl)-4-fluoro-1-oxo-N-((S)-3,3,3-trifluoro-1-(3-fluorophenyl)propyl)isoindoline-5-carboxamide | 496.1 | B | ** |
| 147 | | 2-(2,6-dioxopiperidin-3-yl)-1-oxo-N-((R)-2,2,2-trifluoro-1-(4-phenoxyphenyl)ethyl)isoindoline-5-carboxamide | 538.2 | B | ** |

TABLE 1-continued

| Cmpd No. | Cmpd Structure | Cmpd Name | MH+ | DC$_{50}$ | Y |
|---|---|---|---|---|---|
| 148 | | N-((R)-1-(4-cyclopropoxyphenyl)-2,2,2-trifluoroethyl)-2-(2,6-dioxopiperidin-3-yl)-1-oxoisoindoline-5-carboxamide | 502.2 | C | * |
| 149 | | N-((S)-1-(4-chlorophenyl)-3,3,3-trifluoropropyl)-2-(2,6-dioxopiperidin-3-yl)-1-oxoisoindoline-5-carboxamide | 494.1 | A | ** |
| 150 | | N-((R)-1-(3-((dimethylamino)methyl)phenyl)-2,2,2-trifluoroethyl)-2-(2,6-dioxopiperidin-3-yl)-1-oxoisoindoline-5-carboxamide | 503.3 | B | ** |

TABLE 1-continued

| Cmpd No. | Cmpd Structure | Cmpd Name | MH+ | DC$_{50}$ | Y |
|---|---|---|---|---|---|
| 151 | | N-((R)-1-(2-chloro-6-fluorophenyl)-2,2,2-trifluoroethyl)-2-(2,6-dioxopiperidin-3-yl)-1-oxoisoindoline-5-carboxamide | 498.1 | C | * |
| 152 | | N-((R)-1-(2-chloro-3-fluorophenyl)-2,2,2-trifluoroethyl)-2-(2,6-dioxopiperidin-3-yl)-1-oxoisoindoline-5-carboxamide | 498.1 | C | * |
| 153 | | 4-chloro-2-(2,6-dioxopiperidin-3-yl)-1-oxo-N-((R)-2,2,2-trifluoro-1-(4-fluorophenyl)ethyl)isoindoline-5-carboxamide | 498 | B | ** |

TABLE 1-continued

| Cmpd No. | Cmpd Structure | Cmpd Name | MH+ | DC$_{50}$ | Y |
|---|---|---|---|---|---|
| 154 | | 2-(2,6-dioxopiperidin-3-yl)-N-((S)-2-methyl-1-phenylpropyl)-1-oxoisoindoline-5-carboxamide | 420.2 | C | * |
| 155 | | 2-(2,6-dioxopiperidin-3-yl)-1-oxo-N-((R)-2,2,2-trifluoro-1-(2-(morpholinomethyl)phenyl)ethyl)isoindoline-5-carboxamide | 545.2 | C | * |
| 156 | | 2-(2,6-dioxopiperidin-3-yl)-1-oxo-N-((R)-2,2,2-trifluoro-1-((1r,4R)-4-hydroxy-4-methylcyclohexyl)ethyl)isoindoline-5-carboxamide | 482.2 | B | * |

TABLE 1-continued

| Cmpd No. | Cmpd Structure | Cmpd Name | MH+ | DC$_{50}$ | Y |
| --- | --- | --- | --- | --- | --- |
| 157 | | N-((R)-1-(2-cyclopropoxyphenyl)-2,2,2-trifluoroethyl)-2-(2,6-dioxopiperidin-3-yl)-4-fluoro-1-oxoisoindoline-5-carboxamide | 520.2 | C | ** |
| 158 | | 2-(2,6-dioxopiperidin-3-yl)-1-oxo-N-((R)-2,2,2-trifluoro-1-(3-phenoxyphenyl)ethyl)isoindoline-5-carboxamide | 538.2 | C | * |

TABLE 1-continued
| Cmpd No. | Cmpd Structure | Cmpd Name | MH+ | DC50 | Y |
|---|---|---|---|---|---|
| 159 | 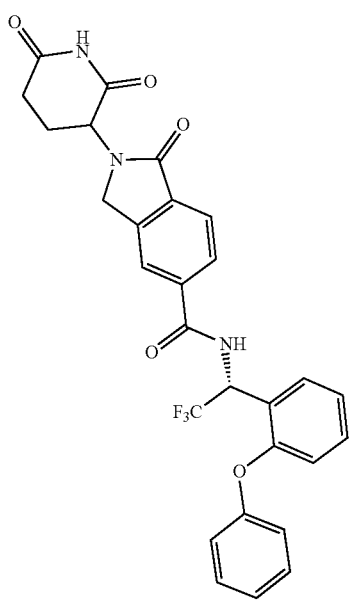 [SMILES: O=C1CCC(N2Cc3cc(C(=O)N[C@H](c4ccccc4Oc4ccccc4)C(F)(F)F)ccc3C2=O)C(=O)N1] | 2-(2,6-dioxopiperidin-3-yl)-1-oxo-N-((R)-2,2,2-trifluoro-1-(2-phenoxyphenyl)ethyl)isoindoline-5-carboxamide | 538.2 | C | * |
| 160 | 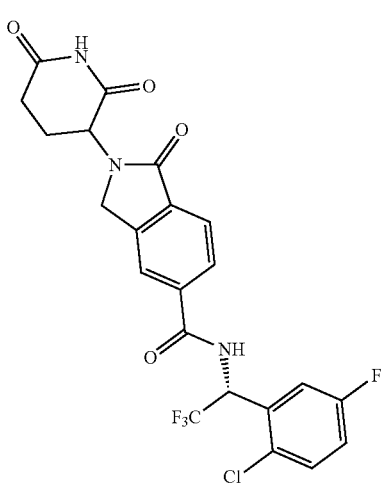 [SMILES: O=C1CCC(N2Cc3cc(C(=O)N[C@H](c4cc(F)ccc4Cl)C(F)(F)F)ccc3C2=O)C(=O)N1] | N-((R)-1-(2-chloro-5-fluorophenyl)-2,2,2-trifluoroethyl)-2-(2,6-dioxopiperidin-3-yl)-1-oxoisoindoline-5-carboxamide | 498.1 | C | * |

TABLE 1-continued
| Cmpd No. | Cmpd Structure | Cmpd Name | MH+ | DC$_{50}$ | Y |
|---|---|---|---|---|---|
| 161 | 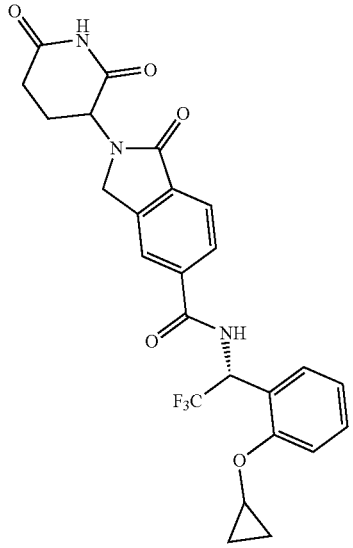 [SMILES: O=C1CCC(N2Cc3cc(C(=O)N[C@H](c4ccccc4OC4CC4)C(F)(F)F)ccc3C2=O)C(=O)N1] | N-((R)-1-(2-cyclopropoxyphenyl)-2,2,2-trifluoroethyl)-2-(2,6-dioxopiperidin-3-yl)-1-oxoisoindoline-5-carboxamide | 502.1 | C | * |
| 162 | 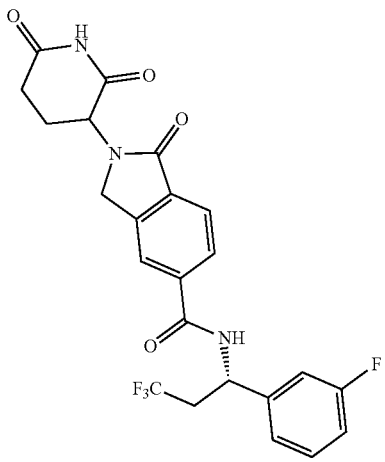 [SMILES: O=C1CCC(N2Cc3cc(C(=O)N[C@@H](CC(F)(F)F)c4cccc(F)c4)ccc3C2=O)C(=O)N1] | 2-(2,6-dioxopiperidin-3-yl)-1-oxo-N-((S)-3,3,3-trifluoro-1-(3-fluorophenyl)propyl)isoindoline-5-carboxamide | 478.2 | B | ** |
| 163 | 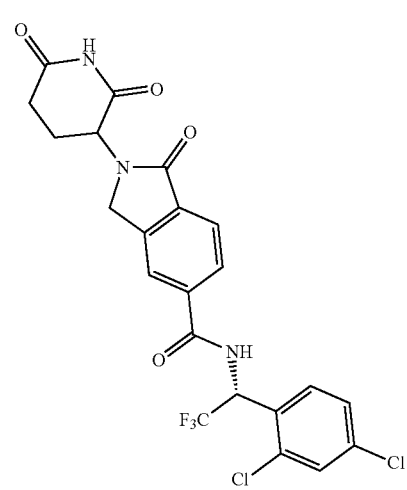 [SMILES: O=C1CCC(N2Cc3cc(C(=O)N[C@H](c4ccc(Cl)cc4Cl)C(F)(F)F)ccc3C2=O)C(=O)N1] | N-((R)-1-(2,4-dichlorophenyl)-2,2,2-trifluoroethyl)-2-(2,6-dioxopiperidin-3-yl)-1-oxoisoindoline-5-carboxamide | 514 | C | * |

TABLE 1-continued

| Cmpd No. | Cmpd Structure | Cmpd Name | MH+ | DC$_{50}$ | Y |
|---|---|---|---|---|---|
| 164 | | N-((R)-1-(2,4-dichlorophenyl)-2,2,2-trifluoroethyl)-2-(2,6-dioxopiperidin-3-yl)-4-fluoro-1-oxoisoindoline-5-carboxamide | 532 | B | ** |
| 165 | | 2-(2,6-dioxopiperidin-3-yl)-1-oxo-N-((R)-2,2,2-trifluoro-1-(3-(2-hydroxypropan-2-yl)bicyclo[1.1.1]pentan-1-yl)ethyl)isoindoline-5-carboxamide | 494.1 | C | * |
| 166 | | 2-(2,6-dioxopiperidin-3-yl)-1-oxo-N-((1R)-2,2,2-trifluoro-1-(spiro[2.5]octan-6-yl)ethyl)isoindoline-5-carboxamide | 478.2 | C | * |

TABLE 1-continued

| Cmpd No. | Cmpd Structure | Cmpd Name | MH+ | DC$_{50}$ | Y |
|---|---|---|---|---|---|
| 167 | | 2-(2,6-dioxopiperidin-3-yl)-N-((S)-1-(2-fluorophenyl)-2-methylpropyl)-1-oxoisoindoline-5-carboxamide | 438.3 | C | * |
| 168 | | 2-(2,6-dioxopiperidin-3-yl)-1-oxo-N-((R)-2,2,2-trifluoro-1-((1s,4S)-4-hydroxy-4-methylcyclohexyl)ethyl)isoindoline-5-carboxamide | 482.2 | C | * |
| 169 | | N-((S)-1-(2-chlorophenyl)-2-methylpropyl)-2-(2,6-dioxopiperidin-3-yl)-1-oxoisoindoline-5-carboxamide | 454.2 | C | * |

TABLE 1-continued

| Cmpd No. | Cmpd Structure | Cmpd Name | MH+ | DC$_{50}$ | Y |
|---|---|---|---|---|---|
| 170 | | 2-(2,6-dioxopiperidin-3-yl)-N-((S)-1-(4-fluorophenyl)-2-methylpropyl)-1-oxoisoindoline-5-carboxamide | 438.3 | C | * |
| 171 | | N-((R)-1-(3-chloropyridin-2-yl)-2-methylpropyl)-2-(2,6-dioxopiperidin-3-yl)-1-oxoisoindoline-5-carboxamide | 455.1 | B | ** |
| 172 | | N-((S)-1-(3-chloropyridin-2-yl)-2-methylpropyl)-2-(2,6-dioxopiperidin-3-yl)-1-oxoisoindoline-5-carboxamide | 455.3 | C | * |

TABLE 1-continued

| Cmpd No. | Cmpd Structure | Cmpd Name | MH+ | DC50 | Y |
|---|---|---|---|---|---|
| 173 | | N-((R)-1-(3-chloropyridin-2-yl)-2,2,2-trifluoroethyl)-2-((S)-2,6-dioxopiperidin-3-yl)-1-oxoisoindoline-5-carboxamide | 480.8 | C | * |
| 174 | | N-(2,2-difluoro-1-(4-fluorophenyl)propyl)-2-(2,6-dioxopiperidin-3-yl)-1-oxoisoindoline-5-carboxamide | 460.2 | C | * |
| 175 | | N-((R)-1-(3-chloro-5-fluoropyridin-2-yl)-2,2,2-trifluoroethyl)-2-(2,6-dioxopiperidin-3-yl)-1-oxoisoindoline-5-carboxamide | 499 | C | * |

TABLE 1-continued

| Cmpd No. | Cmpd Structure | Cmpd Name | MH+ | DC$_{50}$ | Y |
|---|---|---|---|---|---|
| 176 | | 2-(2,6-dioxopiperidin-3-yl)-1-oxo-N-(2,2,2-trifluoro-1-(2-hydroxyspiro[3.5]nonan-7-yl)ethyl)isoindoline-5-carboxamide | 508.3 | B | * |
| 177 | | N-((S)-1-(4-chlorophenyl)-2-methylpropyl)-2-(2,6-dioxopiperidin-3-yl)-1-oxoisoindoline-5-carboxamide | 454.1 | C | * |
| 178 | | N-((R)-1-(3,5-dichloropyridin-2-yl)-2,2,2-trifluoroethyl)-2-(2,6-dioxopiperidin-3-yl)-4-fluoro-1-oxoisoindoline-5-carboxamide | 533.1 | C | * |

TABLE 1-continued

| Cmpd No. | Cmpd Structure | Cmpd Name | MH+ | DC50 | Y |
|---|---|---|---|---|---|
| 179 | | N-((1R)-1-(4-(2-oxa-6-azaspiro[3.3]heptan-6-ylmethyl)phenyl)-2,2,2-trifluoroethyl)-2-(2,6-dioxopiperidin-3-yl)-1-oxoisoindoline-5-carboxamide | 557.3 | B | * |
| 180 | | 2-(2,6-dioxopiperidin-3-yl)-1-oxo-N-((R)-2,2,2-trifluoro-1-(4-(pyrrolidin-1-ylmethyl)phenyl)ethyl)isoindoline-5-carboxamide | 529.3 | C | * |
| 181 | | 2-(2,6-dioxopiperidin-3-yl)-1-oxo-N-(2,2,2-trifluoro-1-(2-hydroxyspiro[3.5]nonan-7-yl)ethyl)isoindoline-5-carboxamide | 508.3 | B | * |

TABLE 1-continued

| Cmpd No. | Cmpd Structure | Cmpd Name | MH+ | DC$_{50}$ | Y |
|---|---|---|---|---|---|
| 182 | | N-((R)-1-(3-chloropyridin-2-yl)-2,2,2-trifluoroethyl)-2-((R)-2,6-dioxopiperidin-3-yl)-1-oxoisoindoline-5-carboxamide | 481.1 | C | * |
| 183 | | N-((R)-1-(3-chloro-5-fluoropyridin-2-yl)-2,2,2-trifluoroethyl)-2-(2,6-dioxopiperidin-3-yl)-4-fluoro-1-oxoisoindoline-5-carboxamide | 517 | C | * |
| 184 | | N-((R)-1-(3,5-dichloropyridin-2-yl)-2,2,2-trifluoroethyl)-2-(2,6-dioxopiperidin-3-yl)-1-oxoisoindoline-5-carboxamide | 515 | C | * |

TABLE 1-continued
| Cmpd No. | Cmpd Structure | Cmpd Name | MH+ | DC50 | Y |
|---|---|---|---|---|---|
| 185 | 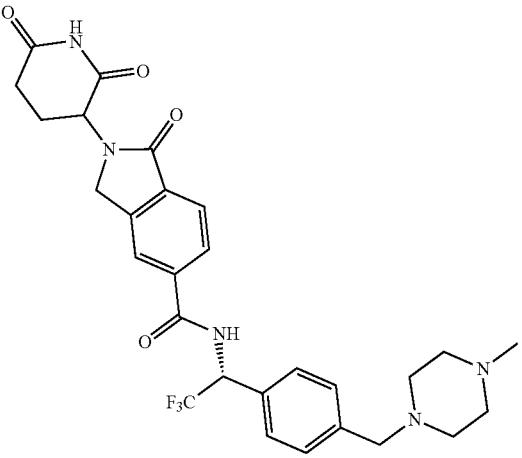 [SMILES: CN1CCN(Cc2ccc([C@@H](NC(=O)c3ccc4c(c3)CN(C3CCC(=O)NC3=O)C4=O)C(F)(F)F)cc2)CC1] | 2-(2,6-dioxopiperidin-3-yl)-1-oxo-N-((R)-2,2,2-trifluoro-1-(4-((4-methylpiperazin-1-yl)methyl)phenyl)ethyl)isoindoline-5-carboxamide | 558.3 | B | * |
| 186 | 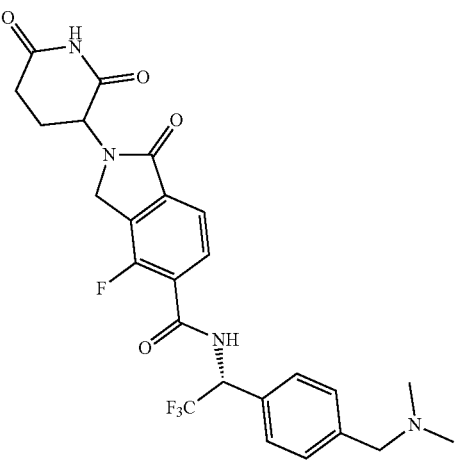 [SMILES: CN(C)Cc1ccc([C@@H](NC(=O)c2ccc3c(c2F)CN(C2CCC(=O)NC2=O)C3=O)C(F)(F)F)cc1] | N-((R)-1-(4-((dimethylamino)methyl)phenyl)-2,2,2-trifluoroethyl)-2-(2,6-dioxopiperidin-3-yl)-4-fluoro-1-oxoisoindoline-5-carboxamide | 521.3 | C | * |
| 187 | 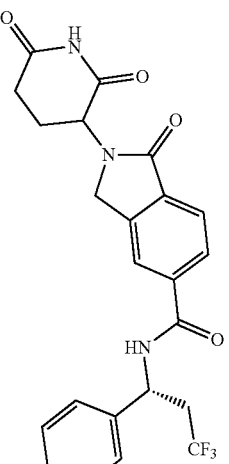 | 2-(2,6-dioxopiperidin-3-yl)-1-oxo-N-((R)-3,3,3-trifluoro-1-phenylpropyl)isoindoline-5-carboxamide | 460.2 | B | ** |

TABLE 1-continued

| Cmpd No. | Cmpd Structure | Cmpd Name | MH+ | DC50 | Y |
|---|---|---|---|---|---|
| 188 | | N-((R)-1-(4-((3,3-difluoroazetidin-1-yl)methyl)phenyl)-2,2,2-trifluoroethyl)-2-(2,6-dioxopiperidin-3-yl)-1-oxoisoindoline-5-carboxamide | 551.3 | B | ** |
| 189 | | N-((R)-1-(4-(azetidin-1-ylmethyl)phenyl)-2,2,2-trifluoroethyl)-2-(2,6-dioxopiperidin-3-yl)-1-oxoisoindoline-5-carboxamide | 515.2 | C | * |
| 190 | | 2-(2,6-dioxopiperidin-3-yl)-1-oxo-N-((R)-3,3,3-trifluoro-1-(3-fluorophenyl)propyl)isoindoline-5-carboxamide | 478.1 | C | ** |

TABLE 1-continued
| Cmpd No. | Cmpd Structure | Cmpd Name | MH+ | DC50 | Y |
|---|---|---|---|---|---|
| 191 | 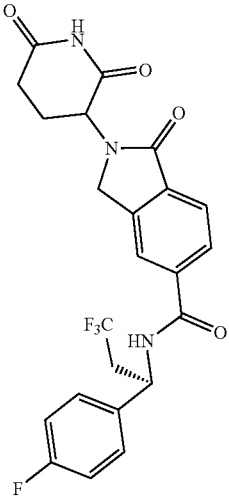 [SMILES: O=C1CCC(N2Cc3cc(C(=O)N[C@H](CC(F)(F)F)c4ccc(F)cc4)ccc3C2=O)C(=O)N1] | 2-(2,6-dioxopiperidin-3-yl)-1-oxo-N-((R)-3,3,3-trifluoro-1-(4-fluorophenyl)propyl)isoindoline-5-carboxamide | 478.2 | B | ** |
| 192 | 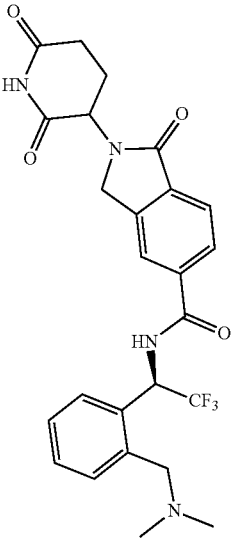 [SMILES: CN(C)Cc1ccccc1[C@@H](NC(=O)c1ccc2c(c1)CN(C1CCC(=O)NC1=O)C2=O)C(F)(F)F] | N-((R)-1-(2-((dimethylamino)methyl)phenyl)-2,2,2-trifluoroethyl)-2-(2,6-dioxopiperidin-3-yl)-1-oxoisoindoline-5-carboxamide | 503.3 | C | * |
| 193 | 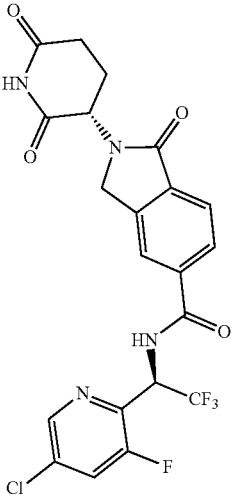 [SMILES: O=C1CC[C@H](N2Cc3cc(C(=O)N[C@H](c4ncc(Cl)cc4F)C(F)(F)F)ccc3C2=O)C(=O)N1] | N-((R)-1-(5-chloro-3-fluoropyridin-2-yl)-2,2,2-trifluoroethyl)-2-((S)-2,6-dioxopiperidin-3-yl)-1-oxoisoindoline-5-carboxamide | 499 | C | * |

TABLE 1-continued
| Cmpd No. | Cmpd Structure | Cmpd Name | MH+ | DC50 | Y |
|---|---|---|---|---|---|
| 194 | 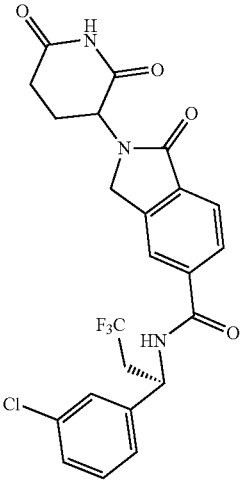 [SMILES: O=C1CCC(N2Cc3cc(C(=O)N[C@H](CC(F)(F)F)c4cccc(Cl)c4)ccc3C2=O)C(=O)N1] | N-((R)-1-(3-chlorophenyl)-3,3,3-trifluoropropyl)-2-(2,6-dioxopiperidin-3-yl)-1-oxoisoindoline-5-carboxamide | 494.1 | C | ** |
| 195 | 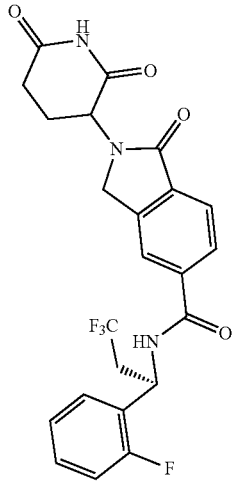 [SMILES: O=C1CCC(N2Cc3cc(C(=O)N[C@H](CC(F)(F)F)c4ccccc4F)ccc3C2=O)C(=O)N1] | 2-(2,6-dioxopiperidin-3-yl)-1-oxo-N-((R)-3,3,3-trifluoro-1-(2-fluorophenyl)propyl)isoindoline-5-carboxamide | 478.1 | C | * |
| 196 | 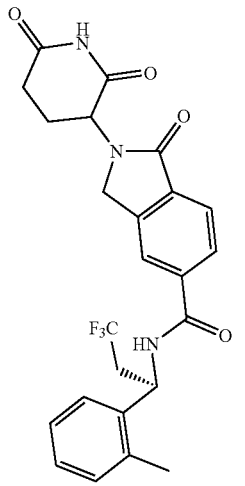 [SMILES: Cc1ccccc1[C@@H](CC(F)(F)F)NC(=O)c1ccc2c(c1)CN(C1CCC(=O)NC1=O)C2=O] | 2-(2,6-dioxopiperidin-3-yl)-1-oxo-N-((R)-3,3,3-trifluoro-1-o-tolylpropyl)isoindoline-5-carboxamide | 474.2 | C | * |

TABLE 1-continued

| Cmpd No. | Cmpd Name | MH+ | DC$_{50}$ | Y |
|---|---|---|---|---|
| 197 | 2-(2,6-dioxopiperidin-3-yl)-1-oxo-N-((S)-2,2,2-trifluoro-1-(2-fluorophenyl)ethyl)isoindoline-5-carboxamide | 464.2 | A | *** |
| 198 | N-((R)-1-(2-chloro-4-((dimethylamino)methyl)phenyl)-2,2,2-trifluoroethyl)-2-(2,6-dioxopiperidin-3-yl)-1-oxoisoindoline-5-carboxamide | 537.2 | C | * |
| 199 | 2-(2,6-dioxopiperidin-3-yl)-1-oxo-N-((R)-2,2,2-trifluoro-1-(3-methylpyridin-2-yl)ethyl)isoindoline-5-carboxamide | 461.1 | C | * |

TABLE 1-continued
| Cmpd No. | Cmpd Structure | Cmpd Name | MH+ | DC$_{50}$ | Y |
|---|---|---|---|---|---|
| 200 | 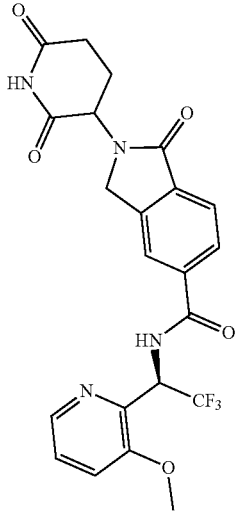 | 2-(2,6-dioxopiperidin-3-yl)-1-oxo-N-((R)-2,2,2-trifluoro-1-(3-methoxypyridin-2-yl)ethyl)isoindoline-5-carboxamide | 477.1 | C | * |
| 201 | 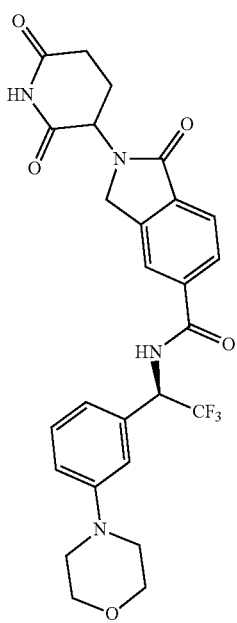 [SMILES: O=C1CCC(N2Cc3cc(C(=O)N[C@H](c4cccc(N5CCOCC5)c4)C(F)(F)F)ccc3C2=O)C(=O)N1] | 2-(2,6-dioxopiperidin-3-yl)-1-oxo-N-((R)-2,2,2-trifluoro-1-(3-morpholinophenyl)ethyl)isoindoline-5-carboxamide | 531.3 | C | * |

TABLE 1-continued

| Cmpd No. | Cmpd Structure | Cmpd Name | MH+ | DC$_{50}$ | Y |
|---|---|---|---|---|---|
| 202 | | N-((R)-1-(3-chloro-5-((dimethylamino)methyl)pyridin-2-yl)-2,2,2-trifluoroethyl)-2-(2,6-dioxopiperidin-3-yl)-1-oxoisoindoline-5-carboxamide | 538.2 | C | * |
| 203 | | N-((R)-1-(2-chloro-4,6-difluorophenyl)-2,2,2-trifluoroethyl)-2-(2,6-dioxopiperidin-3-yl)-1-oxoisoindoline-5-carboxamide | 516 | C | * |
| 204 | | 2-(2,6-dioxopiperidin-3-yl)-1-oxo-N-((R)-2,2,2-trifluoro-1-(4-morpholinophenyl)ethyl)isoindoline-5-carboxamide | 531.2 | C | * |

TABLE 1-continued

| Cmpd No. | Cmpd Structure | Cmpd Name | MH+ | DC$_{50}$ | Y |
|---|---|---|---|---|---|
| 205 | | 2-(2,6-dioxopiperidin-3-yl)-1-oxo-N-((R)-2,2,2-trifluoro-1-(2-morpholinophenyl)ethyl)isoindoline-5-carboxamide | 531.2 | C | * |
| 206 | | 2-(2,6-dioxopiperidin-3-yl)-1-oxo-N-((R)-2,2,2-trifluoro-1-(2-(4-methylpiperazin-1-yl)phenyl)ethyl)isoindoline-5-carboxamide | 544.3 | C | * |
| 207 | | N-((R)-1-(3,5-dichloropyridin-2-yl)-2,2,2-trifluoroethyl)-2-((S)-2,6-dioxopiperidin-3-yl)-1-oxoisoindoline-5-carboxamide | 515.2 | C | * |

TABLE 1-continued

| Cmpd No. | Cmpd Name | MH+ | DC$_{50}$ | Y |
|---|---|---|---|---|
| 208 | 2-(2,6-dioxopiperidin-3-yl)-1-oxo-N-((R)-2,2,2-trifluoro-1-(4-(4-methylpiperazin-1-yl)phenyl)ethyl)isoindoline-5-carboxamide | 544.3 | C | * |
| 209 | 2-(2,6-dioxopiperidin-3-yl)-1-oxo-N-((R)-2,2,2-trifluoro-1-(3-(4-methylpiperazin-1-yl)phenyl)ethyl)isoindoline-5-carboxamide | 544.3 | B | ** |

A number of references have been cited, the disclosures of which are incorporated herein by reference in their entirety.

What is claimed is:

1. A compound of Formula (I)

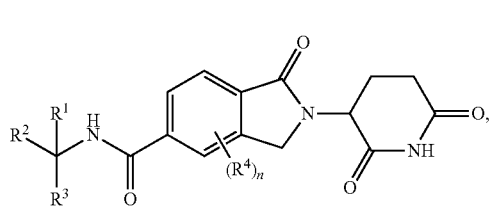

or a pharmaceutically acceptable salt, tautomer, or stereoisomer thereof,
wherein:
$R^1$ is $C_{1-3}$ alkyl, or $C_{1-3}$ fluoroalkyl;
$R^2$ is substituted or unsubstituted $C_{1-6}$ alkyl, substituted or unsubstituted $C_{3-10}$ cycloalkyl, substituted or unsubstituted 3-6-membered heterocyclyl, substituted or unsubstituted $C_{6-10}$ aryl, or substituted or unsubstituted 5-10-membered heteroaryl;
substituents on $R^2$ when present, are selected from F, Cl, Br, CN, OH, $OCH_3$, $OCF_3$, $OCH_2CH_3$, O-n-propyl, O-isopropyl, O-n-butyl, O-sec-butyl, O-tert-butyl, O-cyclopropyl, O-cyclobutyl, O-phenyl, $CH_3$, $CH_2CH_3$, $CF_3$, $CH_2CF_3$, $CH_2NHCH_3$, $CH_2N(CH_3)_2$, and a —($C_{0-3}$ alkyl)(3-6 membered heterocyclyl) selected from piperidyl, piperazinyl, morpholino, $CH_2$-aziridyl, $CH_2$-pyrrolidyl, $CH_2$-piperazinyl, $CH_2$-piperidyl, $CH_2$-morpholinyl, and $CH_2$(2-oxa-6-azaspiro[3.3]heptyl), wherein the —($C_{0-3}$ alkyl)(3-6 membered heterocyclyl) is optionally substituted with one or more F, Cl or $CH_3$;
$R^3$ is H;
$R^4$ is halogen; and
n is 0-3.

2. The compound of claim 1, wherein the compound is a compound of Formula (II)

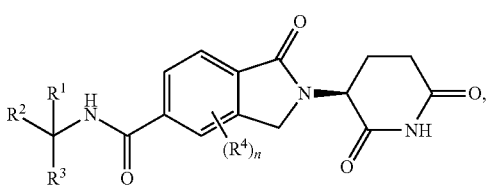

or a pharmaceutically acceptable salt, tautomer, or stereoisomer thereof.

3. The compound of claim 1, wherein the compound is a compound of Formula (III)

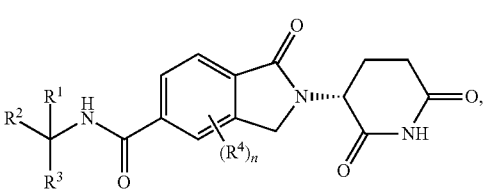

or a pharmaceutically acceptable salt, tautomer, or stereoisomer thereof.

4. The compound of claim 1, wherein the compound is a compound of Formula (IV)

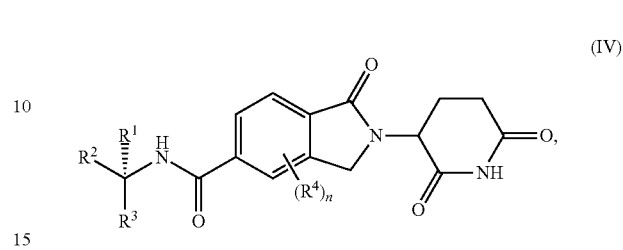

or a pharmaceutically acceptable salt, tautomer, or stereoisomer thereof.

5. The compound of claim 1, wherein the compound is a compound of Formula (V)

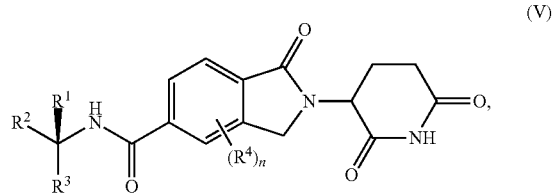

or a pharmaceutically acceptable salt, tautomer, or stereoisomer thereof.

6. The compound of claim 1, wherein the compound is a compound of Formula (VI)

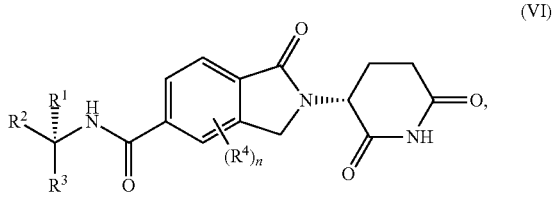

or a pharmaceutically acceptable salt, tautomer, or stereoisomer thereof.

7. The compound of claim 1, wherein the compound is a compound of Formula (VII)

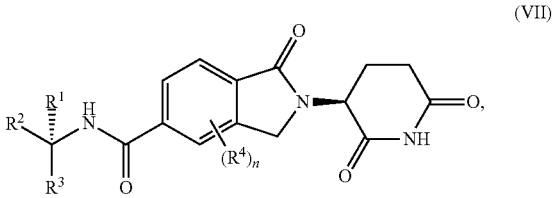

or a pharmaceutically acceptable salt, tautomer, or stereoisomer thereof.

8. The compound of claim 1, wherein the compound is a compound of Formula (VIII)

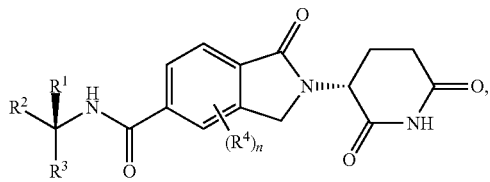
(VIII)

or a pharmaceutically acceptable salt, tautomer, or stereoisomer thereof.

9. The compound of claim 1, wherein the compound is a compound of Formula (IX)

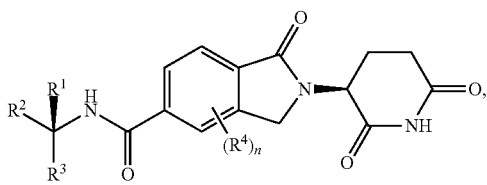
(IX)

or a pharmaceutically acceptable salt, tautomer, or stereoisomer thereof.

10. The compound of claim 1, wherein the compound is a compound of Formula (X)

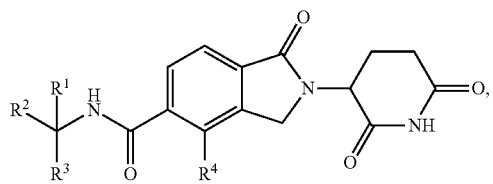
(X)

or a pharmaceutically acceptable salt, tautomer, or stereoisomer thereof.

11. The compound of claim 1, wherein the compound is a compound of Formula (XI)

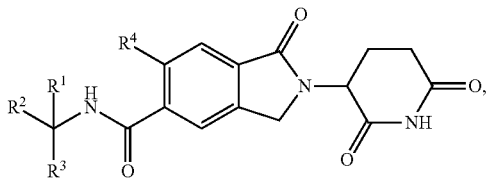
(XI)

or a pharmaceutically acceptable salt, tautomer, or stereoisomer thereof.

12. The compound of claim 1, wherein $R^1$ is methyl, ethyl, n-propyl, isopropyl, $CH_2F$, $CHF_2$, $CF_3$, $CH_2CH_2F$, $CH_2CHF_2$, $CH_2CF_3$, $CHFCH_3$, $CF_2CH_3$, or $CF_2CF_3$.

13. The compound of claim 1, wherein $R^1$ is methyl, ethyl, isopropyl, $CHF_2$, $CF_3$, $CH_2CF_3$, or $CF_2CF_3$.

14. The compound of claim 1, wherein $R^2$ is substituted with one or more substituents selected from F, Cl, CN, OH, $OCH_3$, $OCF_3$, O-isopropyl, O-cyclopropyl, O-phenyl, $CH_3$, $CF_3$, $CH_2CF_3$, $CH_2N(CH_3)_2$, and a —($C_{0-3}$ alkyl)(3-6 membered heterocyclyl) selected from morpholino, piperazinyl, $CH_2$-aziridyl, $CH_2$-pyrrolidyl, $CH_2$-piperazinyl, $CH_2$-morpholinyl, and $CH_2$(2-oxa-6-azaspiro[3.3]heptyl), wherein the —($C_{0-3}$ alkyl)(3-6 membered heterocyclyl) is optionally substituted with one or more F or $CH_3$.

15. The compound of claim 1, wherein $R^2$ is $C_{1-6}$ alkyl, unsubstituted or substituted with one or more substituents independently selected from F, CN, and OH.

16. The compound of claim 15, wherein $R^2$ is $CH_3$, isopropyl, ter-butyl, $C(CH_3)_2CH_2OH$, $C(CH_3)_2CN$, or $C(CH_3)_2CF_3$.

17. The compound of claim 1, wherein $R^2$ is $C_{3-10}$ cycloalkyl, unsubstituted, or substituted with one or more substitutents independently selected from F, OH, $CH_3$, $C(CH_3)_2OH$, and $CF_3$.

18. The compound of claim 17 wherein $R^2$ is cyclopropyl, cyclobutyl, cyclopentyl, cyclohexyl, spiro[3.5]nonyl, bicyclo[1.1.1]pentyl, or spiro[2.5]octyl.

19. The compound of claim 1, wherein $R^2$ is 3-6-membered heterocyclyl, unsubstituted, or substituted with one or more $CH_3$, and $CH_2CF_3$.

20. The compound of claim 19, wherein $R^2$ is oxetanyl, tetrahydropyranyl or piperidyl.

21. The compound of claim 1, wherein $R^2$ is $C_{6-10}$ aryl, unsubstituted or substituted with one or more substituents independently selected from F, Cl, CN, OH, $OCH_3$, $OCF_3$, O-isopropyl, O-cyclopropyl, O-phenyl, $CH_3$, $CF_3$, and $CH_2N(CH_3)_2$; and —($C_{0-3}$ alkyl)(3-6 membered heterocyclyl) selected from piperazinyl, morpholino, $CH_2$-aziridyl, $CH_2$-pyrrolidyl, $CH_2$-piperazinyl, $CH_2$-morpholinyl, and $CH_2$(2-oxa-6-azaspiro[3.3]heptyl), wherein the —($C_{0-3}$ alkyl)(3-6 membered heterocyclyl) is optionally substituted with one or more F, or $CH_3$.

22. The compound of claim 21, wherein $R^2$ is phenyl.

23. The compound of claim 1, wherein $R^2$ is 5-10-membered heteroaryl, unsubstituted or substituted with one or more substituents independently selected from F, Cl, $OCH_3$, $CH_3$, $CF_3$, and $CH_2N(CH_3)_2$.

24. The compound of claim 1, wherein $R^2$ is pyrazolyl, pyrazinyl, pyridyl, or pyrimidyl.

25. The compound of claim 1, wherein $R^4$ is F or Cl.

26. The compound of claim 1, wherein n is 0, 1 or 2.

27. A compound selected from the group consisting of
2-(2,6-dioxopiperidin-3-yl)-1-oxo-N—((S)-1-phenylethyl)isoindoline-5-carboxamide;
2-(2,6-dioxopiperidin-3-yl)-N-isopropyl-1-oxoisoindoline-5-carboxamide;
N—((S)-1-cyclopentylethyl)-2-(2,6-dioxopiperidin-3-yl)-1-oxoisoindoline-5-carboxamide;
N—((S)-1-cyclohexylethyl)-2-(2,6-dioxopiperidin-3-yl)-1-oxoisoindoline-5-carboxamide;
N—((S)-1-cyclopropylethyl)-2-(2,6-dioxopiperidin-3-yl)-1-oxoisoindoline-5-carboxamide;
2-(2,6-dioxopiperidin-3-yl)-1-oxo-N—((S)-1-phenylpropyl)isoindoline-5-carboxamide;
2-(2,6-dioxopiperidin-3-yl)-1-oxo-N—((S)-1-p-tolylethyl)isoindoline-5-carboxamide;
N—((S)-1-(4-chlorophenyl)ethyl)-2-(2,6-dioxopiperidin-3-yl)-1-oxoisoindoline-5-carboxamide;
N—((S)-1-cyclobutylethyl)-2-(2,6-dioxopiperidin-3-yl)-1-oxoisoindoline-5-carboxamide;
2-(2,6-dioxopiperidin-3-yl)-1-oxo-N—((S)-1-(pyridin-2-yl)ethyl)isoindoline-5-carboxamide;
N—((S)-1-(3-cyanophenyl)ethyl)-2-(2,6-dioxopiperidin-3-yl)-1-oxoisoindoline-5-carboxamide;

2-(2,6-dioxopiperidin-3-yl)-N—((S)-1-(4-methoxyphenyl)ethyl)-1-oxoisoindoline-5-carboxamide;
2-(2,6-dioxopiperidin-3-yl)-N—((S)-1-(3-methoxyphenyl)ethyl)-1-oxoisoindoline-5-carboxamide;
2-(2,6-dioxopiperidin-3-yl)-N—((S)-1-(2-methoxyphenyl)ethyl)-1-oxoisoindoline-5-carboxamide;
N—((S)-1-(3-chlorophenyl)ethyl)-2-(2,6-dioxopiperidin-3-yl)-1-oxoisoindoline-5-carboxamide;
2-(2,6-dioxopiperidin-3-yl)-N—((S)-1-(4-fluorophenyl)ethyl)-1-oxoisoindoline-5-carboxamide;
2-(2,6-dioxopiperidin-3-yl)-N—((S)-1-(3-fluorophenyl)ethyl)-1-oxoisoindoline-5-carboxamide;
2-(2,6-dioxopiperidin-3-yl)-N—((S)-1-(2-fluorophenyl)ethyl)-1-oxoisoindoline-5-carboxamide;
2-(2,6-dioxopiperidin-3-yl)-1-oxo-N—((S)-1-(pyridin-3-yl)ethyl)isoindoline-5-carboxamide;
2-(2,6-dioxopiperidin-3-yl)-1-oxo-N—((S)-1-o-tolylethyl)isoindoline-5-carboxamide;
N—((S)-1-(2-chlorophenyl)ethyl)-2-(2,6-dioxopiperidin-3-yl)-1-oxoisoindoline-5-carboxamide;
N—((R)-1-cyclohexylethyl)-2-(2,6-dioxopiperidin-3-yl)-1-oxoisoindoline-5-carboxamide;
N—((R)-1-cyclohexyl-2,2,2-trifluoroethyl)-2-(2,6-dioxopiperidin-3-yl)-1-oxoisoindoline-5-carboxamide;
2-(2,6-dioxopiperidin-3-yl)-1-oxo-N—((R)-2,2,2-trifluoro-1-phenylethyl)isoindoline-5-carboxamide;
2-(2,6-dioxopiperidin-3-yl)-1-oxo-N—((S)-3,3,3-trifluoro-1-phenylpropyl)isoindoline-5-carboxamide;
2-(2,6-dioxopiperidin-3-yl)-1-oxo-N—((S)-1-(tetrahydro-2H-pyran-4-yl)ethyl)isoindoline-5-carboxamide;
N—((S)-1-cyclohexyl-2-methylpropyl)-2-(2,6-dioxopiperidin-3-yl)-1-oxoisoindoline-5-carboxamide;
2-(2,6-dioxopiperidin-3-yl)-N—((S)-3-methylbutan-2-yl)-1-oxoisoindoline-5-carboxamide;
N—((S)-1-cyclohexyl-3,3,3-trifluoropropyl)-2-(2,6-dioxopiperidin-3-yl)-1-oxoisoindoline-5-carboxamide;
N—((S)-3,3-dimethylbutan-2-yl)-2-(2,6-dioxopiperidin-3-yl)-1-oxoisoindoline-5-carboxamide;
2-(2,6-dioxopiperidin-3-yl)-1-oxo-N—((R)-1,1,1-trifluoro-3-methylbutan-2-yl)isoindoline-5-carboxamide;
2-(2,6-dioxopiperidin-3-yl)-1-oxo-N—((R)-2,2,2-trifluoro-1-(4-fluorophenyl)ethyl)isoindoline-5-carboxamide;
2-(2,6-dioxopiperidin-3-yl)-1-oxo-N—((R)-2,2,2-trifluoro-1-(3-methoxyphenyl)ethyl)isoindoline-5-carboxamide;
2-(2,6-dioxopiperidin-3-yl)-1-oxo-N—((R)-1,1,1-trifluoro-3,3-dimethylbutan-2-yl)isoindoline-5-carboxamide;
2-(2,6-dioxopiperidin-3-yl)-1-oxo-N—((R)-2,2,2-trifluoro-1-(4-methoxyphenyl)ethyl)isoindoline-5-carboxamide;
2-(2,6-dioxopiperidin-3-yl)-1-oxo-N—((R)-2,2,2-trifluoro-1-(tetrahydro-2H-pyran-4-yl)ethyl)isoindoline-5-carboxamide;
2-(2,6-dioxopiperidin-3-yl)-1-oxo-N—((R)-2,2,2-trifluoro-1-(3-fluorophenyl)ethyl)isoindoline-5-carboxamide;
2-(2,6-dioxopiperidin-3-yl)-1-oxo-N—((R)-2,2,2-trifluoro-1-(2-methoxyphenyl)ethyl)isoindoline-5-carboxamide;
2-(2,6-dioxopiperidin-3-yl)-1-oxo-N—((R)-2,2,2-trifluoro-1-(pyridin-4-yl)ethyl)isoindoline-5-carboxamide;
2-(2,6-dioxopiperidin-3-yl)-1-oxo-N—((R)-2,2,2-trifluoro-1-(4-(trifluoromethyl)phenyl)ethyl)isoindoline-5-carboxamide;
2-(2,6-dioxopiperidin-3-yl)-1-oxo-N—((R)-2,2,2-trifluoro-1-(4-(trifluoromethoxy)phenyl)ethyl)isoindoline-5-carboxamide;
N—((R)-1-(4-chlorophenyl)-2,2,2-trifluoroethyl)-2-(2,6-dioxopiperidin-3-yl)-1-oxoisoindoline-5-carboxamide;
N—((R)-1-(3-chlorophenyl)-2,2,2-trifluoroethyl)-2-(2,6-dioxopiperidin-3-yl)-1-oxoisoindoline-5-carboxamide;
2-(2,6-dioxopiperidin-3-yl)-1-oxo-N—((R)-2,2,2-trifluoro-1-(2-(trifluoromethoxy)phenyl)ethyl)isoindoline-5-carboxamide;
N—((R)-1-(4,4-difluorocyclohexyl)-2,2,2-trifluoroethyl)-2-(2,6-dioxopiperidin-3-yl)-1-oxoisoindoline-5-carboxamide;
N—((R)-1-(4,4-dimethylcyclohexyl)-2,2,2-trifluoroethyl)-2-(2,6-dioxopiperidin-3-yl)-1-oxoisoindoline-5-carboxamide;
2-(2,6-dioxopiperidin-3-yl)-1-oxo-N—((R)-2,2,2-trifluoro-1-(2-(trifluoromethyl)phenyl)ethyl)isoindoline-5-carboxamide;
2-(2,6-dioxopiperidin-3-yl)-1-oxo-N—((R)-2,2,2-trifluoro-1-(pyridin-2-yl)ethyl)isoindoline-5-carboxamide;
2-(2,6-dioxopiperidin-3-yl)-1-oxo-N—((R)-2,2,2-trifluoro-1-(2-fluorophenyl)ethyl)isoindoline-5-carboxamide;
N—((R)-1-(2-chlorophenyl)-2,2,2-trifluoroethyl)-2-(2,6-dioxopiperidin-3-yl)-1-oxoisoindoline-5-carboxamide;
N—((S)-1-(2,4-difluorophenyl)ethyl)-2-(2,6-dioxopiperidin-3-yl)-1-oxoisoindoline-5-carboxamide;
2-(2,6-dioxopiperidin-3-yl)-1-oxo-N—((R)-2,2,2-trifluoro-1-(3-(trifluoromethyl)phenyl)ethyl)isoindoline-5-carboxamide;
2-(2,6-dioxopiperidin-3-yl)-1-oxo-N-((1R)-2,2,2-trifluoro-1-(spiro[3.5]nonan-7-yl)ethyl)isoindoline-5-carboxamide;
2-(2,6-dioxopiperidin-3-yl)-1-oxo-N—((R)-2,2,2-trifluoro-1-(pyridin-3-yl)ethyl)isoindoline-5-carboxamide;
N—((S)-1-(4-chloro-2-fluorophenyl)ethyl)-2-(2,6-dioxopiperidin-3-yl)-1-oxoisoindoline-5-carboxamide;
2-(2,6-dioxopiperidin-3-yl)-1-oxo-N—((R)-2,2,2-trifluoro-1-((1r,4R)-4-hydroxycyclohexyl)ethyl)isoindoline-5-carboxamide;
N—((R)-1-(bicyclo[1.1.1]pentan-1-yl)-2,2,2-trifluoroethyl)-2-(2,6-dioxopiperidin-3-yl)-1-oxoisoindoline-5-carboxamide;
2-(2,6-dioxopiperidin-3-yl)-1-oxo-N—((R)-2,2,2-trifluoro-1-(3-(trifluoromethoxy)phenyl)ethyl)isoindoline-5-carboxamide;
N—((S)-1-(2-chloro-4-fluorophenyl)ethyl)-2-(2,6-dioxopiperidin-3-yl)-1-oxoisoindoline-5-carboxamide;
2-((R)-2,6-dioxopiperidin-3-yl)-1-oxo-N—((R)-2,2,2-trifluoro-1-phenylethyl)isoindoline-5-carboxamide;
2-((S)-2,6-dioxopiperidin-3-yl)-1-oxo-N—((R)-2,2,2-trifluoro-1-phenylethyl)isoindoline-5-carboxamide;
2-(2,6-dioxopiperidin-3-yl)-1-oxo-N—((R)-2,2,2-trifluoro-1-((1s,4S)-4-hydroxycyclohexyl)ethyl)isoindoline-5-carboxamide;
N—((R)-1-(4-cyanophenyl)-2,2,2-trifluoroethyl)-2-(2,6-dioxopiperidin-3-yl)-1-oxoisoindoline-5-carboxamide;
N—((R)-1-(3-cyanophenyl)-2,2,2-trifluoroethyl)-2-(2,6-dioxopiperidin-3-yl)-1-oxoisoindoline-5-carboxamide;

2-(2,6-dioxopiperidin-3-yl)-1-oxo-N—((R)-2,2,2-trifluoro-1-(1-methyl-1H-pyrazol-3-yl)ethyl)isoindoline-5-carboxamide;
2-(2,6-dioxopiperidin-3-yl)-1-oxo-N—((R)-2,2,2-trifluoro-1-(pyrimidin-5-yl)ethyl)isoindoline-5-carboxamide;
2-(2,6-dioxopiperidin-3-yl)-1-oxo-N—((R)-2,2,2-trifluoro-1-(4-fluoro-2-methoxyphenyl)ethyl)isoindoline-5-carboxamide;
2-(2,6-dioxopiperidin-3-yl)-N—((R)-1,1,1,4,4,4-hexafluoro-3,3-dimethylbutan-2-yl)-1-oxoisoindoline-5-carboxamide;
2-(2,6-dioxopiperidin-3-yl)-1-oxo-N—((R)-2,2,2-trifluoro-1-(1-methyl-1H-pyrazol-5-yl)ethyl)isoindoline-5-carboxamide;
2-(2,6-dioxopiperidin-3-yl)-1-oxo-N—((R)-2,2,2-trifluoro-1-(1-methyl-1H-pyrazol-4-yl)ethyl)isoindoline-5-carboxamide;
2-(2,6-dioxopiperidin-3-yl)-1-oxo-N-((1R)-2,2,2-trifluoro-1-(4-(trifluoromethyl)cyclohexyl)ethyl)isoindoline-5-carboxamide;
N—((R)-1-(2-chloro-4-fluorophenyl)-2,2,2-trifluoroethyl)-2-(2,6-dioxopiperidin-3-yl)-1-oxoisoindoline-5-carboxamide;
N—((R)-1-(3,4-difluorophenyl)-2,2,2-trifluoroethyl)-2-(2,6-dioxopiperidin-3-yl)-1-oxoisoindoline-5-carboxamide;
2-(2,6-dioxopiperidin-3-yl)-1-oxo-N—((R)-2,2,2-trifluoro-1-(1-methylcyclobutyl)ethyl)isoindoline-5-carboxamide;
2-(2,6-dioxopiperidin-3-yl)-1-oxo-N—((R)-2,2,2-trifluoro-1-(1-(trifluoromethyl)cyclopropyl)ethyl)isoindoline-5-carboxamide;
2-(2,6-dioxopiperidin-3-yl)-1-oxo-N—((R)-2,2,2-trifluoro-1-(5-fluoropyridin-2-yl)ethyl)isoindoline-5-carboxamide;
2-(2,6-dioxopiperidin-3-yl)-1-oxo-N—((R)-2,2,2-trifluoro-1-(4-fluoro-2-(trifluoromethyl)phenyl)ethyl)isoindoline-5-carboxamide;
2-(2,6-dioxopiperidin-3-yl)-1-oxo-N—((R)-2,2,2-trifluoro-1-(1-methylcyclopropyl)ethyl)isoindoline-5-carboxamide;
N—((R)-1-(4-chloro-2-fluorophenyl)-2,2,2-trifluoroethyl)-2-(2,6-dioxopiperidin-3-yl)-1-oxoisoindoline-5-carboxamide;
N—((R)-1-(2,4-difluorophenyl)-2,2,2-trifluoroethyl)-2-(2,6-dioxopiperidin-3-yl)-1-oxoisoindoline-5-carboxamide;
2-(2,6-dioxopiperidin-3-yl)-1-oxo-N—((R)-2,2,2-trifluoro-1-(1-methylpiperidin-4-yl)ethyl)isoindoline-5-carboxamide;
2-(2,6-dioxopiperidin-3-yl)-1-oxo-N—((R)-2,2,2-trifluoro-1-(pyrazin-2-yl)ethyl)isoindoline-5-carboxamide;
2-(2,6-dioxopiperidin-3-yl)-1-oxo-N—((R)-2,2,2-trifluoro-1-(1-methylcylopentyl)ethyl)isoindoline-5-carboxamide;
2-(2,6-dioxopiperidin-3-yl)-6-fluoro-1-oxo-N—((R)-2,2,2-trifluoro-1-phenylethyl)isoindoline-5-carboxamide;
2-(2,6-dioxopiperidin-3-yl)-6-fluoro-1-oxo-N—((S)-1-phenylethyl)isoindoline-5-carboxamide;
2-(2,6-dioxopiperidin-3-yl)-1-oxo-N—((R)-2,2,2-trifluoro-1-(4-fluoro-2-(trifluoromethoxy)phenyl)ethyl)isoindoline-5-carboxamide;
N—((R)-3-cyano-1,1,1-trifluoro-3-methylbutan-2-yl)-2-(2,6-dioxopiperidin-3-yl)-1-oxoisoindoline-5-carboxamide;
2-(2,6-dioxopiperidin-3-yl)-6-fluoro-1-oxo-N—((R)-2,2,2-trifluoro-1-(2-(trifluoromethyl)phenyl)ethyl)isoindoline-5-carboxamide;
2-(2,6-dioxopiperidin-3-yl)-4-fluoro-1-oxo-N—((R)-2,2,2-trifluoro-1-phenylethyl)isoindoline-5-carboxamide;
2-(2,6-dioxopiperidin-3-yl)-6-fluoro-1-oxo-N—((R)-2,2,2-trifluoro-1-(3-(trifluoromethyl)phenyl)ethyl)isoindoline-5-carboxamide;
N—((R)-1-(4-chlorophenyl)-2,2,2-trifluoroethyl)-2-(2,6-dioxopiperidin-3-yl)-6-fluoro-1-oxoisoindoline-5-carboxamide;
2-(2,6-dioxopiperidin-3-yl)-6-fluoro-1-oxo-N—((R)-2,2,2-trifluoro-1-(4-fluorophenyl)ethyl)isoindoline-5-carboxamide;
N—((R)-1-(4-chlorophenyl)-2,2,2-trifluoroethyl)-2-(2,6-dioxopiperidin-3-yl)-4-fluoro-1-oxoisoindoline-5-carboxamide;
2-(2,6-dioxopiperidin-3-yl)-1-oxo-N—((R)-2,2,2-trifluoro-1-(3-methyloxetan-3-yl)ethyl)isoindoline-5-carboxamide;
2-(2,6-dioxopiperidin-3-yl)-1-oxo-N—((R)-1,1,1-trifluoro-4-hydroxy-3,3-dimethylbutan-2-yl)isoindoline-5-carboxamide;
2-(2,6-dioxopiperidin-3-yl)-4-fluoro-1-oxo-N—((R)-2,2,2-trifluoro-1-(4-fluorophenyl)ethyl)isoindoline-5-carboxamide;
2-(2,6-dioxopiperidin-3-yl)-4-fluoro-1-oxo-N—((R)-2,2,2-trifluoro-1-(3-(trifluoromethyl)phenyl)ethyl)isoindoline-5-carboxamide;
2-(2,6-dioxopiperidin-3-yl)-4-fluoro-1-oxo-N—((R)-2,2,2-trifluoro-1-(2-(trifluoromethyl)phenyl)ethyl)isoindoline-5-carboxamide;
2-(2,6-dioxopiperidin-3-yl)-6-fluoro-1-oxo-N—((R)-2,2,2-trifluoro-1-(2-fluorophenyl)ethyl)isoindoline-5-carboxamide;
2-(2,6-dioxopiperidin-3-yl)-4-fluoro-1-oxo-N—((R)-2,2,2-trifluoro-1-(2-fluorophenyl)ethyl)isoindoline-5-carboxamide;
2-(2,6-dioxopiperidin-3-yl)-1-oxo-N—((R)-2,2,2-trifluoro-1-(4-hydroxyphenyl)ethyl)isoindoline-5-carboxamide;
2-(2,6-dioxopiperidin-3-yl)-1-oxo-N—((R)-2,2,2-trifluoro-1-(3-isopropoxyphenyl)ethyl)isoindoline-5-carboxamide;
2-((S)-2,6-dioxopiperidin-3-yl)-1-oxo-N—((R)-2,2,2-trifluoro-1-(4-fluorophenyl)ethyl)isoindoline-5-carboxamide;
2-((R)-2,6-dioxopiperidin-3-yl)-1-oxo-N—((R)-2,2,2-trifluoro-1-(4-fluorophenyl)ethyl)isoindoline-5-carboxamide;
N—((R)-1-(2,4-difluorophenyl)-2,2,2-trifluoroethyl)-2-(2,6-dioxopiperidin-3-yl)-4-fluoro-1-oxoisoindoline-5-carboxamide;
N—((R)-1-(3-chloropyridin-2-yl)-2,2,2-trifluoroethyl)-2-(2,6-dioxopiperidin-3-yl)-1-oxoisoindoline-5-carboxamide;
N—((R)-1-(3-chlorophenyl)-2,2,2-trifluoroethyl)-2-(2,6-dioxopiperidin-3-yl)-4-fluoro-1-oxoisoindoline-5-carboxamide;
2-(2,6-dioxopiperidin-3-yl)-4-fluoro-1-oxo-N—((R)-2,2,2-trifluoro-1-(3-fluorophenyl)ethyl)isoindoline-5-carboxamide;
N—((R)-1-(5-chloropyridin-2-yl)-2,2,2-trifluoroethyl)-2-(2,6-dioxopiperidin-3-yl)-1-oxoisoindoline-5-carboxamide;

2-(2,6-dioxopiperidin-3-yl)-1-oxo-N—((R)-2,2,2-trifluoro-1-(3-fluoropyridin-2-yl)ethyl)isoindoline-5-carboxamide;

N—((R)-2,2-difluoro-1-(4-fluorophenyl)ethyl)-2-(2,6-dioxopiperidin-3-yl)-1-oxoisoindoline-5-carboxamide;

N—((R)-2,2-difluoro-1-(4-fluorophenyl)ethyl)-2-(2,6-dioxopiperidin-3-yl)-4-fluoro-1-oxoisoindoline-5-carboxamide;

N—((R)-1-(3,4-difluorophenyl)-2,2,2-trifluoroethyl)-2-(2,6-dioxopiperidin-3-yl)-4-fluoro-1-oxoisoindoline-5-carboxamide;

N—((R)-1-(2-chlorophenyl)-2,2,2-trifluoroethyl)-2-(2,6-dioxopiperidin-3-yl)-4-fluoro-1-oxoisoindoline-5-carboxamide;

2-(2,6-dioxopiperidin-3-yl)-4-fluoro-1-oxo-N—((R)-2,2,2-trifluoro-1-(5-fluoropyridin-2-yl)ethyl)isoindoline-5-carboxamide;

2-(2,6-dioxopiperidin-3-yl)-1-oxo-N—((R)-2,2,2-trifluoro-1-(3-(trifluoromethyl)pyridin-2-yl)ethyl)isoindoline-5-carboxamide;

2-(2,6-dioxopiperidin-3-yl)-4-fluoro-1-oxo-N—((R)-2,2,2-trifluoro-1-(3-fluoropyridin-2-yl)ethyl)isoindoline-5-carboxamide;

2-(2,6-dioxopiperidin-3-yl)-1-oxo-N—((R)-1-phenylpropyl)isoindoline-5-carboxamide;

2-(2,6-dioxopiperidin-3-yl)-1-oxo-N—((R)-2,2,2-trifluoro-1-(4-(trifluoromethyl)pyridin-2-yl)ethyl)isoindoline-5-carboxamide;

2-(2,6-dioxopiperidin-3-yl)-4-fluoro-1-oxo-N—((R)-2,2,2-trifluoro-1-(3-(trifluoromethoxy)phenyl)ethyl)isoindoline-5-carboxamide;

N—((R)-1-cyclohexyl-2,2,2-trifluoroethyl)-2-(2,6-dioxopiperidin-3-yl)-4-fluoro-1-oxoisoindoline-5-carboxamide;

N—((R)-1-(3-cyclopropoxyphenyl)-2,2,2-trifluoroethyl)-2-(2,6-dioxopiperidin-3-yl)-1-oxoisoindoline-5-carboxamide;

2-(2,6-dioxopiperidin-3-yl)-1-oxo-N—((S)-3,3,3-trifluoro-1-(4-fluorophenyl)propyl)isoindoline-5-carboxamide;

2-(2,6-dioxopiperidin-3-yl)-N—((R)-2-methyl-1-phenylpropyl)-1-oxoisoindoline-5-carboxamide;

2-(2,6-dioxopiperidin-3-yl)-1-oxo-N—((R)-2,2,2-trifluoro-1-(6-(trifluoromethyl)pyridin-2-yl)ethyl)isoindoline-5-carboxamide;

2-(2,6-dioxopiperidin-3-yl)-1-oxo-N—((R)-2,2,2-trifluoro-1-(5-(trifluoromethyl)pyridin-2-yl)ethyl)isoindoline-5-carboxamide;

N—((R)-1-(5-chloro-3-fluoropyridin-2-yl)-2,2,2-trifluoroethyl)-2-(2,6-dioxopiperidin-3-yl)-1-oxoisoindoline-5-carboxamide;

2-(2,6-dioxopiperidin-3-yl)-4-fluoro-1-oxo-N—((R)-2,2,2-trifluoro-1-o-tolylethyl)isoindoline-5-carboxamide;

N—((S)-1-(4-chlorophenyl)-3,3,3-trifluoropropyl)-2-(2,6-dioxopiperidin-3-yl)-4-fluoro-1-oxoisoindoline-5-carboxamide;

N—((R)-1-(4-cyclopropoxyphenyl)-2,2,2-trifluoroethyl)-2-(2,6-dioxopiperidin-3-yl)-4-fluoro-1-oxoisoindoline-5-carboxamide;

N—((R)-1-(2-cyanophenyl)ethyl)-2-(2,6-dioxopiperidin-3-yl)-1-oxoisoindoline-5-carboxamide;

N—((R)-1-cyclopentylethyl)-2-(2,6-dioxopiperidin-3-yl)-1-oxoisoindoline-5-carboxamide;

N—((R)-1-(3,5-difluoropyridin-2-yl)-2,2,2-trifluoroethyl)-2-(2,6-dioxopiperidin-3-yl)-1-oxoisoindoline-5-carboxamide;

2-(2,6-dioxopiperidin-3-yl)-4-fluoro-1-oxo-N—((R)-2,2,2-trifluoro-1-m-tolylethyl)isoindoline-5-carboxamide;

2-(2,6-dioxopiperidin-3-yl)-4-fluoro-1-oxo-N—((R)-2,2,2-trifluoro-1-(4-(trifluoromethoxy)phenyl)ethyl)isoindoline-5-carboxamide;

2-(2,6-dioxopiperidin-3-yl)-4-fluoro-1-oxo-N—((R)-2,2,2-trifluoro-1-(2-(trifluoromethoxy)phenyl)ethyl)isoindoline-5-carboxamide;

N—((R)-1-cyclopentyl-2,2,2-trifluoroethyl)-2-(2,6-dioxopiperidin-3-yl)-4-fluoro-1-oxoisoindoline-5-carboxamide;

N—((R)-1-(bicyclo[1.1.1]pentan-1-yl)-2,2,2-trifluoroethyl)-2-(2,6-dioxopiperidin-3-yl)-4-fluoro-1-oxoisoindoline-5-carboxamide;

N—((R)-1-(3-chloropyridin-2-yl)-2,2,2-trifluoroethyl)-2-(2,6-dioxopiperidin-3-yl)-4-fluoro-1-oxoisoindoline-5-carboxamide;

2-(2,6-dioxopiperidin-3-yl)-1-oxo-N—((R)-2,2,2-trifluoro-1-(3-(morpholinomethyl)phenyl)ethyl)isoindoline-5-carboxamide;

N—((R)-1-(4-((dimethylamino)methyl)phenyl)-2,2,2-trifluoroethyl)-2-(2,6-dioxopiperidin-3-yl)-1-oxoisoindoline-5-carboxamide;

2-(2,6-dioxopiperidin-3-yl)-1-oxo-N—((R)-2,2,2-trifluoro-1-(4-(morpholinomethyl)phenyl)ethyl)isoindoline-5-carboxamide;

2-(2,6-dioxopiperidin-3-yl)-1-oxo-N—((R)-2,2,2-trifluoro-1-(1-(2,2,2-trifluoroethyl)piperidin-4-yl)ethyl)isoindoline-5-carboxamide;

2-(2,6-dioxopiperidin-3-yl)-4-fluoro-1-oxo-N—((R)-2,2,2-trifluoro-1-p-tolylethyl)isoindoline-5-carboxamide;

N—((R)-1-(2-chloro-4-fluorophenyl)-2,2,2-trifluoroethyl)-2-(2,6-dioxopiperidin-3-yl)-4-fluoro-1-oxoisoindoline-5-carboxamide;

2-(2,6-dioxopiperidin-3-yl)-4-fluoro-1-oxo-N—((S)-3,3,3-trifluoro-1-(3-fluorophenyl)propyl)isoindoline-5-carboxamide;

2-(2,6-dioxopiperidin-3-yl)-1-oxo-N—((R)-2,2,2-trifluoro-1-(4-phenoxyphenyl)ethyl)isoindoline-5-carboxamide;

N—((R)-1-(4-cyclopropoxyphenyl)-2,2,2-trifluoroethyl)-2-(2,6-dioxopiperidin-3-yl)-1-oxoisoindoline-5-carboxamide;

N—((S)-1-(4-chlorophenyl)-3,3,3-trifluoropropyl)-2-(2,6-dioxopiperidin-3-yl)-1-oxoisoindoline-5-carboxamide;

N—((R)-1-(3-((dimethylamino)methyl)phenyl)-2,2,2-trifluoroethyl)-2-(2,6-dioxopiperidin-3-yl)-1-oxoisoindoline-5-carboxamide;

N—((R)-1-(2-chloro-6-fluorophenyl)-2,2,2-trifluoroethyl)-2-(2,6-dioxopiperidin-3-yl)-1-oxoisoindoline-5-carboxamide;

N—((R)-1-(2-chloro-3-fluorophenyl)-2,2,2-trifluoroethyl)-2-(2,6-dioxopiperidin-3-yl)-1-oxoisoindoline-5-carboxamide;

4-chloro-2-(2,6-dioxopiperidin-3-yl)-1-oxo-N—((R)-2,2,2-trifluoro-1-(4-fluorophenyl)ethyl)isoindoline-5-carboxamide;

2-(2,6-dioxopiperidin-3-yl)-N—((S)-2-methyl-1-phenylpropyl)-1-oxoisoindoline-5-carboxamide;

2-(2,6-dioxopiperidin-3-yl)-1-oxo-N—((R)-2,2,2-trifluoro-1-(2-(morpholinomethyl)phenyl)ethyl)isoindoline-5-carboxamide;

2-(2,6-dioxopiperidin-3-yl)-1-oxo-N—((R)-2,2,2-trifluoro-1-((1r,4R)-4-hydroxy-4-methylcyclohexyl)ethyl)isoindoline-5-carboxamide;

N—((R)-1-(2-cyclopropoxyphenyl)-2,2,2-trifluoroethyl)-2-(2,6-dioxopiperidin-3-yl)-4-fluoro-1-oxoisoindoline-5-carboxamide;
2-(2,6-dioxopiperidin-3-yl)-1-oxo-N—((R)-2,2,2-trifluoro-1-(3-phenoxyphenyl)ethyl)isoindoline-5-carboxamide;
2-(2,6-dioxopiperidin-3-yl)-1-oxo-N—((R)-2,2,2-trifluoro-1-(2-phenoxyphenyl)ethyl)isoindoline-5-carboxamide;
N—((R)-1-(2-chloro-5-fluorophenyl)-2,2,2-trifluoroethyl)-2-(2,6-dioxopiperidin-3-yl)-1-oxoisoindoline-5-carboxamide;
N—((R)-1-(2-cyclopropoxyphenyl)-2,2,2-trifluoroethyl)-2-(2,6-dioxopiperidin-3-yl)-1-oxoisoindoline-5-carboxamide;
2-(2,6-dioxopiperidin-3-yl)-1-oxo-N—((S)-3,3,3-trifluoro-1-(3-fluorophenyl)propyl)isoindoline-5-carboxamide;
N—((R)-1-(2,4-dichlorophenyl)-2,2,2-trifluoroethyl)-2-(2,6-dioxopiperidin-3-yl)-1-oxoisoindoline-5-carboxamide;
N—((R)-1-(2,4-dichlorophenyl)-2,2,2-trifluoroethyl)-2-(2,6-dioxopiperidin-3-yl)-4-fluoro-1-oxoisoindoline-5-carboxamide;
2-(2,6-dioxopiperidin-3-yl)-1-oxo-N—((R)-2,2,2-trifluoro-1-(3-(2-hydroxypropan-2-yl)bicyclo[1.1.1]pentan-1-yl)ethyl)isoindoline-5-carboxamide;
2-(2,6-dioxopiperidin-3-yl)-1-oxo-N-((1R)-2,2,2-trifluoro-1-(spiro[2.5]octan-6-yl)ethyl)isoindoline-5-carboxamide;
2-(2,6-dioxopiperidin-3-yl)-N—((S)-1-(2-fluorophenyl)-2-methylpropyl)-1-oxoisoindoline-5-carboxamide;
2-(2,6-dioxopiperidin-3-yl)-1-oxo-N—((R)-2,2,2-trifluoro-1-((1s,4S)-4-hydroxy-4-methylcyclohexyl)ethyl)isoindoline-5-carboxamide;
N—((S)-1-(2-chlorophenyl)-2-methylpropyl)-2-(2,6-dioxopiperidin-3-yl)-1-oxoisoindoline-5-carboxamide;
2-(2,6-dioxopiperidin-3-yl)-N—((S)-1-(4-fluorophenyl)-2-methylpropyl)-1-oxoisoindoline-5-carboxamide;
N—((R)-1-(3-chloropyridin-2-yl)-2-methylpropyl)-2-(2,6-dioxopiperidin-3-yl)-1-oxoisoindoline-5-carboxamide;
N—((S)-1-(3-chloropyridin-2-yl)-2-methylpropyl)-2-(2,6-dioxopiperidin-3-yl)-1-oxoisoindoline-5-carboxamide;
N—((R)-1-(3-chloropyridin-2-yl)-2,2,2-trifluoroethyl)-2-((S)-2,6-dioxopiperidin-3-yl)-1-oxoisoindoline-5-carboxamide;
N-(2,2-difluoro-1-(4-fluorophenyl)propyl)-2-(2,6-dioxopiperidin-3-yl)-1-oxoisoindoline-5-carboxamide;
N—((R)-1-(3-chloro-5-fluoropyridin-2-yl)-2,2,2-trifluoroethyl)-2-(2,6-dioxopiperidin-3-yl)-1-oxoisoindoline-5-carboxamide;
2-(2,6-dioxopiperidin-3-yl)-1-oxo-N-(2,2,2-trifluoro-1-(2-hydroxyspiro[3.5]nonan-7-yl)ethyl)isoindoline-5-carboxamide;
N—((S)-1-(4-chlorophenyl)-2-methylpropyl)-2-(2,6-dioxopiperidin-3-yl)-1-oxoisoindoline-5-carboxamide;
N—((R)-1-(3,5-dichloropyridin-2-yl)-2,2,2-trifluoroethyl)-2-(2,6-dioxopiperidin-3-yl)-4-fluoro-1-oxoisoindoline-5-carboxamide;
N-((1R)-1-(4-(2-oxa-6-azaspiro[3.3]heptan-6-ylmethyl)phenyl)-2,2,2-trifluoroethyl)-2-(2,6-dioxopiperidin-3-yl)-1-oxoisoindoline-5-carboxamide;
2-(2,6-dioxopiperidin-3-yl)-1-oxo-N—((R)-2,2,2-trifluoro-1-(4-(pyrrolidin-1-ylmethyl)phenyl)ethyl)isoindoline-5-carboxamide;
2-(2,6-dioxopiperidin-3-yl)-1-oxo-N-(2,2,2-trifluoro-1-(2-hydroxyspiro[3.5]nonan-7-yl)ethyl)isoindoline-5-carboxamide;
N—((R)-1-(3-chloropyridin-2-yl)-2,2,2-trifluoroethyl)-2-((R)-2,6-dioxopiperidin-3-yl)-1-oxoisoindoline-5-carboxamide;
N—((R)-1-(3-chloro-5-fluoropyridin-2-yl)-2,2,2-trifluoroethyl)-2-(2,6-dioxopiperidin-3-yl)-4-fluoro-1-oxoisoindoline-5-carboxamide;
N—((R)-1-(3,5-dichloropyridin-2-yl)-2,2,2-trifluoroethyl)-2-(2,6-dioxopiperidin-3-yl)-1-oxoisoindoline-5-carboxamide;
2-(2,6-dioxopiperidin-3-yl)-1-oxo-N—((R)-2,2,2-trifluoro-1-(4-((4-methylpiperazin-1-yl)methyl)phenyl)ethyl)isoindoline-5-carboxamide;
N—((R)-1-(4-((dimethylamino)methyl)phenyl)-2,2,2-trifluoroethyl)-2-(2,6-dioxopiperidin-3-yl)-4-fluoro-1-oxoisoindoline-5-carboxamide;
2-(2,6-dioxopiperidin-3-yl)-1-oxo-N—((R)-3,3,3-trifluoro-1-phenylpropyl)isoindoline-5-carboxamide;
N—((R)-1-(4-((3,3-difluoroazetidin-1-yl)methyl)phenyl)-2,2,2-trifluoroethyl)-2-(2,6-dioxopiperidin-3-yl)-1-oxoisoindoline-5-carboxamide;
N—((R)-1-(4-(azetidin-1-ylmethyl)phenyl)-2,2,2-trifluoroethyl)-2-(2,6-dioxopiperidin-3-yl)-1-oxoisoindoline-5-carboxamide;
2-(2,6-dioxopiperidin-3-yl)-1-oxo-N—((R)-3,3,3-trifluoro-1-(3-fluorophenyl)propyl)isoindoline-5-carboxamide;
2-(2,6-dioxopiperidin-3-yl)-1-oxo-N—((R)-3,3,3-trifluoro-1-(4-fluorophenyl)propyl)isoindoline-5-carboxamide;
N—((R)-1-(2-((dimethylamino)methyl)phenyl)-2,2,2-trifluoroethyl)-2-(2,6-dioxopiperidin-3-yl)-1-oxoisoindoline-5-carboxamide;
N—((R)-1-(5-chloro-3-fluoropyridin-2-yl)-2,2,2-trifluoroethyl)-2-((S)-2,6-dioxopiperidin-3-yl)-1-oxoisoindoline-5-carboxamide;
N—((R)-1-(3-chlorophenyl)-3,3,3-trifluoropropyl)-2-(2,6-dioxopiperidin-3-yl)-1-oxoisoindoline-5-carboxamide;
2-(2,6-dioxopiperidin-3-yl)-1-oxo-N—((R)-3,3,3-trifluoro-1-(2-fluorophenyl)propyl)isoindoline-5-carboxamide;
2-(2,6-dioxopiperidin-3-yl)-1-oxo-N—((R)-3,3,3-trifluoro-1-o-tolylpropyl)isoindoline-5-carboxamide;
2-(2,6-dioxopiperidin-3-yl)-1-oxo-N—((S)-2,2,2-trifluoro-1-(2-fluorophenyl)ethyl)isoindoline-5-carboxamide;
N—((R)-1-(2-chloro-4-((dimethylamino)methyl)phenyl)-2,2,2-trifluoroethyl)-2-(2,6-dioxopiperidin-3-yl)-1-oxoisoindoline-5-carboxamide;
2-(2,6-dioxopiperidin-3-yl)-1-oxo-N—((R)-2,2,2-trifluoro-1-(3-methylpyridin-2-yl)ethyl)isoindoline-5-carboxamide;
2-(2,6-dioxopiperidin-3-yl)-1-oxo-N—((R)-2,2,2-trifluoro-1-(3-methoxypyridin-2-yl)ethyl)isoindoline-5-carboxamide;
2-(2,6-dioxopiperidin-3-yl)-1-oxo-N—((R)-2,2,2-trifluoro-1-(3-morpholinophenyl)ethyl)isoindoline-5-carboxamide;
N—((R)-1-(3-chloro-5-((dimethylamino)methyl)pyridin-2-yl)-2,2,2-trifluoroethyl)-2-(2,6-dioxopiperidin-3-yl)-1-oxoisoindoline-5-carboxamide;
N—((R)-1-(2-chloro-4,6-difluorophenyl)-2,2,2-trifluoroethyl)-2-(2,6-dioxopiperidin-3-yl)-1-oxoisoindoline-5-carboxamide;

2-(2,6-dioxopiperidin-3-yl)-1-oxo-N—((R)-2,2,2-trifluoro-1-(4-morpholinophenyl)ethyl)isoindoline-5-carboxamide;

2-(2,6-dioxopiperidin-3-yl)-1-oxo-N—((R)-2,2,2-trifluoro-1-(2-morpholinophenyl)ethyl)isoindoline-5-carboxamide;

2-(2,6-dioxopiperidin-3-yl)-1-oxo-N—((R)-2,2,2-trifluoro-1-(2-(4-methylpiperazin-1-yl)phenyl)ethyl)isoindoline-5-carboxamide;

N—((R)-1-(3,5-dichloropyridin-2-yl)-2,2,2-trifluoroethyl)-2-((S)-2,6-dioxopiperidin-3-yl)-1-oxoisoindoline-5-carboxamide;

2-(2,6-dioxopiperidin-3-yl)-1-oxo-N—((R)-2,2,2-trifluoro-1-(4-(4-methylpiperazin-1-yl)phenyl)ethyl)isoindoline-5-carboxamide and;

2-(2,6-dioxopiperidin-3-yl)-1-oxo-N—((R)-2,2,2-trifluoro-1-(3-(4-methylpiperazin-1-yl)phenyl)ethyl)isoindoline-5-carboxamide;

or a pharmaceutically acceptable salt, tautomer, or stereoisomer thereof.

28. A pharmaceutical composition comprising an effective amount of a compound of claim 1, or a pharmaceutically acceptable salt, tautomer, or stereoisomer thereof, and a pharmaceutically acceptable carrier, excipient or vehicle.

29. A method for treating acute myeloid leukemia, the method comprising administering to a subject in need thereof an effective amount of a compound of claim 1.

30. A method for treating acute myeloid leukemia, the method comprising administering to a subject in need thereof an effective amount of the pharmaceutical composition of claim 28.

31. The method of claim 29, wherein the acute myeloid leukemia is newly diagnosed acute myeloid leukemia.

32. The method of claim 31, wherein the acute myeloid leukemia is relapsed, refractory or resistant to conventional therapy.

33. A method for reducing CK1α protein levels, the method comprising contacting a cell with an effective amount of a compound of claim 1.

34. The method of claim 33, wherein the cell is in a subject.

35. A method for reducing CK1α protein levels in a cell ex vivo or in vitro, the method comprising contacting a cell with an effective amount of a compound of claim 1.

\* \* \* \* \*

UNITED STATES PATENT AND TRADEMARK OFFICE
CERTIFICATE OF CORRECTION

PATENT NO. : 11,306,101 B2
APPLICATION NO. : 16/887766
DATED : April 19, 2022
INVENTOR(S) : Frans Baculi et al.

It is certified that error appears in the above-identified patent and that said Letters Patent is hereby corrected as shown below:

On the Title Page

In item (56) (4th listed reference under Other Publications), replace "CKIα" with --CK1α--;

In the Claims

In Column 212, Claim 15, Line 12, replace the term "ter-butyl" with --tert-butyl--;

In Column 212, Claim 17, Line 16, replace the term "substitutents" with --substituents--;

In Column 215, Claim 27, Lines 56, replace "1-methylcylopentyl" with --1-methylcyclopentyl--.

Signed and Sealed this
Eighteenth Day of October, 2022

Katherine Kelly Vidal
*Director of the United States Patent and Trademark Office*